US011762541B2

(12) United States Patent
Kozuka et al.

(10) Patent No.: US 11,762,541 B2
(45) Date of Patent: *Sep. 19, 2023

(54) CONTROL METHOD AND RECORDING MEDIUM

(71) Applicant: Panasonic Corporation, Osaka (JP)

(72) Inventors: Kazuki Kozuka, Fukui (JP); Kazutoyo Takata, Fukui (JP); Kenji Kondo, Fukui (JP); Hirohiko Kimura, Fukui (JP); Toyohiko Sakai, Fukui (JP)

(73) Assignee: Panasonic Holdings Corporation, Osaka (JP)

( * ) Notice: Subject to any disclaimer, the term of this patent is extended or adjusted under 35 U.S.C. 154(b) by 134 days.

This patent is subject to a terminal disclaimer.

(21) Appl. No.: 17/394,554

(22) Filed: Aug. 5, 2021

(65) Prior Publication Data

US 2021/0365175 A1 Nov. 25, 2021

Related U.S. Application Data

(63) Continuation of application No. 16/785,761, filed on Feb. 10, 2020, now Pat. No. 11,112,954, which is a (Continued)

(30) Foreign Application Priority Data

Jun. 4, 2014 (JP) .................................. 2014-116173

(51) Int. Cl.
*G06F 3/04845* (2022.01)
*G06F 3/0488* (2022.01)
(Continued)

(52) U.S. Cl.
CPC ........ *G06F 3/04845* (2013.01); *G06F 3/0485* (2013.01); *G06F 3/0488* (2013.01);
(Continued)

(58) Field of Classification Search
CPC .. G06F 3/04845; G06F 3/0485; G06F 3/0488; G06F 16/5866; G06F 2203/04104;
(Continued)

(56) References Cited

U.S. PATENT DOCUMENTS 3,534,338 A * 10/1970 Pinson ................ G06F 3/04845
345/520
2003/0088387 A1 5/2003 Chang
(Continued)

FOREIGN PATENT DOCUMENTS

JP 2006-14928 1/2006
JP 2006-305204 11/2006
(Continued)

OTHER PUBLICATIONS

Translation of WO-2012132840-A1 (Year: 2012).*
(Continued)

*Primary Examiner* — Fonya M Long
*Assistant Examiner* — Kimberly A. Sass
(74) *Attorney, Agent, or Firm* — Wenderoth, Lind & Ponack, L.L.P.

(57) ABSTRACT

A method for controlling an information terminal causes a computer of the information terminal to receive, from a case retrieval system, a plurality of similar medical images having a feature quantity of a region of interest and a certain degree of similarity in accordance with the region of interest included in a target medical image, displays a display screen displaying the plurality of received similar medical images on a touch panel display, the display screen including a display region in which at least some of the plurality of received similar medical images are displayed, displays, if selection of a first similar medical image from among the at least some of the plurality of received similar medical images displayed in the display region is detected, the first
(Continued)

similar medical image across the display region, and displays, if a swipe operation performed on the first similar medical image is detected, a second similar medical image, which has second highest similarity next to the first similar medical image among the plurality of similar medical images, in the display region such that a corresponding region of interest included in the second similar medical image is located at a certain position in the display region.

12 Claims, 62 Drawing Sheets

Related U.S. Application Data continuation of application No. 14/722,197, filed on May 27, 2015, now Pat. No. 10,599,810.

(51) Int. Cl.
| | | |
|---|---|---|
| *G06F 16/58* | (2019.01) | |
| *G16H 50/70* | (2018.01) | |
| *G06F 3/0485* | (2022.01) | |
| *G16H 30/20* | (2018.01) | |
| *G16H 30/40* | (2018.01) | |

(52) U.S. Cl.
CPC ......... *G06F 16/5866* (2019.01); *G16H 30/20* (2018.01); *G16H 30/40* (2018.01); *G16H 50/70* (2018.01); *G06F 2203/04104* (2013.01); *G06F 2203/04803* (2013.01); *G06F 2203/04806* (2013.01); *G06V 2201/03* (2022.01)

(58) Field of Classification Search
CPC ............ G06F 2203/04803; G06F 2203/04806; G16H 30/20; G16H 30/40; G16H 50/70; G06V 2201/03
See application file for complete search history.

(56) References Cited

U.S. PATENT DOCUMENTS

| | | | |
|---|---|---|---|
| 2005/0238218 A1 | 10/2005 | Nakamura | |
| 2007/0242069 A1* | 10/2007 | Matsue | G16H 30/40 |
| | | | 345/428 |
| 2008/0187248 A1* | 8/2008 | Ikeda | G06F 3/04845 |
| | | | 382/305 |
| 2008/0243395 A1 | 10/2008 | Oosawa et al. | |
| 2009/0088287 A1* | 4/2009 | Chludek | B60K 23/04 |
| | | | 475/246 |
| 2011/0099032 A1 | 4/2011 | Miyasa et al. | |
| 2012/0162222 A1* | 6/2012 | Zaiki | A61B 6/463 |
| | | | 345/660 |
| 2013/0273968 A1* | 10/2013 | Rhoads | H04N 23/611 |
| | | | 455/566 |
| 2013/0338496 A1* | 12/2013 | Hielscher | A61B 5/0064 |
| | | | 600/425 |
| 2015/0256763 A1* | 9/2015 | Niemi | G06F 3/04845 |
| | | | 348/700 |

FOREIGN PATENT DOCUMENTS

| | | | |
|---|---|---|---|
| JP | 2007-29341 | 2/2007 | |
| JP | 2008-257292 | 10/2008 | |
| JP | 2011-92286 | 5/2011 | |
| WO | WO-2012132840 A1 * | 10/2012 | ......... A61B 1/00009 |

OTHER PUBLICATIONS

Akira Oosawa et al., "Development of "SYNAPSE Case Match", Content-based Image Retrieval System for Supporting Image Diagnosis" Fujifilm Research&Development, No. 58, 2013, pp. 11-14.
Sunhyoung Han & Nuno Vasconcelos, "Object-based regions of interest for image compression", 2008, University of California San Diego, p. 1 (Year: 2008).
Tahmoush, "Image differencing approaches to medical image classification", Oct. 10-12, 2007, IEEE, 36th Applied Imagery Pattern Recognition Workshop, p. 22 (Year: 2007).

* cited by examiner

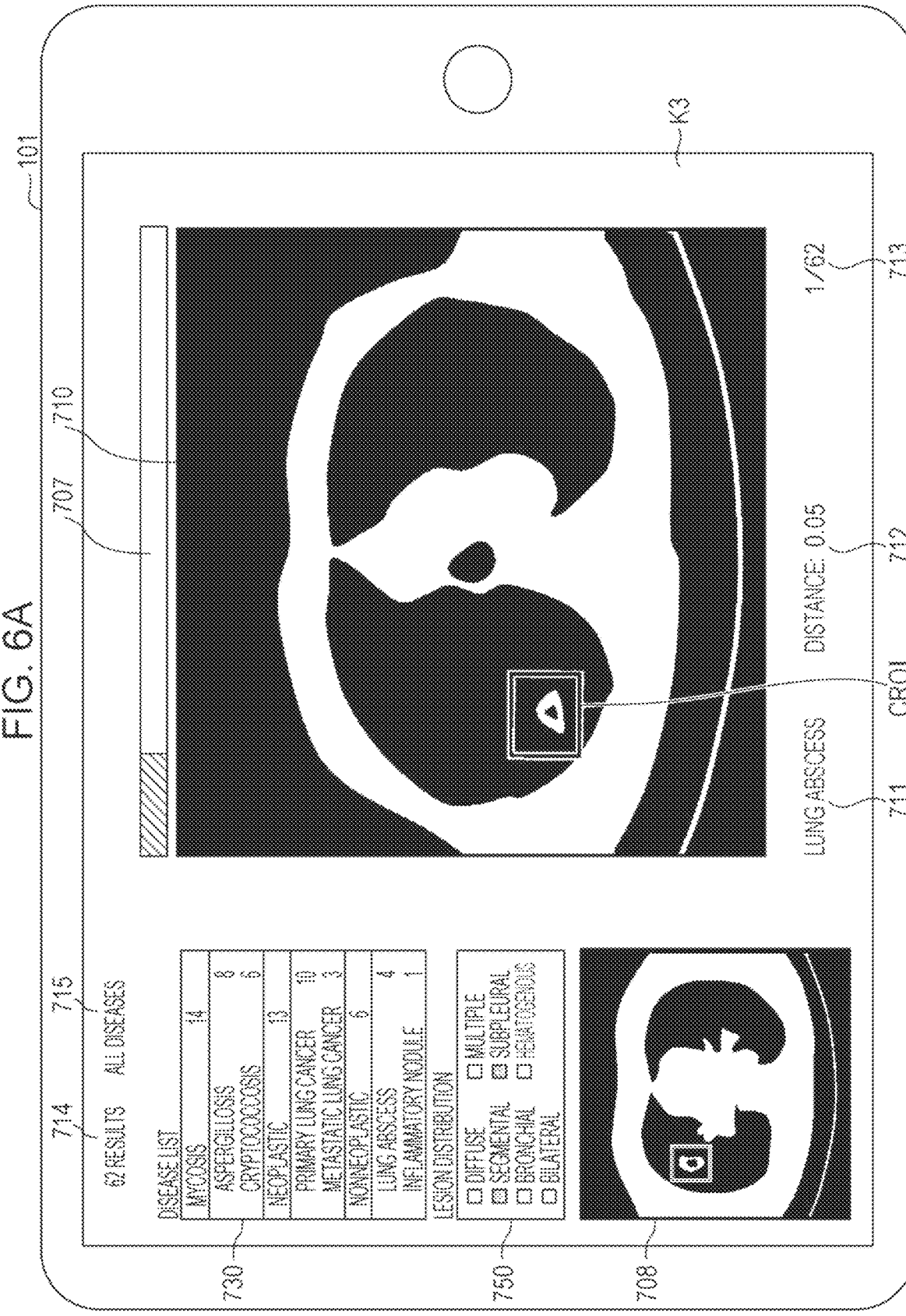

FIG. 7

| DISEASE LIST | | 730 |
|---|---|---|
| MYCOSIS | 14 | 731 |
|   ASPERGILLOSIS | 8 | 732 |
|   CRYPTOCOCCOSIS | 6 | 733 |
| NEOPLASTIC | 13 | 734 |
|   PRIMARY LUNG CANCER | 10 | 735 |
|   METASTATIC LUNG CANCER | 3 | 736 |
| NONNEOPLASTIC | 6 | 737 |
|   LUNG ABSCESS | 4 | 738 |
|   SARCOIDOSIS | 1 | 739 |
|   SEPTIC EMBOLI | 1 | 740 |
| MYCOBACTERIOSIS | 6 | 741 |
|   NON-TUBERCULOUS MYCOBACTERIUM | 4 | 742 |
|   LUNG TUBERCULOSIS | 2 | 743 |
| OTHERS | 2 | 744 |
|   BRONCHIECTASIS | 1 | 745 |
|   ... | 1 | |

FIG. 8
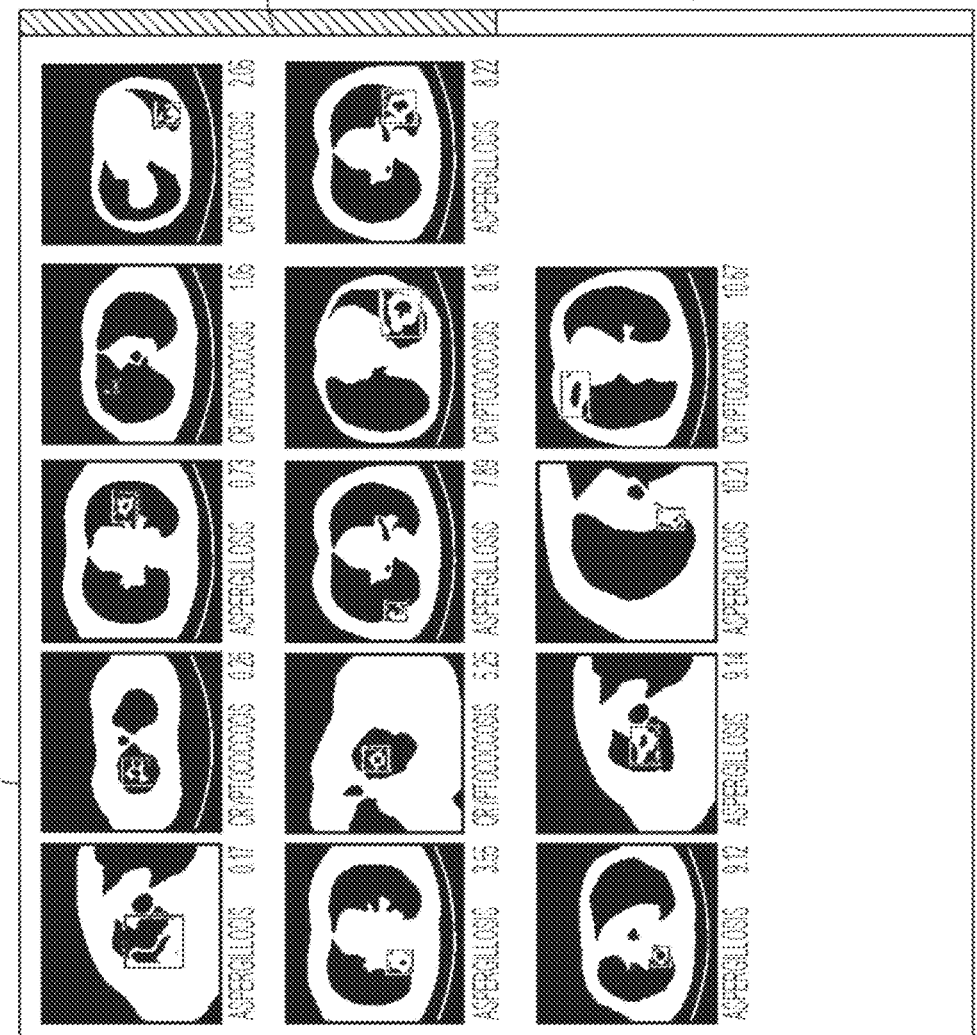
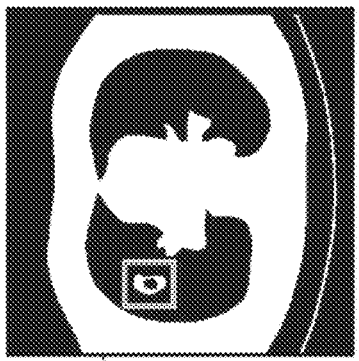

FIG. 12

LESION DISTRIBUTION ⸺750
- ☐ DIFFUSE ⸺751
- ▨ SEGMENTAL ⸺752
- ☐ BRONCHIAL ⸺753
- ☐ BILATERAL ⸺754
- ☐ MULTIPLE ⸺755
- ☐ SUBPLEURAL ⸺756
- ☐ HEMATOGENOUS ⸺757

FIG. 13

LESION DISTRIBUTION ⸺750
- ☐ DIFFUSE ⸺751
- ▨ SEGMENTAL ⸺752
- ☐ BRONCHIAL ⸺753
- ☑ BILATERAL ⸺754
- ☐ MULTIPLE ⸺755
- ☐ SUBPLEURAL ⸺756
- ☐ HEMATOGENOUS ⸺757

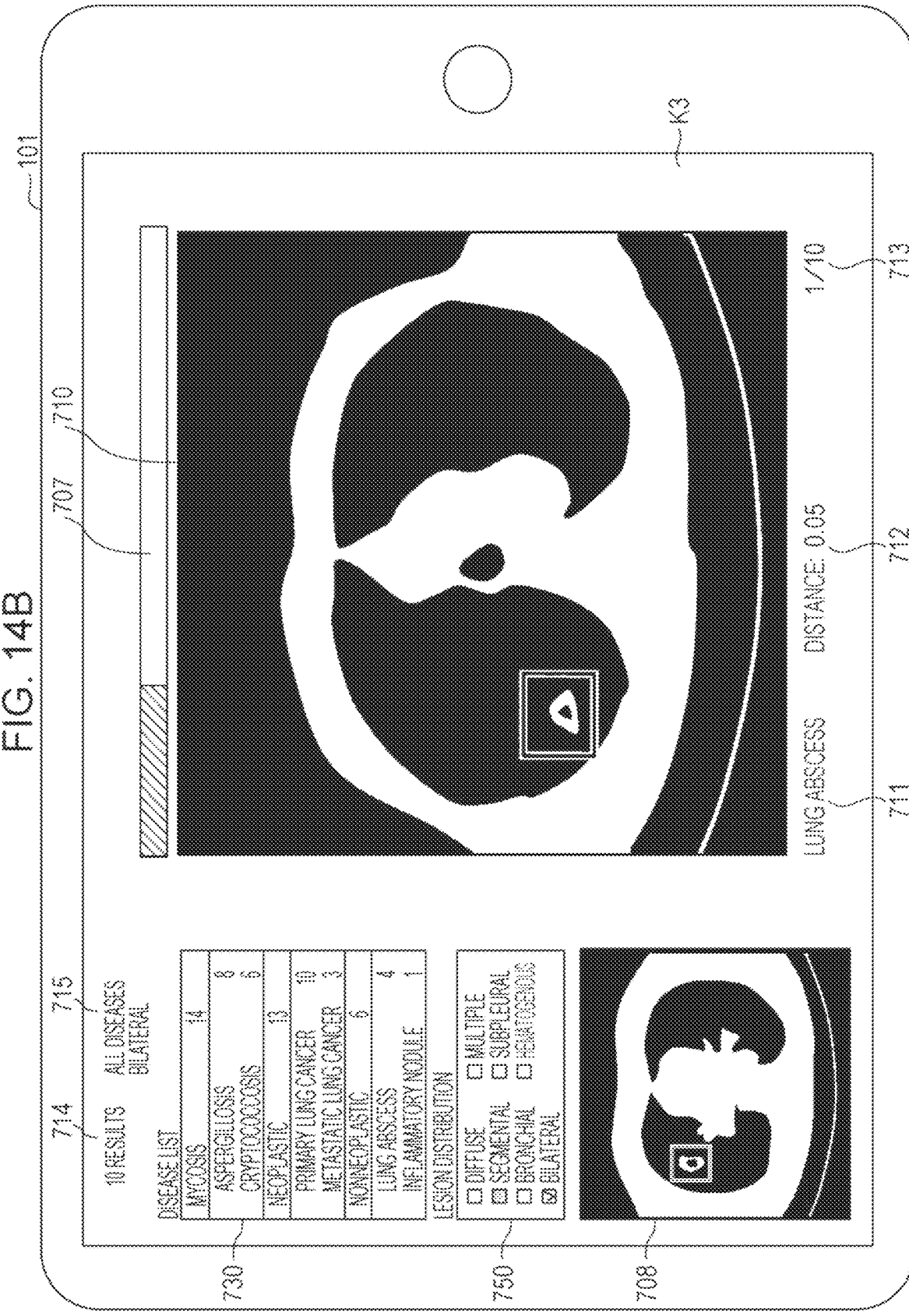

FIG. 15

LESION DISTRIBUTION — 750
- ☐ DIFFUSE — 751
- ▨ SEGMENTAL — 752
- ☑ BRONCHIAL — 753
- ☐ BILATERAL — 754
- ☐ MULTIPLE — 755
- ☐ SUBPLEURAL — 756
- ☐ HEMATOGENOUS — 757

FIG. 17

LESION DISTRIBUTION
―750
☐ DIFFUSE ―751   ☐ MULTIPLE ―755
▦ SEGMENTAL ―752   ☑ SUBPLEURAL ―756
☐ BRONCHIAL ―753   ☐ HEMATOGENOUS ―757
☐ BILATERAL ―754

| | | |
|---|---|---|
| 1100 | PATIENT ID | 123456 |
| 1200 | NAME | PANATARO |
| 1300 | AGE | 28 |
| 1400 | GENDER | MALE |
| 1500 | PAST MEDICAL HISTORY | NONE |
| 1600 | FAMILY MEDICAL HISTORY | NONE |
| 1700 | CHIEF COMPLAINT | COUGHING |
| 1800 | TEST INFORMATION | (REFER TO FIG. 20) |
| 1900 | CONFIRMED DIAGNOSIS | MYCOPLASMA PNEUMONIA |

| | | |
|---|---|---|
| 1810 | TEST ID | 13227895 |
| 1820 | TEST TIME | 2/5/20XX 10:00 |
| 1830 | TEST TYPE | BLOOD TEST |
| 1840 | TEST RESULTS | YYYY1 |

| | |
|---|---|
| TEST ID | 13227903 |
| TEST TIME | 2/5/20XX 11:00 |
| TEST TYPE | PLAIN ROENTGENOGRAPHY (CHEST) |
| TEST RESULTS | YYYY2 |

| | |
|---|---|
| TEST ID | 13227989 |
| TEST TIME | 2/9/20XX 9:00 |
| TEST TYPE | CT (CHEST) |
| TEST RESULTS | YYYY3 |

| TEST ID | 13227989 |
|---|---|
| OBSERVATIONS | MULTIPLE NODULES OF 0.5 TO 1 cm IN RIGHT LUNG FIELD... |
| DIAGNOSIS | SUSPICION OF INFLAMMATORY NODULES OR LUNG TUBERCULOSIS |

FIG. 23    4000

| | |
|---|---|
| SIMILAR CASE ID (4100) | SIM5232 |
| SLICE ID (4200) | CT149391025 |
| ROI INFORMATION (4300) | xl, yt, xr, yb |
| IMAGE FEATURE DATA (4400) | f1, f2, f3, ..., fN |
| THUMBNAIL IMAGE DATA (4500) | (I₀,₀, I₀,₁, ..., I_{w-1, h-1}) |
| LESION DISTRIBUTION INFORMATION (4600) | |
| CONFIRMED DIAGNOSIS (LARGE CATEGORY) (4700) | NEOPLASTIC |
| CONFIRMED DIAGNOSIS (SMALL CATEGORY) (4800) | PRIMARY LUNG CANCER |

| | |
|---|---|
| DIFFUSE (4610) | 1 |
| SEGMENTAL (4620) | 0 |
| BRONCHIAL (4630) | 0 |
| BILATERAL (4640) | 1 |
| MULTIPLE (4650) | 1 |
| SUBPLEURAL (4660) | 0 |
| HEMATOGENOUS (4670) | 1 |

FIG. 27
| PATIENT LIST | | | | |
|---|---|---|---|---|
| PATIENT ID | PATIENT NAME | TEST TIME | TEST ID | TEST TYPE |
| 443982 | ICHIRO YAMADA | 12/1/20XX | 23982874 | MR (HEAD) |
| 123456 | PANATARO | 5/8/20XX | 13227989 | CT (CHEST) |
| 345455 | ... | ... | ... | ... |
| 235982 | ... | ... | ... | ... |
| TEST LIST | | |
|---|---|---|
| SERIES ID | DEFINITION | IMAGE |
| CT152729 | LUNG FIELD CONDITION SLICE THICKNESS: 5 mm |  |
| CT152730 | LUNG FIELD CONDITION SLICE THICKNESS: 1 mm | 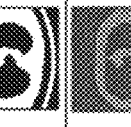 |
| CT152731 | MEDIASTINUM CONDITION SLICE THICKNESS: 5 mm |  |

FIG. 30

| DISEASE ID | LARGE CATEGORY | SMALL CATEGORY | NUMBER | SIMILAR CASE ID |
|---|---|---|---|---|
| DIS528 | NEOPLASTIC | PRIMARY LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NONNEOPLASTIC | LUNG ABSCESS | 4 | ... |
| ... | MYCOBACTERIOSIS | NON-TUBERCULOUS MYCOBACTERIUM | 4 | ... |
| ... | ... | ... | ... | ... |

FIG. 31

DISEASE LIST 730

| PRIMARY LUNG CANCER | 10 |
| ASPERGILLOSIS | 8 |
| CRYPTOCOCCOSIS | 6 |
| LUNG ABSCESS | 4 |
| NON-TUBERCULOUS MYCOBACTERIUM | 4 |
| METASTATIC LUNG CANCER | 3 |
| LUNG TUBERCULOSIS | 2 |
| INFLAMMATORY NODULE | 1 |
| SEPTIC EMBOLI | 1 |
| BRONCHIECTASIS | 1 |
| UNIDENTIFIED | 1 |

FIG. 32

DISEASE LIST 730

| MYCOSIS | 14 |
| NEOPLASTIC | 13 |
| NONNEOPLASTIC | 6 |
| MYCOBACTERIOSIS | 6 |
| OTHERS | 2 |

FIG. 33

| DISEASE LIST | 730 |
|---|---|
| MYCOSIS | 14 |
|   ASPERGILLOSIS | 8 |
|   CRYPTOCOCCOSIS | 6 |
| NEOPLASTIC | 13 |
|   PRIMARY LUNG CANCER | 10 |
|   METASTATIC LUNG CANCER | 3 |
| NONNEOPLASTIC | 6 |
|   LUNG ABSCESS | 4 |
|   SARCOIDOSIS | 1 |
|   SEPTIC EMBOLI | 1 |
| MYCOBACTERIOSIS | 6 |
|   NON-TUBERCULOUS MYCOBACTERIUM | 4 |
|   LUNG TUBERCULOSIS | 2 |
| OTHERS | 2 |
|   BRONCHIECTASIS | 1 |
|   ... | 1 |

FIG. 35

| TYPE OF DISTRIBUTION | NUMBER OF CASES | SIMILAR CASE ID |
|---|---|---|
| DIFFUSE | 3 | SIM2521, SIM4123, SIM5225 |
| SEGMENTAL | 0 | NONE |
| BRONCHIAL | 2 | SIM0006, SIM1892, SIM4399 |
| BILATERAL | 12 | ... |
| MULTIPLE | 22 | ... |
| SUBPLEURAL | 4 | ... |
| HEMATOGENOUS | 5 | ... |

CONTROL METHOD AND RECORDING MEDIUM

BACKGROUND

1. Technical Field

The present disclosure relates to a method for controlling an information terminal for retrieving medical images similar to a medical image to be read and a recording medium.

2. Description of the Related Art

Currently, medical imaging apparatuses for, for example, computed tomography (CT), magnetic resonance imaging (MRI), and the like are being developed and increasingly used. CT and MRI have made it possible to obtain a large number of high-definition digital medical images. In addition, medical images read by doctors are being accumulated in picture archiving and communication systems (PACSs) along with reading reports. For example, as disclosed in Japanese Unexamined Patent Application Publication No. 2008-257292, a technique for retrieving past medical images similar to a medical image to be read from past cases accumulated in a PACS is being developed, in order to use the past medical images as a reference in reading the medical image to be read.

SUMMARY

However, further improvements are necessary.

One non-limiting and exemplary embodiment achieves further improvements.

In one general aspect, the techniques disclosed here feature a method for controlling an information terminal that includes a touch panel display and that is connected to a case retrieval system that retrieves medical images by referring to a medical image database in which medical images are registered. The method includes displaying a target medical image, which is a medical image to be read selected from among target medical image candidates, on the touch panel display, causing a computer of the information terminal to detect specification information indicating a region of interest in the target medical image, causing the computer of the information terminal to receive, from the case retrieval system, a plurality of similar medical images having a feature quantity of the region of interest and a certain degree of similarity in accordance with the region of interest indicated by the specification information, the plurality of similar medical images each including a corresponding region of interest corresponding to the region of interest, displaying a display screen displaying the plurality of received similar medical images on the touch panel display, the display screen including a display region in which at least some of the plurality of received similar medical images are displayed, displaying, if selection of a first similar medical image from among the at least some of the plurality of received similar medical images displayed in the display region is detected, the first similar medical image across the display region, and displaying, if a swipe operation performed on the first similar medical image is detected, a second similar medical image, which has second highest similarity next to the first similar medical image among the plurality of similar medical images, in the display region such that the corresponding region of interest included in the second similar medical image is located at a certain position in the display region.

According to the present disclosure, further improvements can be achieved.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6A is a diagram illustrating an example of the base screen displayed on the display;

FIG. 7 is an enlarged diagram of a disease list display region;

FIG. 8 is a diagram illustrating a base screen at a time when similar cases have been narrowed down using "mycosis";

FIG. 12 is an enlarged diagram of a distribution list display region;

FIG. 13 is a diagram illustrating the distribution list display region in which a checkbox for "bilateral" has been checked;

FIG. 14B is a diagram illustrating an example of the base screen displayed on the display;

FIG. 15 is a diagram illustrating the display list display region in which a checkbox for "bronchial" has been checked;

FIG. 17 is a diagram illustrating the distribution list display region in which a checkbox for "subpleural" has been checked;

FIG. 19 is a diagram illustrating a data structure of patient information;

FIG. 20 is a diagram illustrating a data structure of test information registered in the patient information illustrated in FIG. 19;

FIG. 22 is a diagram illustrating a data structure of a diagnosis report;

FIG. 23 is a diagram illustrating a data structure of similar case data;

FIG. 27 is a diagram illustrating an example of the display screen for the reading target test list after a test is selected;

FIG. 30 is a diagram illustrating a data structure of a disease list generated in S1300 illustrated in FIG. 29;

FIG. 31 is a diagram illustrating a first display example of the disease list display region;

FIG. 32 is a diagram illustrating a second display example of the disease list display region;

FIG. 33 is a diagram illustrating a third display example of the disease list display region;

FIG. 35 is a diagram illustrating a data structure of a distribution list generated in S1400 illustrated in FIG. 29;

DETAILED DESCRIPTION

Figure 1:
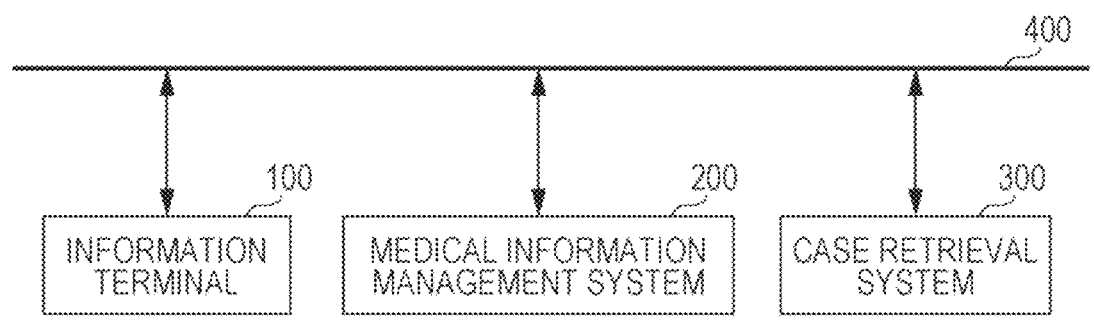
FIG. 1 is a diagram illustrating an overall configuration of a hospital information system adopting an information terminal according to a first embodiment.

Underlying Knowledge Forming Basis of the Present Disclosure

First, a point of observation according to an aspect of the present disclosure will be described.

In Japanese Unexamined Patent Application Publication No. 2008-257292, an image diagnosis support apparatus is disclosed that displays a case image helpful in determining a disease, statistical information relating to the disease, or the like during image diagnosis based on a diagnosis target image. A retrieval result screen of the image diagnosis support apparatus displays the diagnosis target image and information regarding a representative case of each disease. More specifically, the retrieval result screen displays i) images of representative cases of top three diseases A, D, and G, ii) similarity to the diagnosis target image, the number of cases registered, and the number of representative cases for each disease, iii) the number of retrieval results (the total number of diseases found), iv) a software button, such as a "Next Page" button, for referring to information regarding other diseases that are not displayed in a first page, and the like (refer to Paragraphs [0062] and [0063] and FIG. 6E of Japanese Unexamined Patent Application Publication No. 2008-257292).

In Japanese Unexamined Patent Application Publication No. 2008-257292, however, the retrieval result screen (refer to FIG. 6E of Japanese Unexamined Patent Application Publication No. 2008-257292) includes a "Next Page" software button. Therefore, the "Next Page" software button needs to be selected to display a next page of the retrieval result screen and view another representative case of each disease. If the number of retrieval results is large, namely, say, 200 to 300, the software button needs to be operated repeatedly. In addition, the position of a lesion does not necessarily remain the same among a large number of images that a doctor needs to check. Therefore, the doctor needs to visually search for the position of a lesion each time he/she displays a new page. Therefore, in Japanese Unexamined Patent Application Publication No. 2008-257292, there is a problem that a doctor needs to perform troublesome work in order to determine a disease for a patient using a diagnosis target image. Consequently, the doctor might not be able to identify a disease for a patient efficiently and appropriately.

In Akira Oosawa, et al. "Development of "SYNAPSE Case Match", Content-based Image Retrieval System for Supporting Image Diagnosis", a content-based image retrieval system for supporting an image diagnosis given by a doctor is disclosed that instantaneously retrieves necessary information from a clinical database constructed in a PACS or the like and displays the information using a function of retrieving past cases similar to an image of a lesion. More specifically, this system retrieves case images including lesions similar to a lesion included in an inspection image and displays the cases images in order of descending similarity. Thereafter, one of the displayed case images, which are referred to as "reference case images", is selected and displayed along with the inspection image (refer to p. 12 "2.2 Features of This System" and FIG. 3 of "Development of "SYNAPSE Case Match", Content-based Image Retrieval System for Supporting Image Diagnosis").

Figure 3:
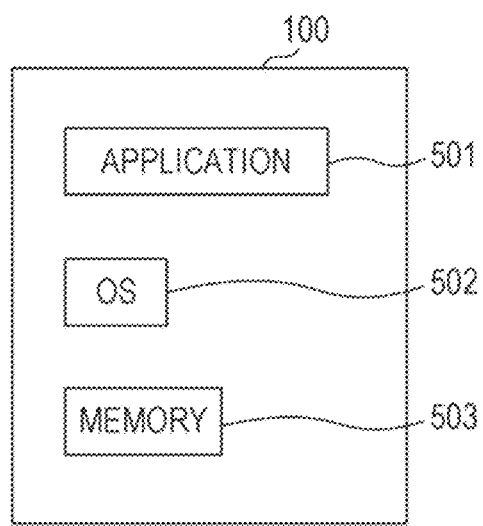
FIG. 3 is a diagram illustrating an example of the configuration of the information terminal in actual implementation.

In the system disclosed in "Development of "SYNAPSE Case Match", Content-based Image Retrieval System for Supporting Image Diagnosis" if the displayed reference case images do not include an image to be selected, next reference case images are to be displayed. As illustrated in FIG. 3 of "Development of "SYNAPSE Case Match", Content-based Image Retrieval System for Supporting Image Diagnosis", however, the size of displayed reference case images is small compared to the size of the entirety of a display screen. In addition, the number of reference case images to be checked by the doctor is large, and the position of a lesion does not necessarily remain the same in each of the large number of case images. Therefore, the doctor needs to visually search for the position of a lesion in each of the small reference case images each time he/she displays next case images. Accordingly, in "Development of "SYNAPSE Case Match", Content-based Image Retrieval System for Supporting Image Diagnosis", there is a problem that a doctor needs to perform troublesome work in order to determine a disease for a patient using an inspection image. Consequently, the doctor might not be able to identify a disease for a patient efficiently and appropriately.

When a lesion, for which a disease has not yet been identified, included in a medical image to be read is examined, it is effective to refer to other medical images in which diseases have already been identified and that are similar to the medical image to be read. If such a system is constructed, however, an enormous number of medical images are registered to a medical image database. It is desirable, even in this case, to effectively present similar medical images, which can be used as a reference when a doctor gives a diagnosis using a medical image to be read, to the doctor.

As a result of the above examination, the following aspects have been conceived.

A first aspect of the present disclosure is a method for controlling an information terminal that includes a touch panel display and that is connected to a case retrieval system that retrieves medical images by referring to a medical image database in which medical images are registered. The method includes displaying a target medical image, which is a medical image to be read selected from among target medical image candidates, on the touch panel display, causing a computer of the information terminal to detect specification information indicating a region of interest in the target medical image, causing the computer of the information terminal to receive, from the case retrieval system, a plurality of similar medical images having a feature quantity of the region of interest and a certain degree of similarity in accordance with the region of interest indicated by the specification information, the plurality of similar medical images each including a corresponding region of interest corresponding to the region of interest, displaying a display screen displaying the plurality of received similar medical images on the touch panel display, the display screen including a display region in which at least some of the plurality of received similar medical images are displayed, displaying, if selection of a first similar medical image from among the at least some of the plurality of received similar medical images displayed in the display region is detected, the first similar medical image across the display region, and displaying, if a swipe operation performed on the first similar medical image is detected, a second similar medical image, which has second highest similarity next to the first similar medical image among the plurality of similar medical images, in the display region such that the corresponding region of interest included in the second similar medical image is located at a certain position in the display region.

A position of the corresponding region of interest might be different in each of the plurality of similar medical images. On the other hand, similar medical images having the certain degree of similarity to the region of interest of the target medical image are received. Therefore, if the position of the corresponding region of interest is different in each of the plurality of similar medical images, a doctor needs to visually search for the corresponding region of interest, which is located at a different position in each of the plurality of similar medical images, after each swipe operation. When the corresponding regions of interest of the plurality of similar medical images are sequentially observed, the doctor might need to spend unnecessary time and effort to find the corresponding regions of interest, which decreases efficiency.

According to this aspect, when the second similar medical image, which has the second highest similarity next to the first similar medical image, is displayed through a swipe operation, the second similar medical image is not simply displayed. The second similar medical image is displayed in the display region such that the corresponding region of interest included in the second similar medical image is located at the certain position in the display region.

Therefore, even when the corresponding regions of interest of the first similar medical image and the second similar medical image are sequentially observed through a swipe operation, the doctor need not visually search for the corresponding region of interest each time the displayed similar medical image is switched. Therefore, the doctor can concentrate on observing the corresponding regions of interest. As a result, when the corresponding regions of interest of the first similar medical image and the second similar medical image are sequentially observed through a swipe operation, the observation can be less exhausting and a reading efficiency improves, thereby improving an efficiency of diagnosis.

In addition, in the first aspect, for example, if a swipe operation performed on the second similar medical image is detected, a third similar medical image, which has third highest similarity next to the second similar medical image among the plurality of similar medical images, may be displayed in the display region such that the corresponding region of interest included in the third similar medical image is located at the certain position in the display region.

According to this aspect, when the second similar medical image and the third similar medical image are sequentially observed through a swipe operation, the corresponding regions of interest are displayed at the certain position. Therefore, the doctor need not visually search for the corresponding region of interest each time the displayed similar medical image is switched.

In addition, in the first aspect, for example, when the first similar medical image is displayed in the display region, the first similar medical image may be displayed in the display region such that the corresponding region of interest included in the first similar medical image is located at the certain position in the display region.

According to this aspect, the first similar medical image, which is the similar medical image displayed first, too, is displayed such that the corresponding region of interest is located at the certain position.

In addition, in the first aspect, for example, the certain position in the display region may include a position corresponding to a center of the display region.

According to this aspect, even if the position of the corresponding region of interest is different between the first similar medical image and the second similar medical image, each corresponding region of interest is not observed, for example, at a corner of the display region. Each corresponding region of interest is displayed at the center of the display region, and regions around each corresponding region of interest can also be observed equally.

In addition, in the first aspect, for example, the certain position in the display region may include a position of the corresponding region of interest included in the first similar medical image in the first similar medical image.

According to this aspect, the position of the corresponding region of interest included in the first similar medical image, which is the similar medical image displayed first, is the certain position. Therefore, the doctor initially looks at the position of the corresponding region of interest included in the first similar medical image, which is the similar medical image displayed first, and can then observe the corresponding region of interest included in the second similar medical image without turning his/her eyes.

In addition, in the first aspect, for example, when the second similar medical image is displayed in the display region such that the corresponding region of interest included in the second similar medical image is located at the certain position in the display region, a portion of the second similar medical image outside the display region need not be displayed and a background image may be displayed in a portion of the display region outside the second similar medical image.

In addition, in the first aspect, for example, if a swipe operation performed on the second similar medical image is not detected for a certain period of time after the second similar medical image is displayed in the display region, a display position of the second similar medical image may be moved from the certain position in the display region, at which the corresponding region of interest included in the second similar medical image has been displayed, to a position at which entirety of the second similar medical image is displayed across the display region.

If a swipe operation stops after being performed, it is likely that the doctor is interested in a similar medical image displayed when the swipe operation has stopped. That is, during the swipe operation, the doctor is browsing through many similar medical images, and when the swipe operation has stopped, it is likely that the doctor is observing a current similar medical image.

According to this aspect, if a swipe operation is not detected for the certain period of time, the display position of the similar medical image displayed when the swipe operation has stopped is moved to the position at which the entirety of the similar medical image is displayed. As a result, the doctor can observe the similar medical image displayed when the swipe operation has stopped in a normal display state. Therefore, during the swipe operation, the doctor can focus upon the corresponding regions of interest, which improves a search efficiency. On the other hand, when the swipe operation has stopped, the doctor can observe all information included in a displayed similar medical image, which improves an accuracy of diagnosis. In addition, just by stopping the swipe operation, the normal display state is established. Therefore, the doctor need not perform a special operation for returning to the normal display state, which improves an efficiency of operation.

In addition, in the first aspect, for example, the method may cause the computer of the information terminal to transmit information indicating the feature quantity of the region of interest to the case retrieval system and to receive, from the case retrieval system, similar medical images having the feature quantity of the region of interest and the certain degree of similarity.

In addition, in the first aspect, for example, the method may cause the computer of the information terminal to transmit the target medical image and the specification information indicating the region of interest to the case retrieval system and to receive, from the case retrieval system, similar medical images having the feature quantity of the region of interest and the certain degree of similarity obtained from the target medical image and the specification information.

A second aspect of the present disclosure is a method for controlling an information terminal that includes a touch panel display and that is connected to a case retrieval system that retrieves medical images by referring to a medical image database in which medical images are registered. The method includes displaying a target medical image, which is a medical image to be read selected from among target medical image candidates, on the touch panel display, causing a computer of the information terminal to detect specification information indicating a region of interest in the target medical image, causing the computer of the information terminal to receive, from the case retrieval system, a plurality of similar medical images having a feature quantity of the region of interest and a certain degree of similarity in accordance with the region of interest indicated by the specification information, the plurality of similar medical images each including a corresponding region of interest corresponding to the region of interest, displaying a display screen displaying the plurality of received similar medical images on the touch panel display, the display screen including a display region in which at least some of the plurality of received similar medical images are displayed, displaying, if selection of a first similar medical image from among the at least some of the plurality of received similar medical images displayed in the display region is detected, the first similar medical image across the display region, enlarging, if an enlargement operation performed on the first similar medical image displayed across the display region is detected, the first similar medical image while moving the corresponding region of interest included in the first similar medical image to a position corresponding to a center of the display region, and enlarging, if a swipe operation performed on the enlarged first similar medical image is detected, a second similar medical image, which has second highest similarity next to the first similar medical image among the plurality of similar medical images, while moving the corresponding region of interest included in the second similar medical image to the center of the display region and matching a display size of the corresponding region of interest included in the second similar medical image with a display size of the corresponding region of interest included in the first similar medical image and displays the second similar medical image in the display region.

A position of the corresponding region of interest might be different in each of the plurality of similar medical images. On the other hand, similar medical images having the certain degree of similarity to the region of interest of the target medical image are received. Therefore, if the position of the corresponding region of interest is different in each of the plurality of similar medical images, a doctor needs to visually search for the corresponding region of interest, which is located at a different position in each of the plurality of similar medical images, after each swipe operation. When the corresponding regions of interest of the plurality of similar medical images are sequentially observed, the doctor might need to spend unnecessary time and effort to find the corresponding regions of interest, which decreases efficiency.

According to this aspect, when the second similar medical image, which has the second highest similarity next to the first similar medical image, is displayed through a swipe operation, the second similar medical image is not simply displayed. The second similar medical image is displayed in the display region such that the corresponding region of interest included in the second similar medical image is located at the certain position in the display region.

Therefore, even when the corresponding regions of interest of the first similar medical image and the second similar medical image are sequentially observed through a swipe operation, the doctor need not visually search for the corresponding region of interest each time the displayed similar medical image is switched. Therefore, the doctor can concentrate on observing the corresponding regions of interest. As a result, when the corresponding regions of interest of the first similar medical image and the second similar medical image are sequentially observed through a swipe operation, the observation can be less exhausting and the reading efficiency improves, thereby improving the efficiency of diagnosis.

In addition, not only the position of the correspond region of interest but also the size of the corresponding region of interest might be different in each of the plurality of similar medical images. Therefore, even if the position of each corresponding region of interest is the same, the doctor needs to look at the second similar medical image more closely if the corresponding region of interest included in the second similar medical image is smaller than that included in the first similar medical image. In addition, when the corresponding regions of interest of the plurality of similar medical images are sequentially observed, the sizes of the corresponding regions of interest are different from each other. Therefore, the doctor might need to spend unnecessary time and effort to find the corresponding regions of interest, which decreases the reading efficiency.

According to this aspect, the first similar medical image is enlarged and displayed such that the corresponding region of interest included in the first similar medical image is located at the center of the display region. If a swipe operation performed on the first similar medical image is detected in this state, the second similar medical image, which has the second highest similarity next to the first similar medical image among the plurality of similar medical images, is enlarged while moving the corresponding region of interest included in the second similar medical image to the center of the display region and matching the display size of the corresponding region of interest included in the second similar medical image with the display size of the corresponding region of interest included in the first similar medical image and displayed in the display region.

Therefore, even when the corresponding regions of interest of the first similar medical image and the second similar medical image are sequentially observed through a swipe operation, the doctor need not visually search for the corresponding region of interest each time the displayed similar medical image is switched. In addition, the doctor can observe the corresponding regions of interest of the same size. As a result, when the corresponding regions of interest of the first similar medical image and the second similar medical image are sequentially observed through a swipe operation, the observation can be less exhausting and the reading efficiency improves, thereby improving the efficiency of diagnosis.

In addition, in the second aspect, for example, if a swipe operation performed on the second similar medical image is detected, a third similar medical image, which has third highest similarity among the plurality of similar medical images, may be enlarged while moving the corresponding region of interest included in the third similar medical image to the center of the display region and matching a display size of the corresponding region of interest included in the third similar medical image with the display size of the corresponding region of interest included in the first similar medical image and displayed in the display region.

According to this aspect, when the second similar medical image and the third similar medical image are sequentially observed through a swipe operation, the corresponding regions of interest of the second similar medical image and the third similar medical image can be displayed such that the corresponding regions of interest are located at the center of the display region and have the same display size.

Therefore, even when the corresponding regions of interest of the second similar medical image and the third similar medical image are sequentially observed through a swipe operation, the doctor need not visually search for the corresponding region of interest each time the displayed similar medical image is switched. In addition, the doctor can observe the corresponding regions of interest of the same size. As a result, when the corresponding regions of interest of the second similar medical image and the third similar medical image are sequentially observed through a swipe operation, the observation can be less exhausting and the reading efficiency improves, thereby improving the efficiency of diagnosis.

In addition, in the second aspect, for example, the method may cause the computer of the information terminal to transmit information indicating the feature quantity of the region of interest to the case retrieval system and to receive, from the case retrieval system, similar medical images having the feature quantity of the region of interest and the certain degree of similarity.

In addition, in the second aspect, for example, the method may cause the computer of the information terminal to transmit the target medical image and the specification information indicating the region of interest to the case retrieval system and to receive, from the case retrieval system, similar medical images having the feature quantity of the region of interest and the certain degree of similarity obtained from the target medical image and the specification information.

Another aspect of the present disclosure is a control method including displaying a first resulting image in a first display region of a touch panel display instead of a plurality of images including a first image and a second image, the first resulting image being obtained by enlarging a third image included in a first region of the first image, and displaying, if the first resulting image is swiped, a second resulting image in the first display region instead of the first resulting image, the second resulting image being obtained by enlarging a fourth image included in a second region of the second image. The plurality of images and a plurality of predetermined region are in a one-to-one relationship. Each of the plurality of images includes a predetermined corresponding region included in the plurality of predetermined regions. The first region includes a first predetermined region included in the plurality of predetermined regions. The third image includes a fifth image included in the first predetermined region. The second region includes a second predetermined region included in the plurality of predetermined regions. The fourth image includes a sixth image included in the second predetermined region. Among images included in the plurality of predetermined regions, a most similar image to a predetermined image is the fifth image. Among the images included in the plurality of predetermined regions, a second most similar image to the predetermined image is the sixth image. If the first resulting image is displayed in the first display region, the first predetermined region is displayed at a center of the first display region. If the second resulting image is displayed in the first display region, the second predetermined region is displayed at the center of the first display region.

First Embodiment

An embodiment of the present disclosure will be described hereinafter with reference to the drawings. In the drawings, the same components are given the same reference numerals.

FIG. 1 is a diagram illustrating an overall configuration of a hospital information system adopting an information terminal according to this embodiment. As illustrated in FIG. 1, the hospital information system includes an information terminal 100, a medical information management system 200, and a case retrieval system 300.

The information terminal 100, the medical information management system 200, and the case retrieval system 300 are communicably connected to one another through a network 400.

The medical information management system 200 and the case retrieval system 300 need not necessarily be installed in a hospital, but may be software operating on a data center, a private cloud server, a public cloud server, or the like outside the hospital. If the medical information management system 200 and the case retrieval system 300 are installed in the hospital, the network 400 may be a local area network (LAN). The LAN may be a wired LAN of an Institute of Electrical and Electronics Engineers (IEEE) 802.3 series, a wireless LAN of an IEEE 802.11 series, or a network including both types of LAN. If the medical information management system 200 and the case retrieval system 300 are realized using a server outside the hospital, the network 400 may be the Internet.

The information terminal 100 may be an information terminal such as a personal computer (PC) or a tablet terminal. The medical information management system 200 may be a PACS, an electronic medical record system, or the like.

Figure 2:
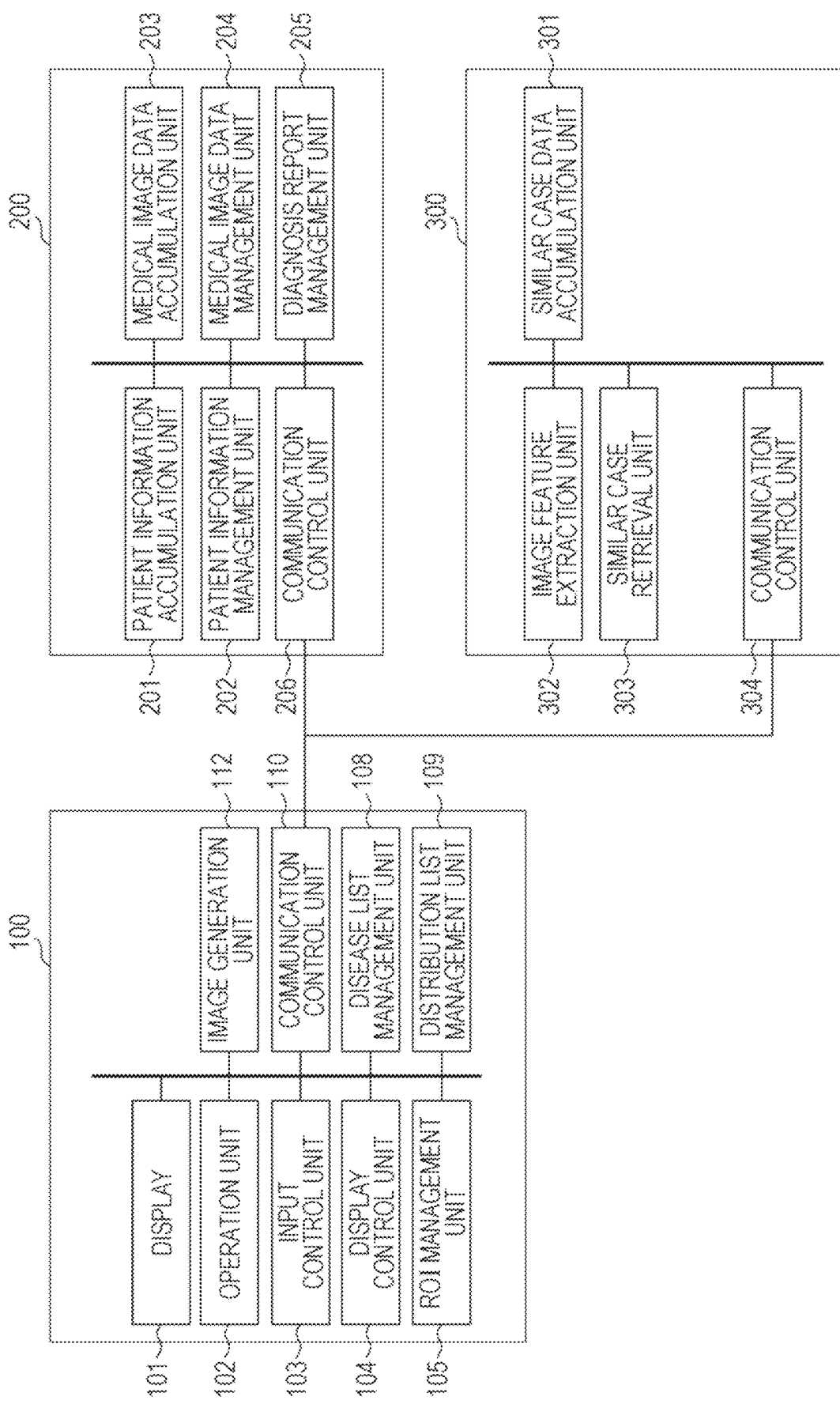
FIG. 2 is a block diagram illustrating configurations of the information terminal, a medical information management system, and a case retrieval system.

FIG. 2 is a block diagram illustrating configurations of the information terminal 100, the medical information management system 200, and the case retrieval system 300. As illustrated in FIG. 2, the information terminal 100 includes a display 101, an operation unit 102, an input control unit 103, a display control unit 104, a region of interest (ROI) management unit 105, a disease list management unit 108, a distribution list management unit 109, a communication control unit 110, and an image generation unit 112.

The display 101 is, for example, a liquid crystal monitor including a touch panel and displays a medical image used for diagnosis and a medical record image along with a report input screen for inputting a diagnosis and the like.

The operation unit 102 is, for example, a touch panel and receives various operations performed by a user on the information terminal 100. For example, the operation unit 102 receives an operation performed by the user on a medical image or a medical record image displayed on the display 101, an operation for inputting a diagnosis in the report input screen, and the like.

The input control unit 103 detects an operation performed by the user on the operation unit 102. The input control unit 103 then interprets the operation and transmits a result of the operation to another component. For example, the input control unit 103 receives, from the operation unit 102, data regarding coordinates of a position at which an object (for example, the user's finger) has touched the touch panel. The input control unit 103 then compares the data with coordinates of graphical user interfaces (GUIs) generated by the display control unit 104, in order to determine whether, among the GUIs, a button object has been selected. The input control unit 103 transmits a result of the operation performed by the user to another component.

The display control unit 104 generates GUIs of the information terminal 100 and displays the GUIs on the display 101.

The ROI management unit 105 generates, before retrieval of similar cases, ROI information indicating a ROI set in a retrieval query image, which will be described later, and stores the ROI information in a memory, in order to manage the ROI information.

The disease list management unit 108 generates a disease list (FIG. 30) of similar cases displayed in a case display region 710 (FIG. 5) and stores the disease list in the memory, in order to manage the disease list.

The distribution list management unit 109 generates a distribution list (FIG. 35) indicating the lesion distribution of the similar cases displayed in the case display region 710 and stores the distribution list in the memory, in order to manage the distribution list.

The communication control unit 110 includes, for example, a communication device for connecting the information terminal 100 to the network 400 and controls communication between the information terminal 100 and the medical information management system 200 and between the information terminal 100 and the case retrieval system 300. In addition, the communication control unit 110 receives requests to transmit various pieces of data from other blocks and transmits the various pieces of data to the medical information management system 200 or the case retrieval system 300. The communication control unit 110 also receives data transmitted from the medical information management system 200 or the case retrieval system 300 and transfers the data to appropriate blocks.

The image generation unit 112 obtains thumbnail images of similar cases created in advance. The image generation unit 112 generates thumbnail images whose display regions on the display 101 have been changed in accordance with an operation performed by the user and outputs the generated thumbnail images to the display control unit 104.

The image generation unit 112 obtains, from the input control unit 103, a result of an operation performed by the user on the operation unit 102. The image generation unit 112 receives similar case data (similarity and ROI information) from a similar case retrieval unit 303 through the communication control unit 110. If the user performs a swipe operation, the image generation unit 112 generates a thumbnail image of a similar case such that center coordinates of a ROI of the thumbnail image is located at a center position of a display regions in which the thumbnail image is displayed. The generation of a thumbnail image based on a swipe operation will be described in detail later.

As illustrated in FIG. 2, the medical information management system 200 includes a patient information accumulation unit 201, a patient information management unit 202, a medical image data accumulation unit 203, a medical image data management unit 204, a diagnosis report management unit 205, and a communication control unit 206.

The patient information accumulation unit 201 accumulates patient information 1000 (FIG. 19) in which personal information such as the gender and age of each patient, clinical information such as past medical histories, and test information regarding a blood test or the like are registered.

The patient information management unit 202 performs a process for updating the patient information 1000 (FIG. 19) accumulated in the patient information accumulation unit 201 by registering data input from the user, a process for outputting the patient information 1000 to the display control unit 104, and the like, in order to manage the patient information 1000. The medical image data accumulation unit 203 accumulates medical image data, which includes test images of patients.

The medical image data management unit 204 accumulates the medical image data in the medical image data accumulation unit 203 in order to manage the medical image data.

The diagnosis report management unit 205 manages a diagnosis report 3000 (FIG. 22) indicating diagnoses given by doctors as a result of various medical tests conducted on patients.

The communication control unit 206 includes, for example, a communication device for connecting the medical information management system 200 to the network 400. The communication control unit 206 receives requests to transmit various pieces of data from other blocks and transmits the various pieces of data to the information terminal 100 or the case retrieval system 300. The communication control unit 206 also receives data transmitted from the information terminal 100 or the case retrieval system 300 and transfers the data to appropriate blocks.

As illustrated in FIG. 2, the case retrieval system 300 includes a similar case data accumulation unit 301, an image feature extraction unit 302, and a similar case retrieval unit 303.

The similar case data accumulation unit 301 accumulates similar case data 4000 (FIG. 23) in which, among the similar cases managed by the medical information management system 200, image features extracted from a large number of similar cases selected as data to be retrieved as similar cases, generated thumbnail images, and the like are registered.

The image feature extraction unit 302 extracts an image feature included in ROI information regarding a retrieval query image transmitted from the communication control unit 110 of the information terminal 100.

The ROI information is an example of specification information indicating a ROI.

The similar case retrieval unit 303 generates results of retrieval of similar cases by comparing the image feature extracted by the image feature extraction unit 302 with image features of one or more similar cases accumulated in the similar case data accumulation unit 301.

A communication control unit 304 includes, for example, a communication device for connecting the case retrieval system 300 to the network 400. The communication control unit 304 receives requests to transmit various pieces of data from other blocks and transmits the various pieces of data to the information terminal 100 or the medical information management system 200. The communication control unit 304 also receives data transmitted from the information terminal 100 or the medical information management system 200 and transfers the data to appropriate blocks.

FIG. 3 is a diagram illustrating an example of the configuration of the information terminal 100 in actual implementation. As illustrated in FIG. 3, the information terminal 100 includes applications 501, an operating system (OS) 502, a memory 503, and other pieces of hardware that are not illustrated.

The applications 501 are application software for causing a PC or a tablet terminal to function as the information terminal 100 and executed by a processor of the information terminal 100. The applications 501 may be installed in the information terminal 100 by reading the applications 501 from a computer-readable recording medium or downloading the applications 501 from the network 400.

Here, the applications 501 include a medical information management application and a similar case retrieval application. The medical information management application is an application for enabling the information terminal 100 to cooperate with the medical information management system 200. The similar case retrieval application is an application for enabling the information terminal 100 to cooperate with the case retrieval system 300. Both applications communicate data with each other in order to integrate services provided by the medical information management system 200 and services provided by the case retrieval system 300 with each other in the information terminal 100.

The OS 502 is basic software of the information terminal 100 and executed by the processor of the information terminal 100. The memory 503 may be a storage device such as random-access memory (RAM) or a read-only memory (ROM) included in the information terminal 100 and stores datasets included in the applications 501.

By executing the applications 501 using the processor of the information terminal 100, the functions of the input control unit 103, the display control unit 104, the ROI management unit 105, the disease list management unit 108, the distribution list management unit 109, the communication control unit 110, and the image generation unit 112 are realized.

In this embodiment, however, only the applications 501 may be installed in the information terminal 100, or the applications 501 and the OS 502 may be installed. Alternatively, the applications 501, the OS 502, and the memory 503 may be installed in the information terminal 100, or the applications 501, the OS 502, the memory 503, and the other pieces of hardware that are not illustrated may be installed. In any case, the information terminal 100 according to this embodiment can be realized.

Figure 4:
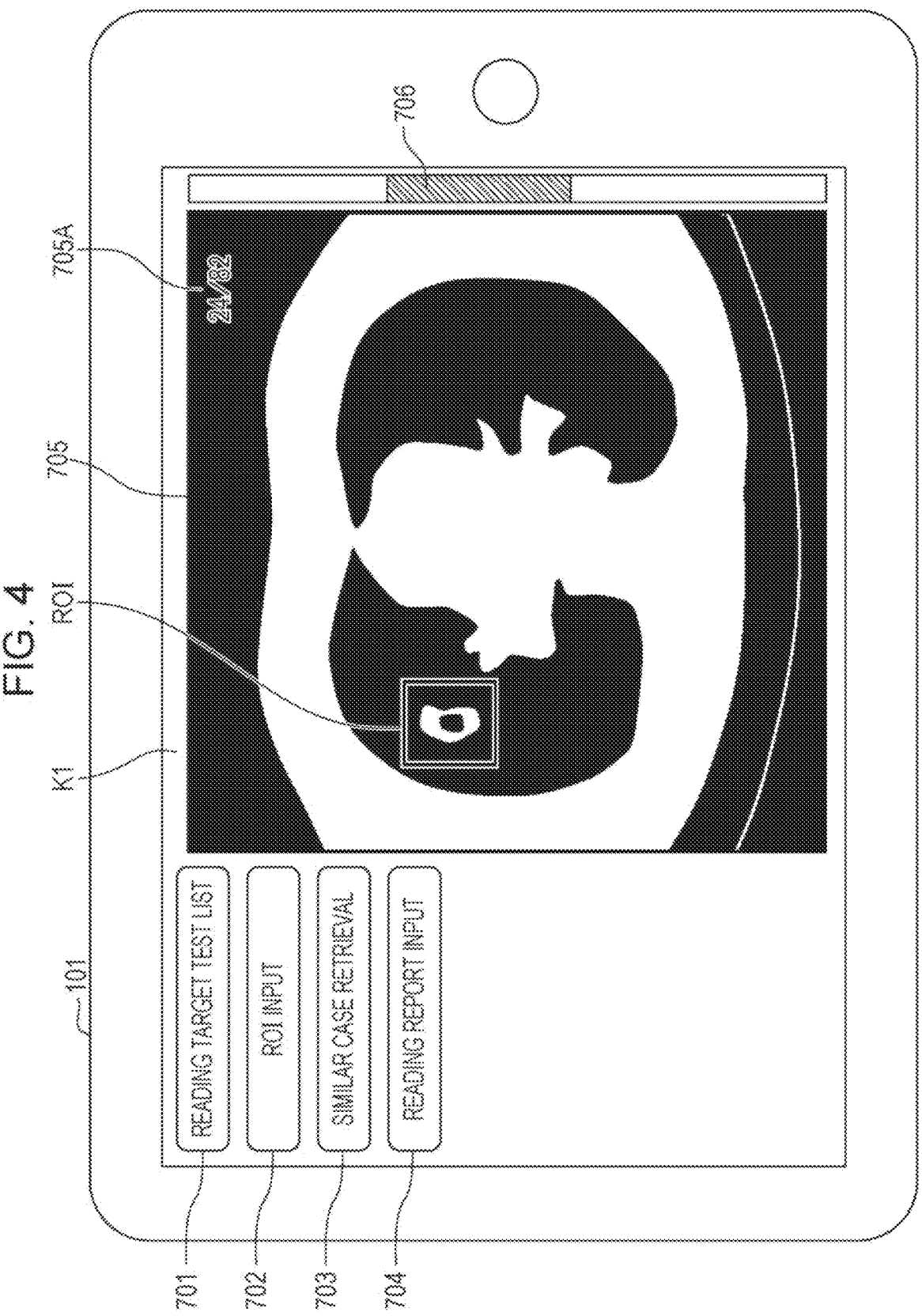
FIG. 4 is a diagram illustrating an example of a display screen displayed on a display at a time when a doctor views a diagnosis image using the information terminal.

FIG. 4 is a diagram illustrating an example of a display screen K1 displayed on the display 101 when a doctor views a diagnosis image using the information terminal 100. As illustrated in FIG. 4, a base screen of the information terminal 100 displayed on the display 101 includes a medical image viewer 705, a reading target test list button 701, a ROI input button 702, a similar case retrieval button 703, a reading report input button 704, and a scroll bar 706.

Medical images are normally recorded in a DICOM format. The medical image viewer 705 is a viewer capable of handling the DICOM format. It is assumed in this embodiment that medical images are chest CT images, which are a large number of tomograms (hereinafter also referred to as "slice images"). However, this is an example, and CT images of another part of a body (for example, head, abdomen, leg, or arm) may be adopted.

If the user performs an operation on the touch panel, another slice image is displayed on the medical image viewer 705 as a chest CT image. Here, among the chest CT images arranged on the touch panel, for example, first slice images indicate the neck, and last slice images indicate the abdomen.

As medical images, MRI images or plain roentgenograms may be adopted instead of chest CT images. Although the number of medical images displayed on the medical image viewer 705 is 1 in the example illustrated in FIG. 4, this is just an example. Another number of medical images, such as 2 or 4, may be displayed. If the number of medical images displayed on the medical image viewer 705 is large, the number of medical images that can be compared with one another at once is large, but the area of each image becomes small. Therefore, the number of medical images displayed may vary in accordance with the display size of the display 101. The user or a manager may arbitrarily change the number of medical images displayed.

Before the similar case retrieval application is activated, the medical image viewer 705 displays a chest CT image of a certain patient used for activating retrieval of similar cases. In particular, an image (that is, a retrieval query image) at a slice position when a reader activates the retrieval of similar cases is displayed as a chest CT image. The display control unit 104 may superimpose, upon the retrieval query image, a ROI with which the retrieval of similar cases is performed. The retrieval query image is an example of a target medical image, which is a medical image to be read.

The reading target test list button 701 is a button for switching the display screen of the display 101 from the display screen K1 for a diagnosis image illustrated in FIG. 4 to a display screen K5 (illustrated in FIG. 26, which will be referred to later) for a reading target test list from which a reading target is selected.

The ROI input button 702 is a button for, before the doctor retrieves similar cases, establishing a state in which a ROI can be input to the retrieval query image displayed on the medical image viewer 705. By inputting coordinates on the touch panel after tapping the ROI input button 702, the doctor can input the ROI illustrated in FIG. 4.

The similar case retrieval button 703 is a button for activating the similar case retrieval application. By tapping the similar case retrieval button 703 after inputting a ROI, the user can activate the similar case retrieval application.

The reading report input button 704 is a button for switching the display screen from the display screen K1 for a diagnosis image illustrated in FIG. 4 to a creation screen for creating the diagnosis report 3000 (illustrated in FIG. 22, which will be referred to later).

The reading target test list button 701, the ROI input button 702, the similar case retrieval button 703, and the reading report input button 704 are examples. The same operations as described above may be performed using any input method other than that in which the buttons are used, instead.

The scroll bar 706 is used for switching the medical image displayed on the medical image viewer 705 to another slice image. The display control unit 104 displays a slice image located at a position corresponding to a position of the scroll bar 706.

For example, if the user touches the scroll bar 706 with an object (for example, the user's finger) and moves the object in contact with the scroll bar 706 upward or downward, the input control unit 103 detects the touch and the movement. The display control unit 104 moves, in accordance with the movement of the object, a displayed position of the scroll bar 706. In addition, the display control unit 104 switches the slice image displayed on the medical image viewer 705 to a slice image located at a position corresponding to the position of the scroll bar 706.

"24/82" is displayed in a slice position display portion 705A illustrated in FIG. 4. This means that a medical image displayed on the medical image viewer 705 illustrated in FIG. 4 is a 24th slice image among a total of 82 slice images.

Figure 5:
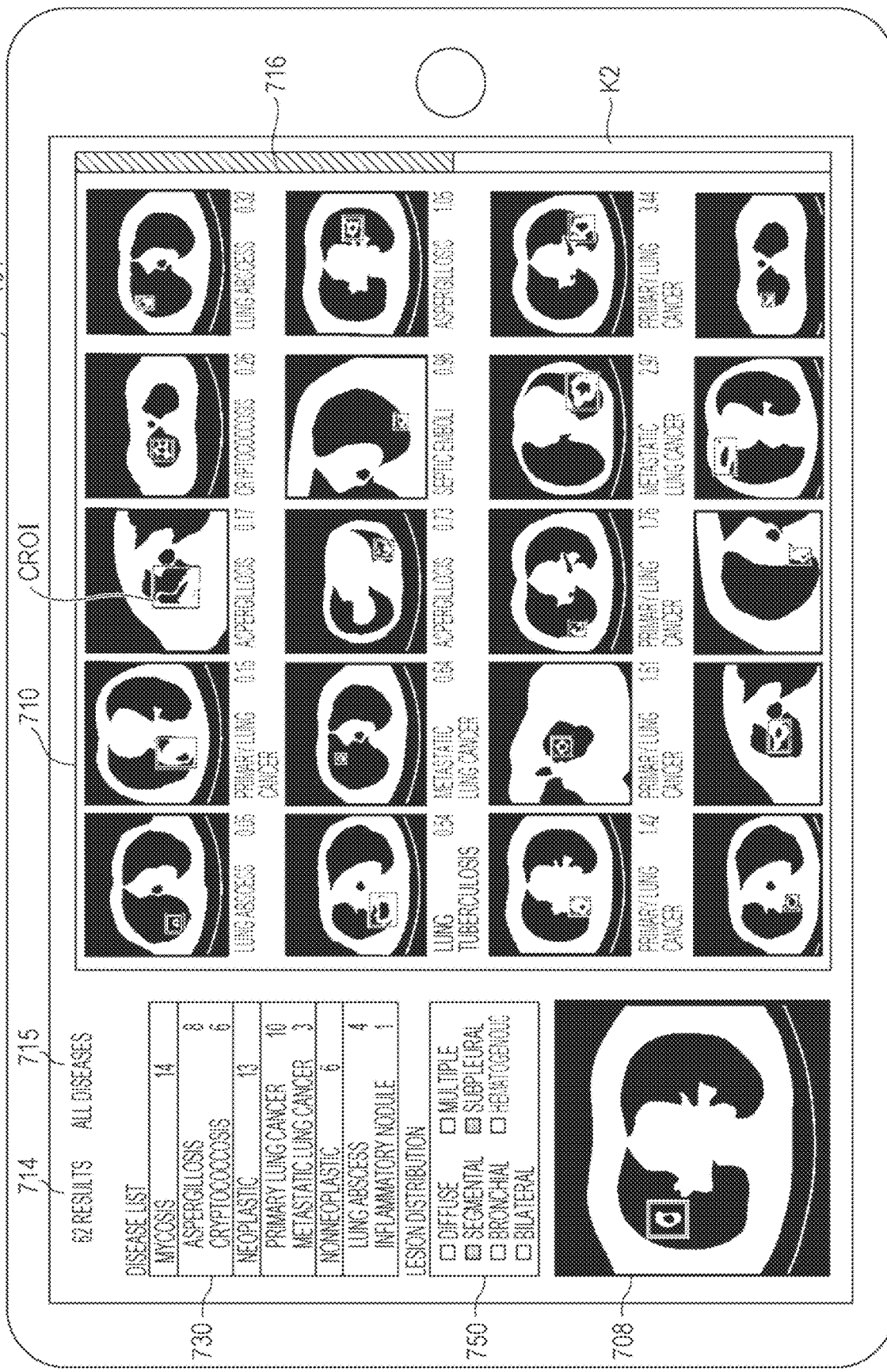
FIG. 5 is a diagram illustrating an example of a base screen displayed on the display.

FIG. 5 is a diagram illustrating an example of a base screen K2 displayed on the display 101 after the information terminal 100 activates the similar case retrieval application. As illustrated in FIG. 5, after the similar case retrieval application is activated, the display screen K1 (FIG. 4) for a medical image during diagnosis (a target medical image, which is a medical image to be read) switches to the base screen K2 displaying thumbnail images of similar cases. As illustrated in FIG. 5, the base screen K2 (an example of a display screen) displayed on the display 101 includes a target display region 708, a case display region 710 (an example of a display region), a disease list display region 730, and a distribution list display region 750.

The target display region 708 is a region in which a retrieval query image (target medical image) used for retrieving similar cases is displayed.

The case display region 710 is a region in which thumbnail images of cases similar to the retrieval query image are displayed in order of descending similarity. Here, the thumbnail images of the similar cases are an example of similar medical images.

For example, it is likely that the display 101 including the touch panel, such as a tablet, does not have a large display region. In this case, if thumbnail images of a large number of similar cases are displayed, the size of each thumbnail image becomes small, thereby making it difficult to view the similar cases. Therefore, in a base screen K3, the case display region 710 includes only one thumbnail image of a similar case that is most similar to the retrieval query image as illustrated in FIG. 6A (referred to later).

The case display region 710 displays images obtained by converting the resolution and pixel values of DICOM images. Since a large number of similar cases are displayed in the case display region 710, it takes time to complete processing if the conversion of resolution and pixel values is performed each time the similar cases are displayed. Therefore, thumbnail images in an initial screen are created from original DICOM images in advance and saved in the case retrieval system 300.

The conversion of resolution and pixel values will be briefly described hereinafter. Whereas the resolution of an original CT image (slice image) is 512×512 pixels, the resolution of a thumbnail image is lower. Therefore, resolution needs to be converted. A thumbnail image is generated by performing a low-resolution process and a tone conversion process on an original CT image (slice image).

The tone conversion process is performed as follows. In a DICOM image (slice image) obtained as a result of CT, each pixel value (CT value) is a value indicating one of 2,000 tones, namely −1,000 to +1,000 (in Hounsfield units (HUs)). Therefore, it is difficult to display the DICOM image on a common 8-bit grayscale display. Even if the DICOM image can be displayed, it is difficult for a person to visually distinguish an emphysema region (CT value: −1,000 HU), ordinary tissues in a lung field (CT value: about −900 HU), a frosted glass region (CT value: −800 HU), soft tissues (CT value: −100 to −50 HU), water (CT value: 0 HU), and bone (CT value: 1,000 HU) from one another in 2,000 tones.

Therefore, in a slice image, a window level and a window width are usually set for each pixel value in order to reconfigure and display each pixel value as an 8-bit pixel value. Here, the window level refers to a CT value as the center of a window, and the window width refers to a width from the center of the window.

For example, if a DICOM image is reconfigured under a lung field condition, the window level is set to −550 to −800 and the window width is set to 1,000 to 1,600. Therefore, the pixel values of an original slice image are reduced to the 8-bit pixel values of a resultant thumbnail image through the above-described process.

The thumbnail images displayed in the case display region 710 of the base screen K2 (FIG. 5) are thumbnail images indicating similar cases whose distances to a feature vector of a diagnosis target case are shorter than or equal to a certain threshold. In the base screen K3 (FIG. 6A, which will be referred to later), the thumbnail image displayed in the case display region 710 is a thumbnail image indicating a similar case whose a distance to the feature vector of the diagnosis target case is the smallest. Here, for example, Euclidean distance is used as distance. Alternatively, another distance scale such as city block distance may be adopted as distance. The shorter the distance is, the more similar the two images are to each other. As the feature vector, not one obtained from a thumbnail image but one obtained from an original DICOM image is used.

In FIG. 5, for example, in an upper-right portion of the base screen K2, a retrieval result number display region 714 is provided. The retrieval result number display region 714 displays the number of cases similar to a diagnosis target case obtained from the case retrieval system 300 as a result of a retrieval process.

If the number of similar cases is large, it is difficult for the case display region 710 to display all the similar cases at once. Therefore, a vertically long scroll bar 716 is provided, for example, to the right of the case display region 710. The display control unit 104 displays upper or lower thumbnail images included in the case display region 710 in accordance with the amount of movement of the scroll bar 716. As a result, the user can display similar cases that have not been displayed in the case display region 710 and observe such similar cases.

Alternatively, the scroll bar 716 may be horizontally long. In this case, the display control unit 104 displays left or right thumbnail images displayed in the case display region 710 in accordance with the amount of movement of the scroll bar 716.

Although it is assumed that the information terminal 100 obtains thumbnail images whose distances to a retrieval query image are shorter than or equal to a certain threshold from the case retrieval system 300, this is just an example. For example, the information terminal 100 may always obtain a certain number of thumbnail images from the case retrieval system 300 in order of descending similarity, instead. Alternatively, the information terminal 100 may always obtain thumbnail images from the case retrieval system 300 such that a certain number of thumbnail images of a certain confirmed disease are included.

As a method for displaying thumbnail images in the case display region 710, for example, a display method may be adopted in which thumbnail images are displayed from left to right in order of ascending distance, with a thumbnail image whose a distance to a retrieval query image is the shortest displayed at a leftmost position in a first row, and when the first row no longer has space for another thumbnail image, a next thumbnail image is displayed at a leftmost position in a second row. That is, in the case display region 710, a display method may be adopted in which thumbnail images are displayed in order of ascending distance from an upper left portion to a lower right portion.

Another display method may obviously be adopted in this embodiment. For example, a display method may be adopted in which thumbnail images are displayed from top to bottom in order of ascending distance, with a thumbnail image whose distance to a retrieval query image is the shortest displayed at an uppermost position in a first column, and when the first column no longer has space for another thumbnail image, a next thumbnail image is displayed at an uppermost position in a second column. Alternatively, a configuration in which the user can switch between these display methods may be adopted.

Although a distance to a feature vector is adopted as distance in the above example, a distance to a feature quantity may be adopted, instead. Although distance is adopted as similarity in the above example, any measure may be adopted insofar as the measure indicates similarity between images, such as cosine similarity. If cosine similarity is adopted, two images are more similar to each other as a value becomes closer to 1.

The similar cases displayed in the case display region 710 may be narrowed down on the basis of a disease displayed in the disease list display region 730 or a type of lesion distribution displayed in the distribution list display region 750, details of which will be described later. Current retrieval conditions of similar cases are displayed in a display condition display region 715. The example illustrated in FIG. 5 illustrates a state immediately after retrieval of similar cases, that is, thumbnail images have not been narrowed down. Therefore, the display condition display region 715 displays "all diseases".

FIG. 6A is a diagram illustrating an example of the base screen K3 displayed on the display 101. For example, if the user selects a thumbnail image by double-tapping the thumbnail image with an object (for example, the user's finger) in the base screen K2 illustrated in FIG. 5, the input control unit 103 detects the selection. The display control unit 104 displays, as illustrated in FIG. 6A, the base screen K3 in which the selected thumbnail image is displayed across the case display region 710 on the display 101.

In a lower part of the case display region 710 illustrated in FIG. 6A, a confirmed diagnosis display region 711, a distance display region 712, and a similarity ranking display region 713 are provided. In the confirmed diagnosis display region 711, a confirmed diagnosis of a target similar case is displayed. The confirmed diagnosis refers to a disease confirmed through a diagnosis in a target similar case. In the distance display region 712, a distance between a feature vector of a slice image in the target similar case and a feature vector of a retrieval query image is displayed. In the similarity ranking display region 713, a ranking of the target similar case in terms of similarity to the retrieval query image is displayed.

In the example illustrated in FIG. 6A, "lung abscess" displayed in the confirmed diagnosis display region 711 means that the thumbnail image is a thumbnail image indicating a similar case in which a diagnosis of lung abscess is confirmed. "0.05" displayed in the distance display region 712 means that the distance between the slice image of the similar case and the retrieval query image is 0.05. "1/62" displayed in the similarity ranking display region 713 means that the thumbnail image of the similar case is a most similar image to the retrieval query image among thumbnail images of 62 similar cases. That is, the example illustrated in FIG. 6A indicates that the user has selected a thumbnail image in a first row and a first column in the base screen K2 illustrated in FIG. 5.

As illustrated in FIG. 6A, the thumbnail image displayed in the case display region 710 includes a corresponding ROI (CROI). The CROI is a region (that is, a region similar to the ROI) corresponding to the ROI (FIG. 4) set in the retrieval query image (the medical image to be read). In the following description, the CROI will also be simply referred to as a "ROI".

In an upper part of the case display region 710 illustrated in FIG. 6A, a scroll bar 707 is provided. By performing a swipe operation, the similar case displayed in the case display region 710 can be changed to another similar case. The switching of a similar case through a swipe operation will be described in detail later.

The scroll bar 707 indicates a position of the similarity of the similar case displayed in the case display region 710 among all the retrieved similar cases. In the example illustrated in FIG. 6A, as indicated by "1/62" displayed in the similarity ranking display region 713, the similar case having the highest similarity is displayed in the case display region 710. Therefore, the scroll bar 707 is located at a leftmost position thereof.

In the base screen K3 illustrated in FIG. 6A, for example, if the user selects the thumbnail image displayed in the case display region 710 by tapping the thumbnail image with an object, the input control unit 103 detects the selection. The display control unit 104 displays the base screen K2 illustrated in FIG. 2 on the display 101.

Figure 6B:
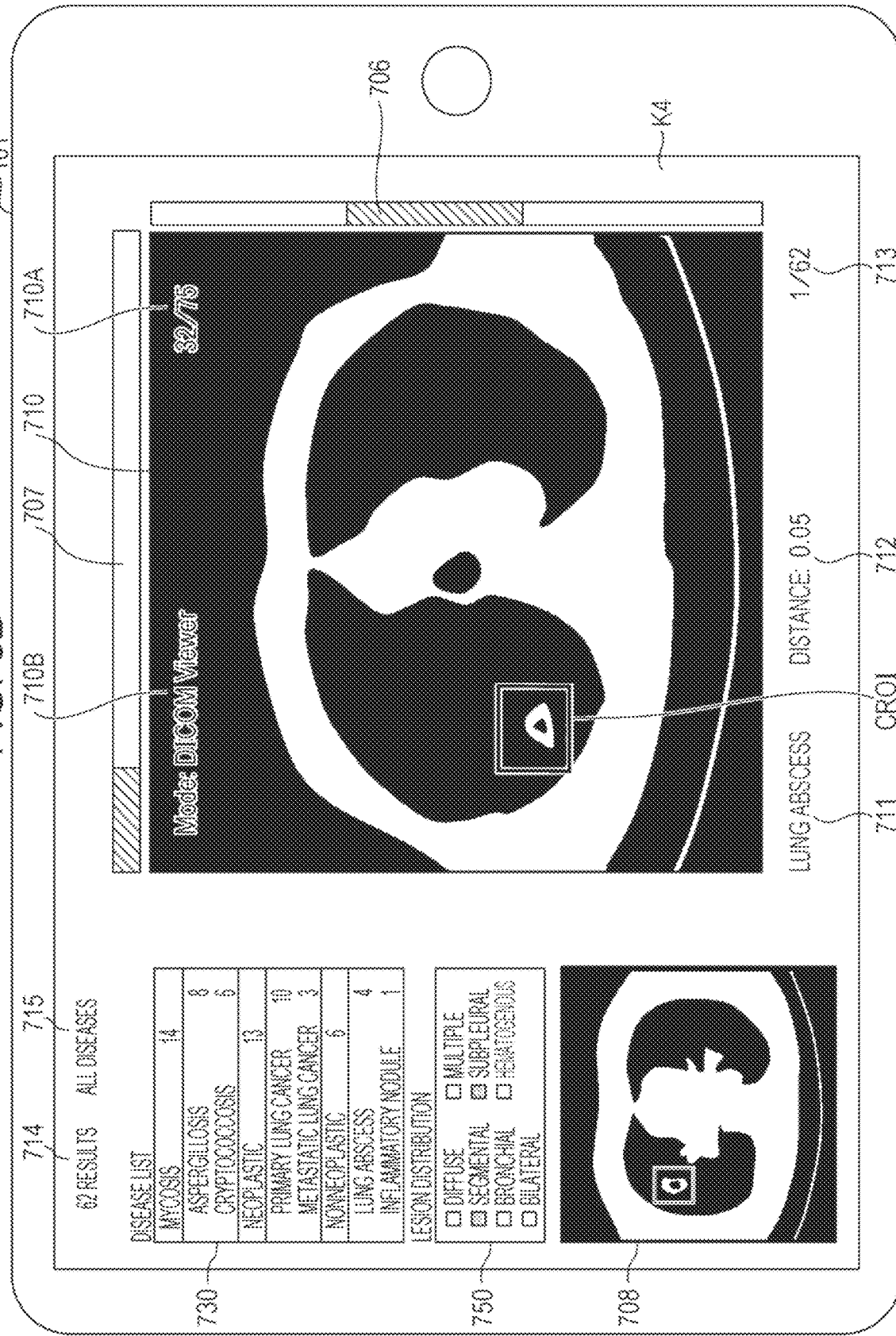
FIG. 6B is a diagram illustrating an example of the base screen in a digital imaging and communications in medicine (DICOM) viewer mode.

FIG. 6B is a diagram illustrating an example of a base screen K4 in a DICOM viewer mode. In the base screen K3 illustrated in FIG. 6A, for example, if the user selects the thumbnail image displayed in the case display region 710 by double-tapping the thumbnail image with an object, the input control unit 103 detects the selection. The display control unit 104 displays, as illustrated in FIG. 6B, the base screen K4 in the DICOM viewer mode on the display 101.

As illustrated in FIG. 6B, in an upper part of a thumbnail image displayed in the case display region 710, a slice number display region 710A and a mode display region 710B are provided. In addition, the scroll bar 706 is provided to the right of the case display region 710. "Mode: DICOM Viewer" displayed in the mode display region 710B means that a current mode is the DICOM viewer mode.

In the slice number display region 710A, a slice number of the currently displayed thumbnail image is displayed. In the example illustrated in FIG. 6B, "32/75" is displayed in the slice number display region 710A. The slice number display region 710A illustrated in FIG. 6B indicates that the similar case illustrated in FIG. 6B (that is, the similar case in the first row and the first column illustrated in FIG. 5) includes 75 slice images. The slice number display region 710A illustrated in FIG. 6B also indicates that the thumbnail image illustrated in FIG. 6B is a thirty-second slice image among the 75 slice images.

Now, a purpose of use of the DICOM viewer mode illustrated in FIG. 6B will be described. As illustrated in FIG. 5, in the base image K2 displayed after the similar case retrieval application is activated, the slice images, each including a CROI, are displayed as thumbnail images. If the user desires to check previous and next slice images of a slice image including the CROI, the user displays the base screen K4 in the DICOM viewer mode illustrated in FIG. 6B.

In FIG. 6B, if the user touches the scroll bar 706 with an object and moves the object in contact with the scroll bar

706 upward or downward, the input control unit 103 detects the touch and the movement. The display control unit 104 moves the display position of the scroll bar 706 in accordance with the movement of the object. In addition, the display control unit 104 switches the thumbnail image displayed in the case display region 710 to a slice image corresponding to the position of the scroll bar 706. As a result of this operation, the user can check the previous and next slice images of the slice image including the CROI.

In the base screen K4 in the DICOM viewer mode illustrated in FIG. 6B, for example, if the user selects the thumbnail image displayed in the case display region 710 by double-tapping the thumbnail image with an object, the input control unit 103 detects the selection. The display control unit 104 displays the base screen K3 illustrated in FIG. 6A on the display 101. Here, for example, a "Return" button may be displayed in the base screen K4 in the DICOM viewer mode illustrated in FIG. 6B. If the "Return" button is selected, the base screen K4 in the DICOM viewer mode illustrated in FIG. 6B may return to the base screen K3 illustrated in FIG. 6A.

In FIG. 5, in an upper left portion of the base screen K2, the disease list display region 730 having a title "disease list" is provided. In the disease list display region 730, confirmed diagnoses of all similar cases, which have been obtained as a result of the retrieval of similar cases, are displayed. After a diagnosis is made and a disease is identified through the diagnosis, a diagnosis target case is accumulated in the case retrieval system 300 as a similar case. Therefore, each similar case includes a confirmed diagnosis.

FIG. 7 is an enlarged diagram of the disease list display region 730. In FIG. 7, confirmed diagnoses are classified on the basis of large categories (731, 734, 737, 741, and 744) and small categories (732, 733, 735, 736, 738, 739, 740, 742, 743, and 745). In the example illustrated in FIG. 7, mycosis 731, neoplastic 734, nonneoplastic 737, mycobacteriosis 741, and others 744 are displayed as the large categories.

In the example illustrated in FIG. 7, aspergillosis 732 and cryptococcosis 733 are displayed as small categories of the mycosis 731. Lung cancer 735 and metastatic lung cancer 736 are displayed as small categories of the neoplastic 734. Lung abscess 738, sarcoidosis 739, and septic emboli 740 are displayed as small categories of the neoplastic 737. Nontuberculous mycobacteria (NTM) 742 and tuberculosis 743 are displayed as small categories of the mycobacteriosis 741. Bronchiectasis 745 is displayed as a small category of the others 744.

Figure 9:
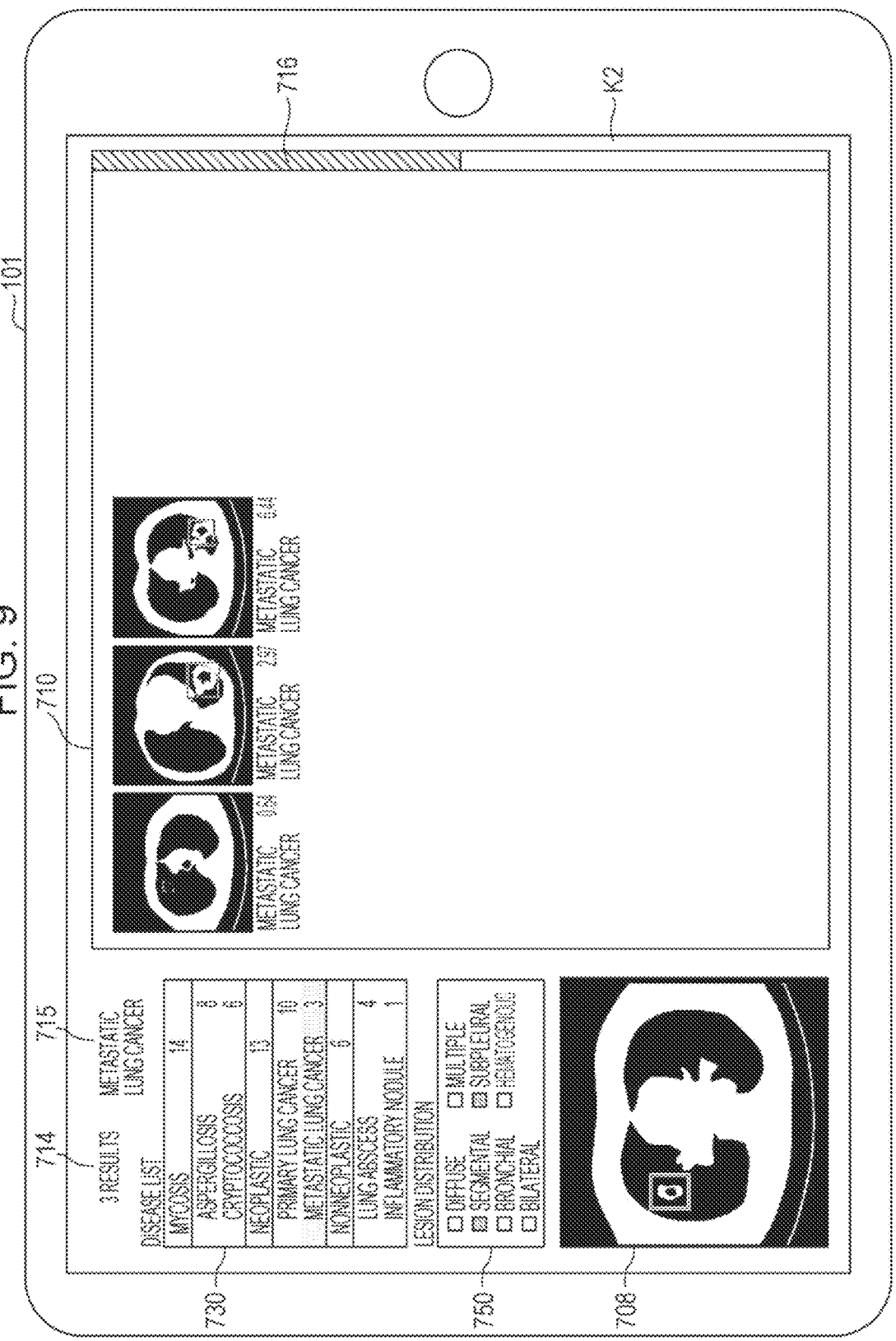
FIG. 9 is a diagram illustrating a base screen at a time when the similar cases have been narrowed down using "metastatic lung cancer"

In addition, the number of cases of each category is displayed next to each of the large categories and the small categories. By selecting one of the large categories and the small categories displayed in the disease list display region 730, the user can narrow down the similar cases displayed in the case display region 710. As illustrated in FIG. 5, the 62 similar cases including various diseases are displayed immediately after the retrieval of similar cases, but if the user taps the mycosis 731 illustrated in FIG. 7 with an object, the display control unit 104 displays only similar cases of mycosis in the case display region 710 as illustrated in FIG. 8. If the user taps the metastatic lung cancer 736 illustrated in FIG. 7 with an object, the display control unit 104 displays only similar cases of metastatic lung cancer in the case display region 710 as illustrated in FIG. 9.

At this time, the display control unit 104 displays a category in the display condition display region 715 so that the user can understand which category the similar cases currently displayed in the case display region 710 belong to. FIG. 8 is a diagram illustrating the base screen K2 at a time when the similar cases have been narrowed down using "mycosis". FIG. 9 is a diagram illustrating the base screen K2 at a time when the similar cases have been narrowed down using "metastatic lung cancer".

In the example illustrated in FIG. 8, since "mycosis" has been used for narrowing down the similar cases, "mycosis" is displayed in the display condition display region 715. In the example illustrated in FIG. 9, since "metastatic lung cancer" has been used for narrowing down the similar cases, "metastatic lung cancer" is displayed in the display condition display region 715.

At this time, the display control unit 104 displays the number of similar cases currently displayed in the case display region 710 in the retrieval result number display region 714 so that the user can understand the number of similar cases. In the example illustrated in FIG. 8, because the number of similar cases falling into the category of "mycosis" is 14, "14 results" is displayed in the retrieval result number display region 714. In the example illustrated in FIG. 9, because the number of similar cases falling into the category of "metastatic lung cancer" is 3, "3 results" is displayed in the retrieval result number display region 714.

Because of this function, only similar cases falling into a category determined by the doctor as a target of image diagnosis are displayed in the case display region 710. Therefore, the doctor can easily check whether a diagnosis target case contradicts a disease presumed thereby.

Figure 10:
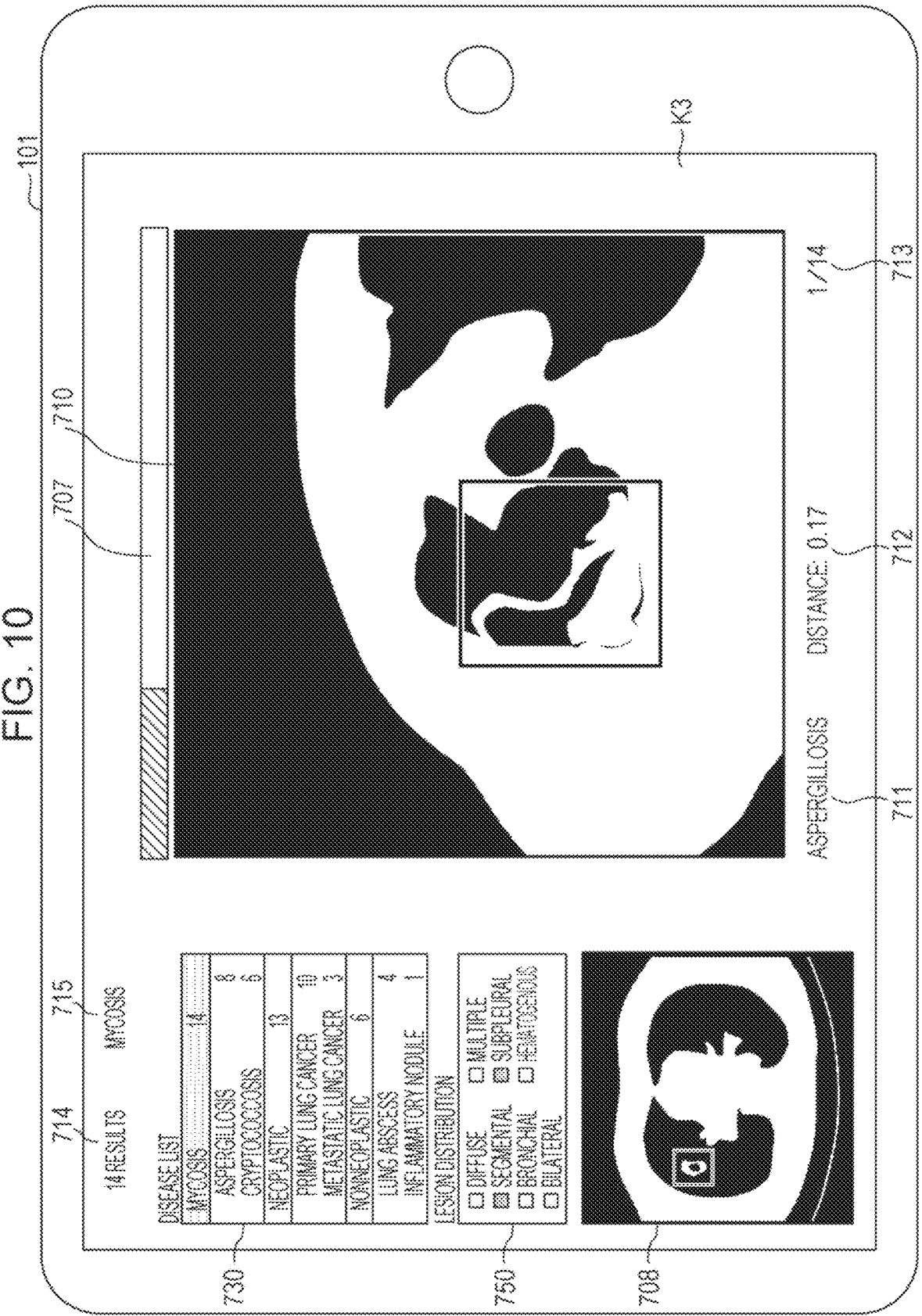
FIG. 10 is a diagram illustrating an example of the base screen displayed on the display.
Figure 11:
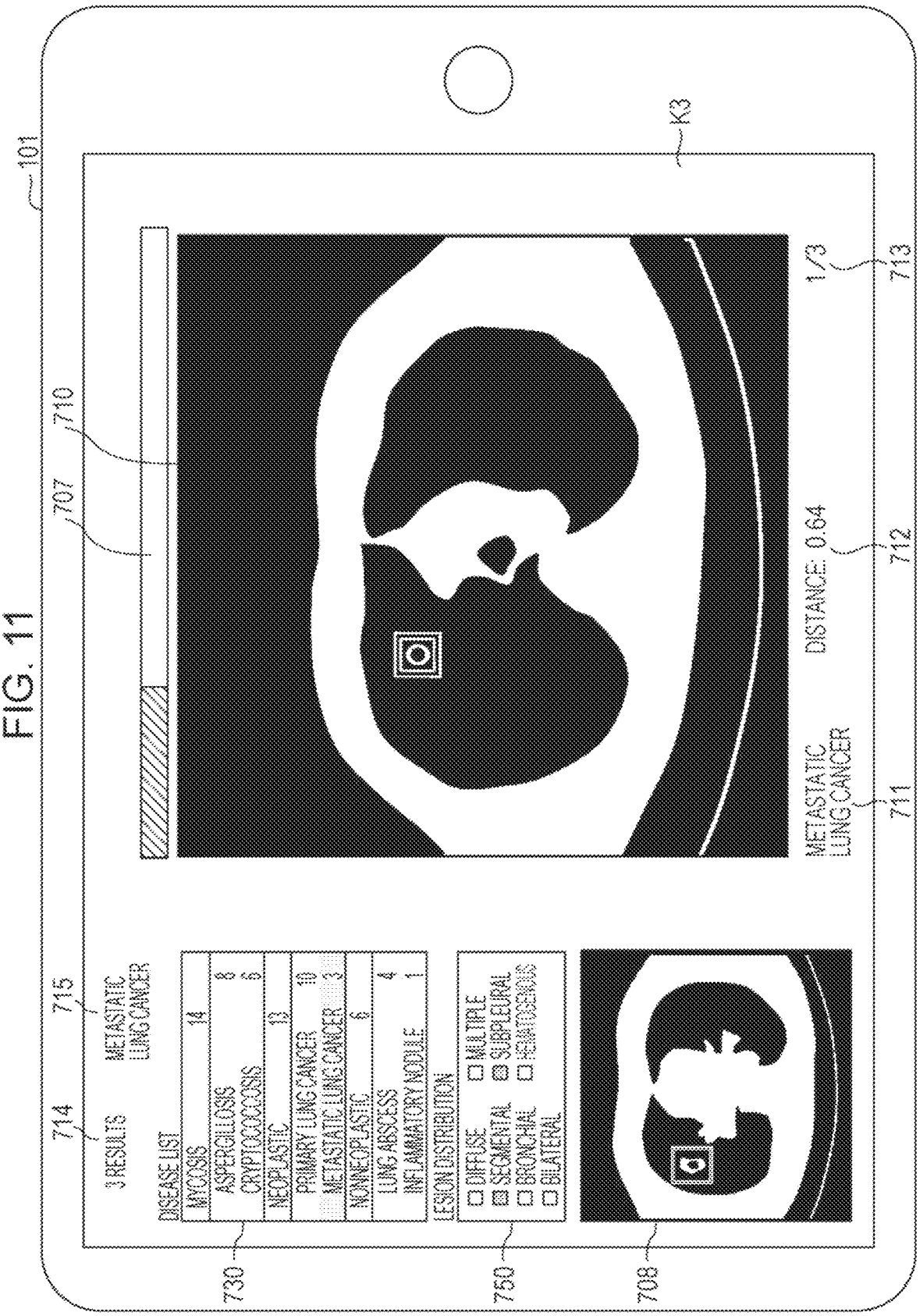
FIG. 11 is a diagram illustrating an example of the base screen displayed on the display.

FIGS. 10 and 11 are diagrams illustrating examples of the base screen K3 displayed on the display 101. In the base screen K2 illustrated in FIG. 8, for example, if the user selects the thumbnail image in the first row and the first column by double-tapping the thumbnail image with an object, the input control unit 103 detects the selection. The display control unit 104 displays, as illustrated in FIG. 10, the base screen K3 in which the selected thumbnail image is displayed across the case display region 710 on the display 101. Similarly, in the base screen K2 illustrated in FIG. 9, for example, if the user selects a thumbnail image in a first row and a first column, the base screen K3 illustrated in FIG. 11 is displayed.

The base screen K3 illustrated in FIG. 10 or 11 is a screen similar to the base screen K3 illustrated in FIG. 6A. Switching of a screen is performed in the same manner as that described above.

That is, in the base screen K3 illustrated in FIG. 10, for example, if the user selects the thumbnail image displayed in the case display region 710 by tapping the thumbnail image with an object, the input control unit 103 detects the selection. The display control unit 104 displays the base screen K2 illustrated in FIG. 8 on the display 101. Similarly, if the user taps the thumbnail image in the base screen K3 illustrated in FIG. 11, the base screen K2 illustrated in FIG. 9 is displayed.

In the base screen K3 illustrated in FIG. 10 or 11, if the user selects the thumbnail image displayed in the case display region 710 by double-tapping the thumbnail image with an object, the input control unit 103 detects the selection. The display control unit 104 displays the base screen K4 in the DICOM viewer mode on the display 101.

In FIG. 5, in the middle of a left part of the base screen K2, the distribution list display region 750 having a title "lesion distribution" is provided. In the distribution list display region 750, types of lesion distribution of all the similar cases obtained from the case retrieval system 300 as a result of the retrieval of similar cases are displayed.

FIG. 12 is an enlarged diagram of the distribution list display region 750. In the example illustrated in FIG. 12, names of seven types of lesion distribution are displayed, and a checkbox is provided to the left of the name of each type of region distribution. In the example illustrated in FIG. 12, diffuse 751, segmental 752, bronchial 753, bilateral 754, multiple 755, subpleural 756, and hematogenous 757 are displayed as the types of lesion distribution.

These types of lesion distribution are defined in advance, and distribution flag values (1 for applicable and 0 for inapplicable) indicating whether these types of lesion distribution, namely the diffuse 751 to the hematogenous 757, apply are given to each similar case. All the distribution flag values might be 0 for some similar cases, whereas a plurality of distribution flag values might be 1 for other similar cases.

The case retrieval system 300 according to this embodiment retrieves similar cases including ROIs similar to a ROI set by the user in a slice image of a diagnosis target case. A lesion might exist in slice images other than the slice image in which the user has set a ROI. After retrieving similar cases using the slice image in which the user has set a ROI, the user might desire to compare slice images other than the slice image in which the user has set a ROI with the retrieved similar cases. In this case, the user displays other slice images by performing an operation for displaying the other slice images in the medical image viewer 705 (FIG. 4), in order to compare the other slice images with the retrieved similar cases. If, among all the retrieved similar cases, only similar cases relating to a target lesion are displayed in the case display region 710, slice images including the desired lesion can be smoothly extracted from the slice images other than the slice image in which the user has set a ROI. Therefore, in this embodiment, a function of narrowing down the retrieved similar cases on the basis of a desired type of lesion distribution is provided in order to smoothly perform this operation.

In this embodiment, as types of lesion distribution in the lung field, the diffuse 751 to the hematogenous 757 illustrated in FIG. 12 are adopted. As illustrated in FIG. 12, the display control unit 104 displays the checkboxes and the names of the types of lesion distribution such that types of lesion distribution with which the similar cases can be narrowed down are displayed in an active state and a type of lesion distribution with which the similar cases cannot be narrowed down is displayed in an inactive state. Here, luminance indicating the active state is higher than luminance indicating the inactive state. The luminance indicating the inactive state is lower than the luminance indicating the active state.

In the example illustrated in FIG. 12, the diffuse 751 and the bronchial 753 to the hematogenous 757 are displayed in the active state, and the segmental 752 is displayed in the inactive state. This is because the distribution flag values of the diffuse 751 and the bronchial 753 to the hematogenous 757 are 1 (applicable) in at least one of all the similar cases obtained as a result of the retrieval of similar cases, and the distribution flag value of the segmental 752 is 0 (inapplicable) in all the obtained similar cases.

If the input control unit 103 detects that one or more checkboxes in the active state are checked, the display control unit 104 displays, in the case display region 710, only similar cases corresponding to the types of lesion distribution whose checkboxes have been checked.

With respect to the segmental 752, the distribution flag value is 0 (inapplicable) in all the similar cases obtained as a result of the retrieval. Therefore, if the checkbox for the segmental 752 can be checked, it is of no use to check the checkbox because no similar cases are displayed in the case display region 710. Therefore, in this embodiment, types of lesion distribution whose distribution flag values are 0 (inapplicable) in all the similar cases obtained as a result of the retrieval are displayed in the inactive state in order to avoid such a situation.

Figure 14A:
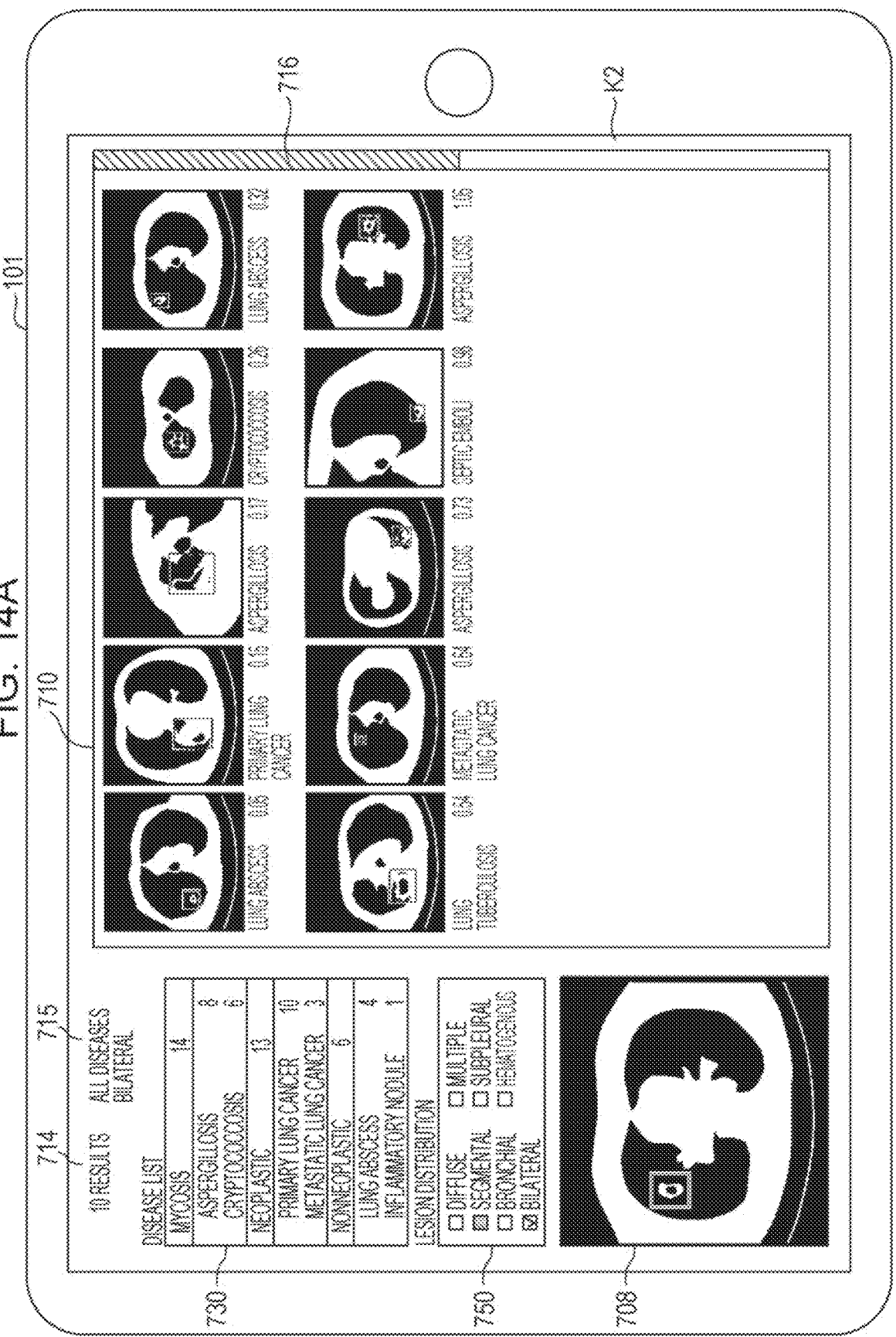
FIG. 14A is a diagram illustrating a base screen in which the similar cases have been narrowed down using a type of lesion distribution of "bilateral"

FIG. 13 is a diagram illustrating the distribution list display region 750 in which the checkbox for the bilateral 754 has been checked. FIG. 14A is a diagram illustrating the base screen K2 in which the similar cases have been narrowed down using the type of lesion distribution of the bilateral 754. As illustrated in FIG. 13, if the checkbox for the bilateral 754 is checked, the display control unit 104 displays, as illustrated in FIG. 14A, only similar cases including the type of lesion distribution of bilateral in the case display region 710. In this case, the number of similar cases including the type of lesion distribution of bilateral is 10. Therefore, the display control unit 104 displays "10 results" in the retrieval result number display region 714. The display control unit 104 also displays the name of a displayed disease and the name of the type of lesion distribution, "bilateral", in the display condition display region 715. Because the similar cases have not been narrowed down on the basis of a category displayed in the disease list display region 730 in the example illustrated in FIG. 14A, "all diseases" is displayed in the display condition display region 715.

FIG. 14B is a diagram illustrating an example of the base screen K3 displayed on the display 101. In the base screen K2 illustrated in FIG. 14A, for example, if the user selects a thumbnail image in a first row and a first column by double-tapping the thumbnail image with an object, the input control unit 103 detects the selection. The display control unit 104 displays, as illustrated in FIG. 14B, the base screen K3 in which the selected thumbnail image is displayed across the case display region 710 on the display 101. The base screen K3 illustrated in FIG. 14B is similar to the base screen K3 illustrated in FIG. 6A. Switching of a screen is performed in the same manner as that described above.

Similarly, if the checkbox for the multiple 755 is checked, the display control unit 104 displays only similar cases including the type of lesion distribution of multiple in the case display region 710. Similarly, if the checkbox for the diffuse 751 is checked, the display control unit 104 displays only similar cases including the type of lesion distribution of diffuse in the case display region 710. Similarly, if the checkbox for the hematogenous 757 is checked, the display control unit 104 displays only similar cases including the type of lesion distribution of hematogenous in the case display region 710.

Figure 16:
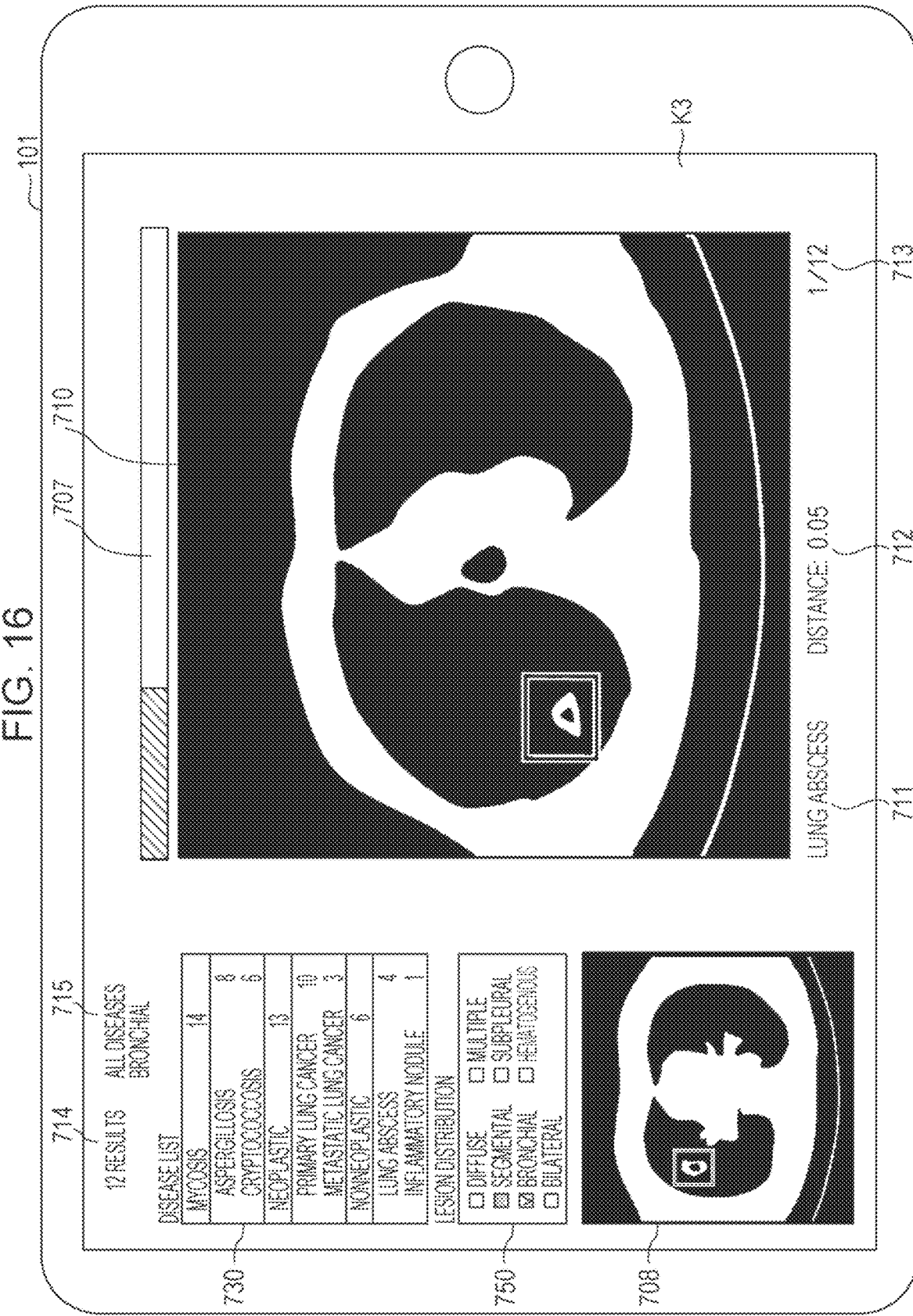
FIG. 16 is a diagram illustrating a base screen displayed when, in a base screen in which the similar cases have been narrowed down using the type of lesion distribution of "bronchial", a thumbnail image in a first row and a first column has been selected.

FIG. 15 is a diagram illustrating the distribution list display region 750 in which the checkbox for the bronchial 753 is checked. FIG. 16 is a diagram illustrating the base screen K3 displayed when a thumbnail image in a first column and a first row has been selected in a base screen obtained by narrowing down similar cases on the basis of the type of lesion distribution of the bronchial 753. As illustrated in FIG. 15, if the checkbox for the bronchial 753 is checked, the display control unit 104 displays only similar cases including the type of lesion distribution of bronchial on the case display region 710. If the thumbnail image in the first row and the first column is selected, the selected thumbnail image is displayed across the case display region 710 as illustrated in FIG. 16. In the example illustrated in FIG. 16, the number of similar cases including the type of lesion distribution of bronchial is 12. Therefore, the display control unit 104 displays "12 results" in the retrieval result number display region 714. The display control unit 104 also displays the name of the disease to be displayed and the name of the type of lesion distribution, "bronchial", in the display condition display region 715. Because the similar cases have not been narrowed down on the basis of a category displayed in the disease list display region 730 in the example illustrated in FIG. 16, "all diseases" is displayed in the display condition display region 715.

Similarly, if the checkbox for the segmental 752 is checked, the display control unit 104 displays only similar cases including the type of lesion distribution of segmental in the case display region 710.

Figure 18:
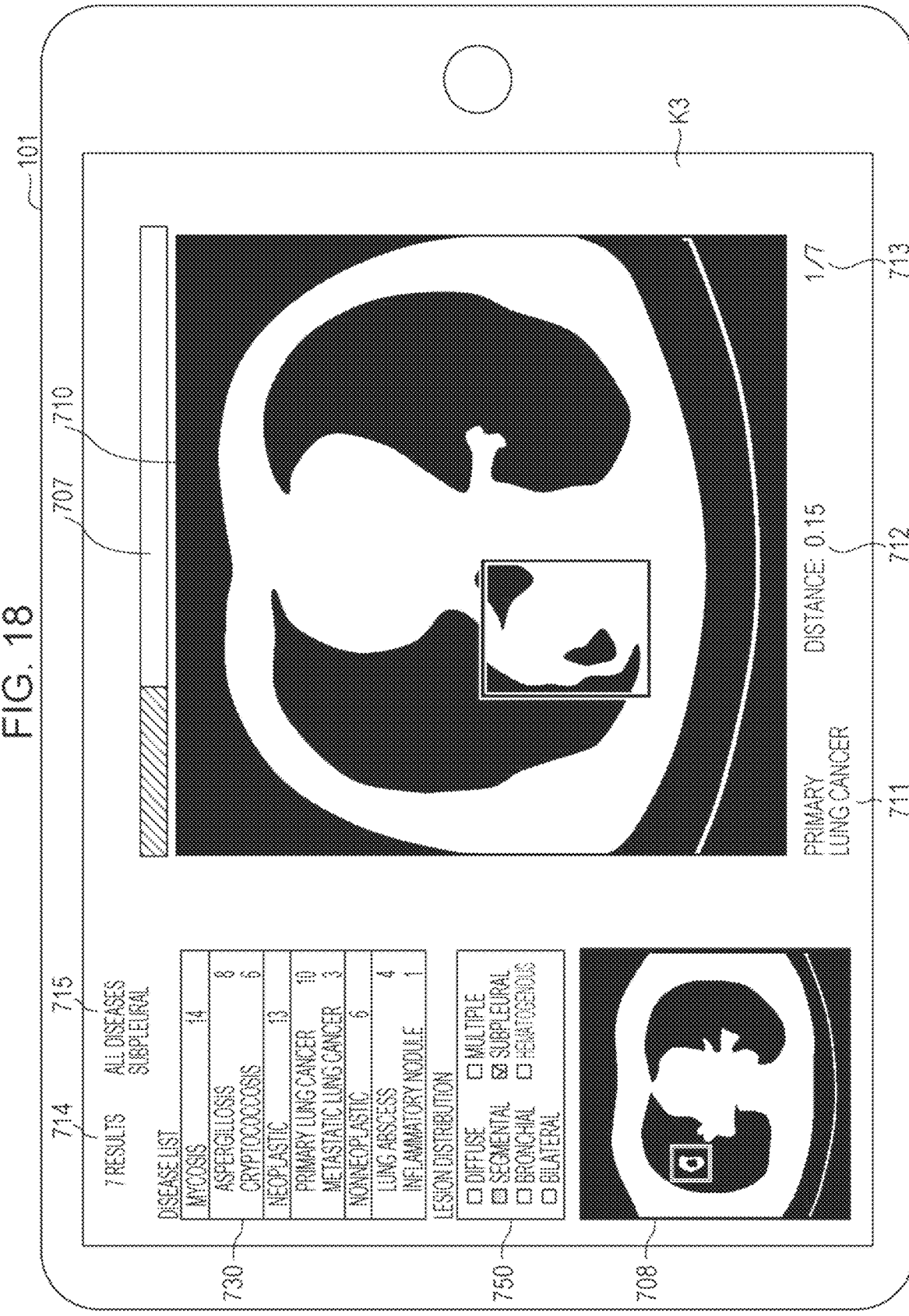
FIG. 18 is a diagram illustrating a base screen displayed when, in a base screen in which the similar cases have been narrowed down using the type of lesion distribution of "subpleural", a thumbnail image in the first row and the first column has been selected.

FIG. 17 is a diagram illustrating the distribution list display region 750 in which the checkbox for the subpleural 756 has been checked. FIG. 18 is a diagram illustrating the base screen K3 displayed when a thumbnail image in a first row and a first column has been selected in a base screen obtained by narrowing down similar cases on the basis of the type of lesion distribution of the subpleural 756. As illustrated in FIG. 17, if the checkbox for the subpleural 756 is checked, the display control unit 104 displays only similar cases including the type of lesion distribution of subpleural in the case display region 710. If the thumbnail image in the first row and the first column is selected, the selected thumbnail image is displayed across the case display region 710 as illustrated in FIG. 18. In the example illustrated in FIG. 18, the number of similar cases including the type of lesion distribution of subpleural is 7. Therefore, the display control unit 104 displays "7 results" in the retrieval result number display region 714. The display control unit 104 also displays the name of the disease to be displayed and the name of the type of lesion distribution, "subpleural", in the display condition display region 715. Because the similar cases have not been narrowed down on the basis of a category displayed in the disease list display region 730 in the example illustrated in FIG. 18, "all diseases" is displayed in the display condition display region 715.

FIG. 19 is a diagram illustrating the data structure of the patient information 1000. The patient information management unit 202 of the medical information management system 200 accumulates the patient information 1000 in the patient information accumulation unit 201 and manages the patient information 1000 for each patient. In the patient information 1000, personal information such as the gender and age of each patient, clinical information such as past medical histories, and test information regarding a blood test or the like are registered. As illustrated in FIG. 19, the patient information 1000 includes, for each patient, a patient identifier (ID) 1100, a name 1200, age 1300, gender 1400, a past medical history 1500, a family medical history 1600, a chief complaint 1700, test information 1800, and a confirmed diagnosis 1900.

The patient ID 1100 is an identifier unique to each patient. The name 1200, the age 1300, the gender 1400, the past medical history 1500, the family medical history 1600, and the chief complaint 1700 are the name, age, gender, past medical history, family medical history, and chief complaint of each patient identified by the patient ID 1100. The test information 1800 indicates, as illustrated in FIG. 20, information regarding one or more medical tests that each patient has undergone in the past.

FIG. 20 is a diagram illustrating a data structure of the test information 1800 illustrated in FIG. 19. The test information 1800 is information regarding tests conducted on each patient and created for each medical test. The test information 1800 includes a test ID 1810, a test time 1820, a test type 1830, and test results 1840. The test ID 1810 is an identifier unique to each medical test. The test time 1820 indicates a time at which each test has been conducted. The test type 1830 indicates the type of medical test. Types of medical test include, for example, a blood test, a respiratory function test, endoscopy, plain roentgenography, and CT scanning.

The test results 1840 refer to, in the case of a blood test, a white blood cell count and values of various markers such as lactate dehydrogenase (LDH) and glutamic-pyruvic transaminase (GPT). The test results 1840 also include a diagnosis given by a doctor on the basis of the various markers. In the case of an imaging test such as plain roentgenography or CT scanning, the test results 1840 include pointer information in captured images and pointer information in a report on results of imaging. Images captured during a test are accumulated in the medical image data accumulation unit 203 of the medical information management system 200 in a DICOM format.

If the test type 1830 is an imaging test such as plain roentgenography, CT, MRI, or positron emission tomography (PET), medical image data is accumulated in the image forming apparatus 2000 stored in the medical image data accumulation unit 203 of the medical information management system 200.

Figure 21:
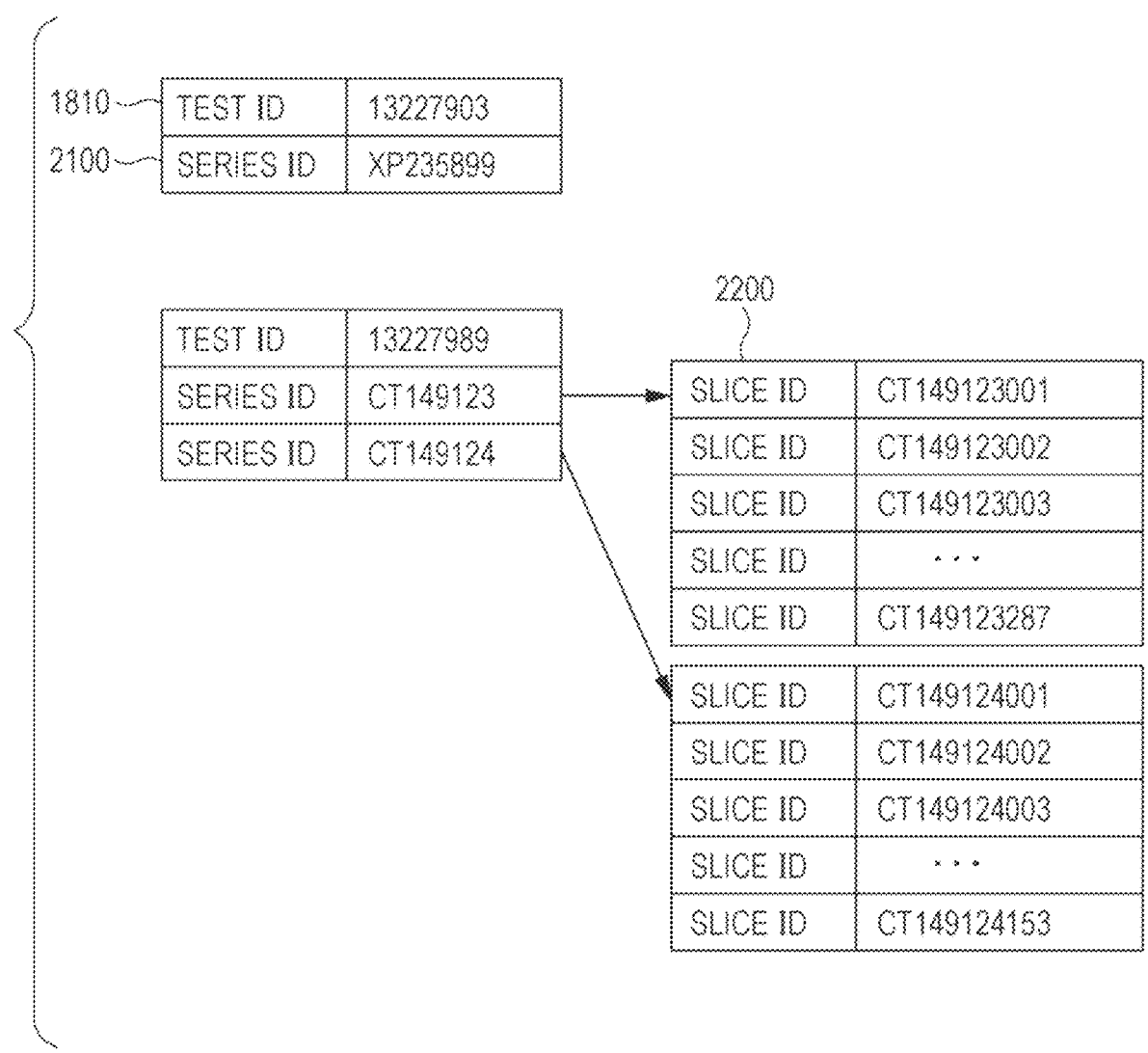
FIG. 21 is a diagram illustrating a data structure of a medical image database.

FIG. 21 is a diagram illustrating a data structure of the image forming apparatus 2000. The image forming apparatus 2000 includes a test ID 1810 and a series ID 2100. Because a plurality of types of image capture (for example, plain CT, contrast CT, and the like) might be performed in a single test, a plurality of series IDs 2100 might be associated with a test ID 1810. That is, the same number of series as the number of types of image capture are obtained.

Besides for each type of image capture, a series is obtained for each condition of reconfiguration of a captured image. For example, if a captured image is reconfigured under a lung field condition and a mediastinum condition, a series is obtained for each of these conditions. In an image reconfigured under the lung field condition, blood vessels, bronchi, alveoli, and the like are emphasized. In an image reconfigured under the mediastinum condition, structures in the mediastinum, such as blood vessels and lymph nodes, are emphasized. Because an image obtained in a single operation for capturing an image can be reconfigured under the lung field condition and the mediastinum condition, two series in the lung field condition and two series under the mediastinum condition are obtained if two images obtained from plain CT and contrast CT are reconfigured under the lung condition and the mediastinum condition.

In the case of an imaging test such as CT or MRI, a plurality of slice images are obtained in a single operation for capturing an image. Therefore, a plurality of slice IDs 2200 are associated with a series ID 2100. Two series IDs "CT149123" and "CT149124" are associated with a test ID "13227989" illustrated in FIG. 21, which indicates that two series of CT images have been obtained from an imaging test. In addition, a plurality of slice IDs 2200 are associated with each of the series IDs "CT149123" and "CT149124".

If the test type 1830 is an imaging test such as plain roentgenography, CT, MRI, or PET, for example, a diagnosis report 3000 illustrated in FIG. 22 is accumulated in the diagnosis report management unit 205 of the medical information management system 200. In the diagnosis report 3000, a diagnosis given by a doctor in each test are registered.

FIG. 22 is a diagram illustrating a data structure of the diagnosis report 3000. The diagnosis report 3000 includes a test ID 1810, observations 3100, and a diagnosis 3200. The test ID 1810 is the same as the test ID 1810 illustrated in FIG. 20. Thus, the diagnosis report 3000 and the test information 1800 are associated with each other. In the observations 3100, a text indicating a doctor's observations after each test is registered. In the diagnosis 3200, a text indicating a doctor's diagnosis after each test is registered.

FIG. 23 is a diagram illustrating a data structure of the similar case data 4000. The similar case data 4000 is referred to in order to retrieve cases similar to a diagnosis target case and created for each similar case. The similar case data 4000 is an example of additional information regarding similar cases. The similar case data 4000 is accumulated in the similar case data accumulation unit 301 of the case retrieval system 300 for each similar case. As illustrated in FIG. 23, the similar case data 4000 includes a similar case ID 4100, a slice ID 4200, ROI information 4300, image feature data 4400, thumbnail image data 4500, lesion distribution information 4600, a confirmed diagnosis (large category) 4700, and a confirmed diagnosis (small category) 4800.

The similar case ID 4100 is an identifier of the similar case data 4000. Here, because the similar case data 4000 is generated for each ROI set in a slice image of a similar case, the similar case ID 4100 is, in a sense, an identifier of each ROI. In the example illustrated in FIG. 23, the similar case ID 4100 is a character string including "SIM" and subsequent numbers.

Figure 24:
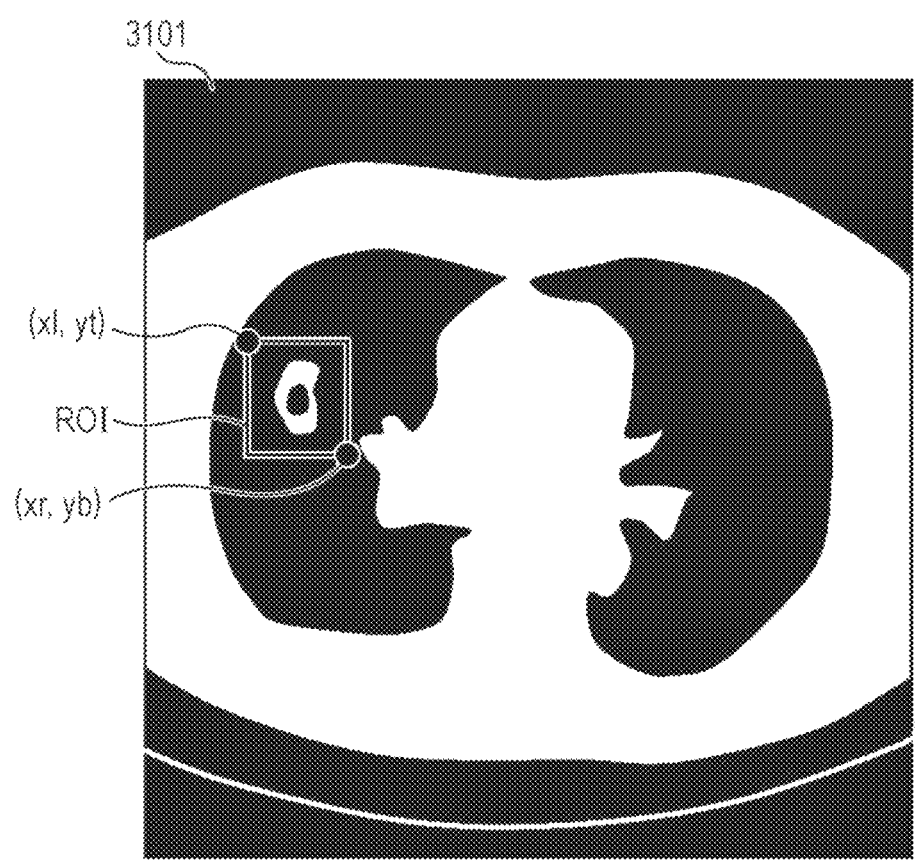
FIG. 24 is a diagram schematically illustrating a region of interest set in a slice image.

The slice ID 4200 is an identifier of a slice image in which a ROI is set and the same as the slice ID 2200 illustrated in FIG. 21. The ROI information 4300 is information indicating a position of a ROI set in a slice image. FIG. 24 is a diagram schematically illustrating a ROI set in a slice image 3101. In the example illustrated in FIG. 24, the set ROI is rectangular. Therefore, the ROI information 4300 includes four values, namely coordinates (xl, yt) of an upper-left corner of the ROI and coordinates (xr, yb) of a lower-right corner of the ROI. Obviously, the ROI need not be rectangular. In that case, a parameter for uniquely identifying the ROI is used as the ROI information 4300. For example, if the ROI is circular, coordinates of the center of the circle and the radius of the circle are used as the ROI information 4300.

The image feature data 4400 is a feature value of certain dimensions (N dimensions in this embodiment) extracted from the ROI defined by the ROI information 4300. The thumbnail image data 4500 is image data regarding a thumbnail image to be displayed in the case display region 710 generated on the basis the slice image in the DICOM format identified by the slice ID 4200. Here, in the thumbnail image data 4500, for example, pixel values of a thumbnail image are arranged in order of raster scanning, that is, from an upper-left corner to a lower-right corner of the thumbnail image. As described above, a DICOM image obtained as a result of a CT test is a 11-bit (pixel value: −1,000 to +1,000) image having 512×512 pixels. Therefore, in this embodiment, in order to promptly display a thumbnail image, a thumbnail image having 8-bit pixel values is created in advance by performing a low-resolution process and a tone conversion process on an original DICOM image and registered in the similar case data 4000. For example, the medical information management system 200 may create a thumbnail image and transmit the thumbnail image to the case retrieval system 300, or the case retrieval system 300 may create a thumbnail image after obtaining a DICOM image from the medical information management system 200.

The lesion distribution information 4600 is a distribution flag value (1 for applicable and 0 for inapplicable) indicating whether a target similar case corresponds to each of predetermined types of lesion distribution, namely diffuse 4610 to hematogenous 4670.

The confirmed diagnosis (large category) 4700 is a large category into which a target similar case falls. The confirmed diagnosis (large category) 4700 is used for narrowing down similar cases on the basis of large categories.

The confirmed diagnosis (small category) 4800 is a small category into which a target similar case falls. The confirmed diagnosis (small category) 4800 is used for narrowing down similar cases on the basis of small categories.

Large categories uniquely corresponding to small categories are defined in advance, and the confirmed diagnosis (large category) 4700 and the confirmed diagnosis (small category) 4800 are stored in the similar case data 4000 in accordance with the corresponding relationship.

The medical image data accumulation unit 203 identifies a series ID 2100 from a slice ID 2200 illustrated in FIG. 21 for the confirmed diagnosis (small category) 4800. The patient information accumulation unit 201 identifies a test ID 1810 from the identified series ID 2100, patient information 1000 (FIG. 19) from the identified test ID 1810, and a confirmed diagnosis 1900 from the identified patient information 1000 for each patient.

Next, a procedure from a beginning of a reading operation to a beginning of retrieval of similar cases performed by the information terminal 100 in cooperation with the medical information management system 200 and the case retrieval system 300 will be described.

Figure 25:
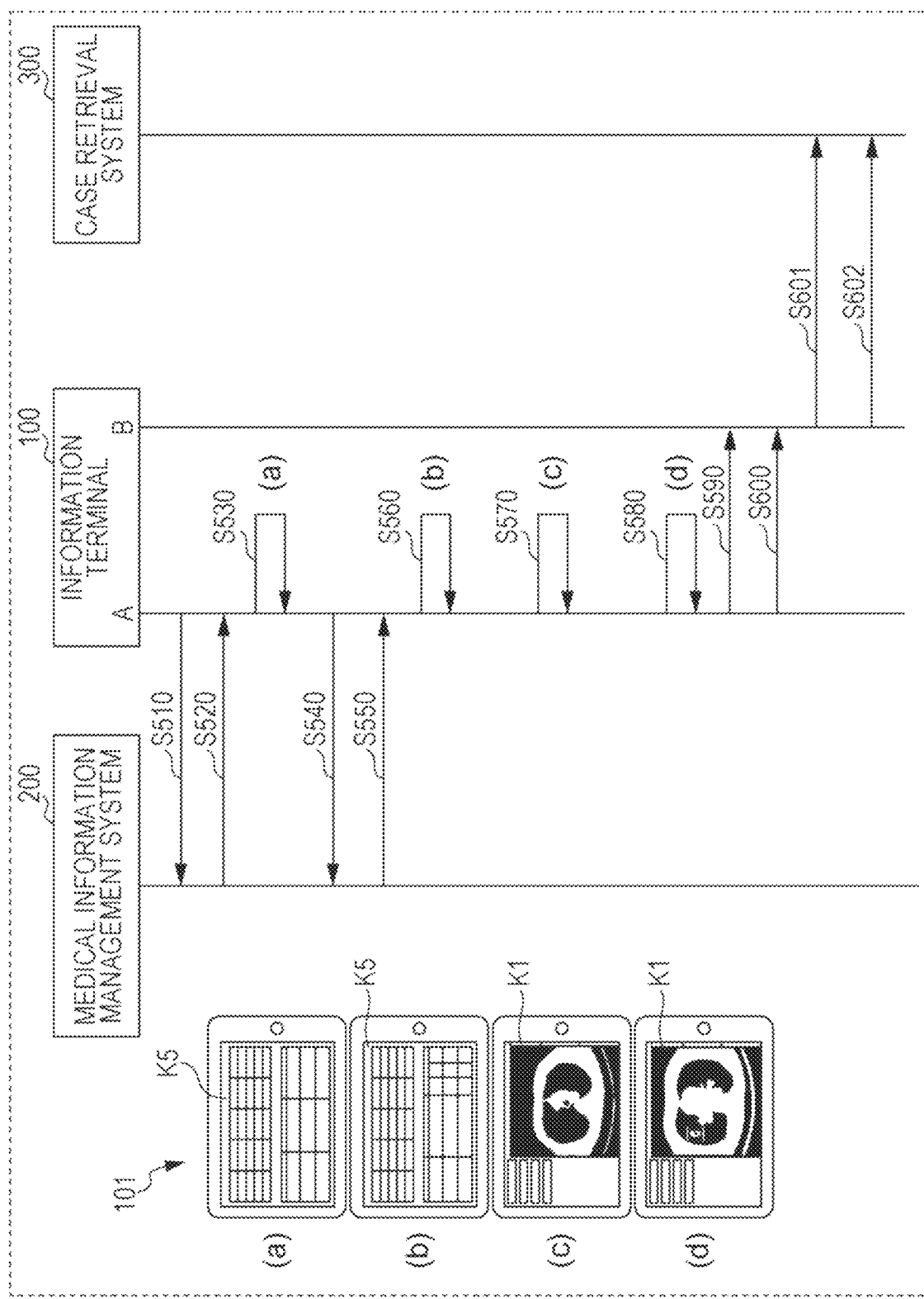
FIG. 25 is a sequence diagram illustrating a process performed until the case retrieval system receives, from the information terminal, a request to retrieve similar cases after the information terminal requests the reading target test list from the medical information management system.

FIG. 25 is a sequence diagram illustrating a process performed until the case retrieval system 300 receives, from the information terminal 100, a request to retrieve similar cases after the information terminal 100 requests the reading target test list from the medical information management system 200. In FIG. 25, rectangles illustrated in a left part of the sequence diagram indicate screens displayed on the display 101 as a result of processing in corresponding steps. In FIG. 25, "A" in the information terminal 100 indicates the medical information management application, and "B" indicates the similar case retrieval application. It is assumed that the medical information management application is activated in advance before this sequence begins.

First, the information terminal 100 receives, from the user (a doctor who reads a medical image), a request to display the reading target test list through the reading target test list button 701 (FIG. 4). The information terminal 100 transmits the request to display the reading target test list to the communication control unit 206 of the medical information management system 200 through the input control unit 103 and the communication control unit 110 (S510).

The patient information management unit 202 of the medical information management system 200 generates a reading target test list, which is a list of tests for which imaging tests have been conducted but reading has not been performed. The patient information management unit 202 transmits the generated reading target test list to the communication control unit 110 of the information terminal 100 through the communication control unit 206 (S520). Here, the reading target test list includes the patient information 1000 and the test information 1800 regarding target patients.

The display control unit 104 of the information terminal 100 displays the reading target test list received by the communication control unit 110 on the display 101 (S530).

Figure 26:
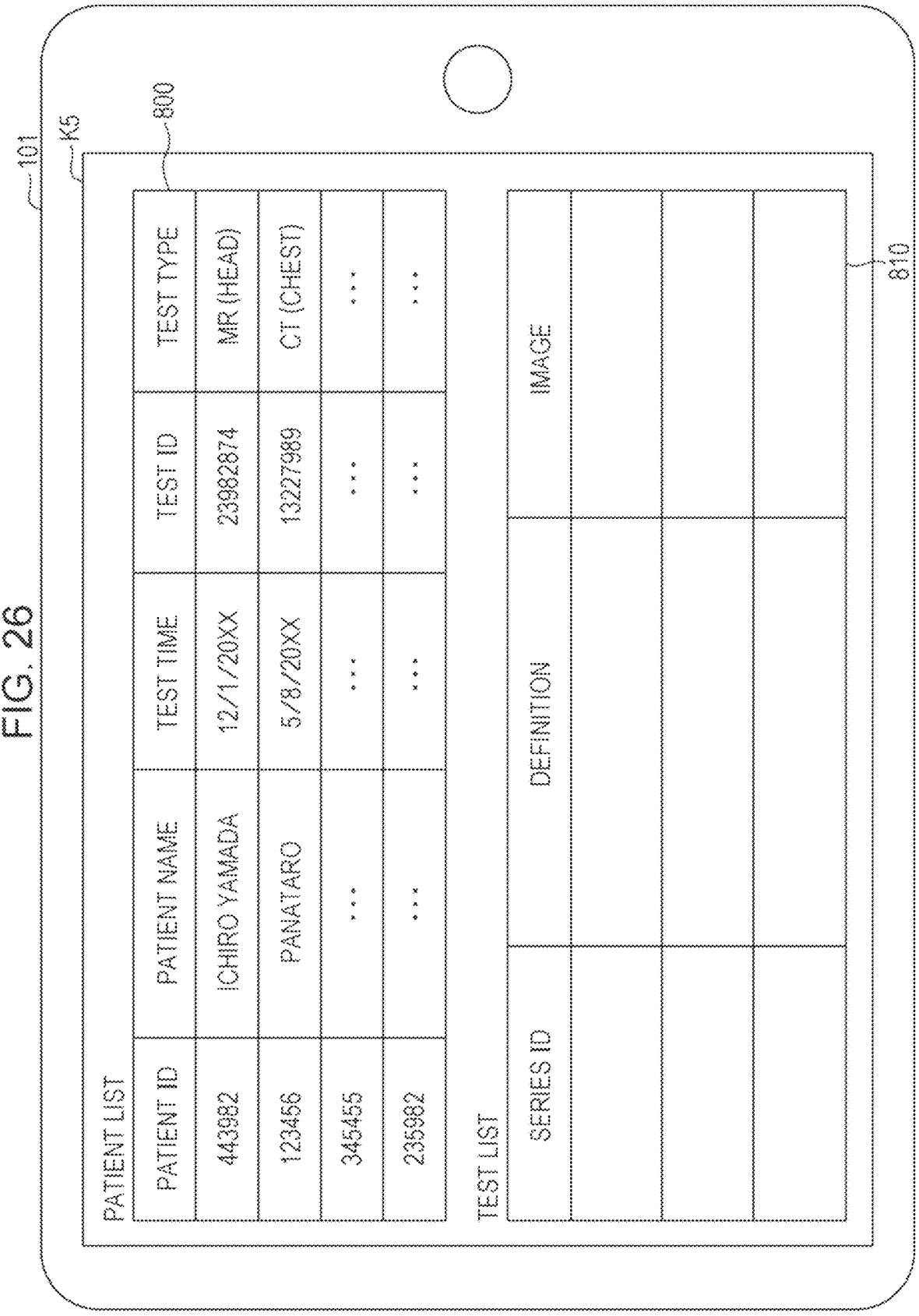
FIG. 26 is a diagram illustrating an example of a display screen for the reading target test list.

FIG. 26 is a diagram illustrating an example of a display screen K5 for the reading target test list. The reading target test list includes a patient list display region 800 in which patients corresponding to the tests for which reading has not been performed are displayed and a test list display region 810 in which information regarding series included in a test is displayed. The patient list display region 800 includes fields of "patient ID", "patient name", "test time", "test ID", and "test type". In the fields of "patient ID" and "patient name", the patient ID 1100 and the name 1200, respectively, registered in the patient information 1000 are displayed, and in the fields of "test time", "test ID", and "test type", the test time 1820, the test ID 1810, and the test type 1830, respectively, registered in the test information 1800 are displayed. The test list display region 810 is a region for displaying details of a test selected by the user in the patient list display region 800 and includes fields of "series ID", "definition", and "image". Here, because the user has not selected any test (corresponds to rows) in the patient list display region 800, no information is displayed in the test list display region 810.

The user selects one of the tests displayed in the patient list display region 800 as a test to be read. The input control unit 103 detects the selection, and, as illustrated in FIG. 25, the communication control unit 110 transmits a request to display all series included in a test ID of the selected test to the medical information management system 200 (S540).

After the communication control unit 206 of the medical information management system 200 receives the display request, the patient information management unit 202 refers to the image forming apparatus 2000 illustrated in FIG. 21. The patient information management unit 202 obtains all slice images of all the series included in the test ID specified by the display request and transmits the slice images to the information terminal 100 through the communication control unit 206 (S550). For example, in the example illustrated in FIG. 21, if the user selects a test identified from the test ID "13227989", all slice images included in the series identified from the series IDs "CT149123" and "CT149124" are transmitted in S550.

If the communication control unit 110 of the information terminal 100 obtains images of the all the series, the display control unit 104 displays a series list including information regarding all the series included in the specified test ID in the test list display region 810 (S560).

FIG. 27 is a diagram illustrating an example of the display screen K5 for the reading target test list after a test is selected. In the patient list display region 800 illustrated in FIG. 27, a selected row is highlighted. In the example illustrated in FIG. 27, a second row, which indicates a test conducted on "Panataro", is selected in the patient list display region 800. Therefore, series IDs, definitions, and images of the selected test are displayed in the test list display region 810. In the field of "series ID", the series IDs associated with a test ID of the selected test are displayed, and in the field of "image", a thumbnail image of a slice image representing each of the displayed series IDs is displayed. Here, an image at a certain slice position is adopted as the slice image representing each series ID. The certain slice position may be a top slice position or may be a central slice position. Each definition indicates image capture conditions, reconfiguration conditions, and the like of each series. Although not illustrated, for example, each definition is registered and associated with a series ID in the image forming apparatus 2000 illustrated in FIG. 21.

In FIG. 25, if the user selects a series to be read in the test list display region 810 and the input control unit 103 detects the selection, the display control unit 104 displays a first slice image of the selected series in the medical image viewer 705 as illustrated in FIG. 4 (S570). As described above with reference to FIG. 4, the display control unit 104 displays all slice images of the selected series on the display 101 such that each slice image can be displayed through scrolling. The user performs image diagnosis while performing an operation for displaying each slice image through scrolling. If it is difficult for the user to perform image diagnosis, the user activates the similar case retrieval application.

Before activating the similar case retrieval application, the user taps the ROI input button 702 (FIG. 4) with an object (for example, the user's finger) to activate a ROI input mode. After the ROI input mode is activated, the ROI management unit 105 begins to manage the information terminal 100, and the information terminal 100 waits for an input of a ROI.

The user sets, through the operation unit 102, a ROI including a lesion in a slice image displayed on the medical image viewer 705 of the display 101 (S580). As illustrated in FIG. 24, for example, the user taps the display 101 with an object to input the coordinates of the upper-left corner of the ROI in the slice image 3101. The user then drags the object on the display 101 in a lower-right direction and releases the object from the display 101 to input the coordinates of the lower-right corner of the ROI.

After the input control unit 103 detects the operation for setting a ROI, the ROI management unit 105 receives data regarding the coordinates of the upper-left corner and the lower-right corner of the ROI from the input control unit 103 and generates the received data as ROI information.

Here, the user activates the similar case retrieval application by tapping the similar case retrieval button 703 with the object. As a result, the ROI management unit 105 transmits the generated ROI information to the communication control unit 110 (S590).

Simultaneously, the ROI management unit 105 transmits a slice image of the diagnosis target case to the communication control unit 110 (S600). In this case, among all the slice images of the series received in S550 by the information terminal 100 from the medical information management system 200, the slice image (retrieval query image) in which the user has set a ROI in the series that the user has selected is transmitted.

Next, the communication control unit 110 receives the ROI information transmitted from the ROI management unit 105 and transmits the ROI to the communication control unit 304 of the case retrieval system 300 (S601).

Simultaneously, the communication control unit 110 receives the slice image transmitted from the ROI management unit 105 and transmits the slice image to the communication control unit 304 of the case retrieval system 300 (S602).

Although the slice image is transmitted in S600 and S601, only a slice ID of the slice image may be transmitted, instead. In this case, after receiving the slice ID, the case retrieval system 300 may obtain the slice image from the medical information management system 200 by specifying the slice ID.

Next, a process performed until the information terminal 100 initially displays results of retrieval of similar cases after the case retrieval system 300 performs the retrieval of similar cases will be described.

Figure 28:
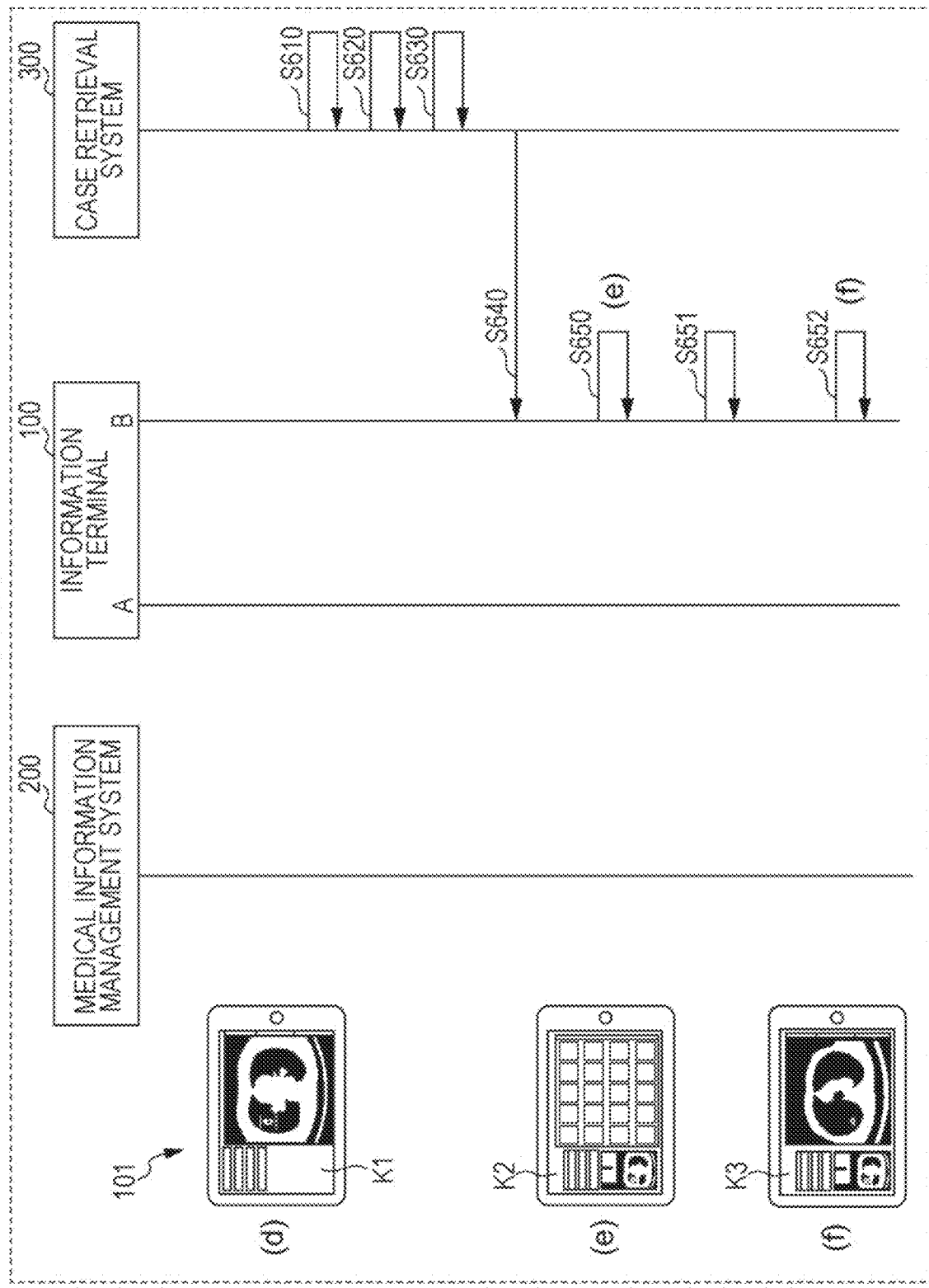
FIG. 28 is a sequence diagram illustrating a process performed until the information terminal displays a base screen on the basis of results of retrieval of similar cases received from the case retrieval system after the case retrieval system receives, from the information terminal, a request to retrieve similar cases.

FIG. 28 is a sequence diagram illustrating the process performed until the information terminal 100 displays a base screen on the basis of results of retrieval of similar cases received from the case retrieval system 300 after the case retrieval system 300 receives a request to perform the retrieval of similar cases from the information terminal 100.

The image feature extraction unit 302 of the case retrieval system 300 extracts a predetermined image feature of a plurality of dimensions set in a retrieval query image (S610).

As the image feature, an image feature relating to the shape of an organ or a lesion in a medical image, an image feature relating to luminance distribution, or the like may be adopted. For example, in Nemoto, Shimizu, Hagiwara, Kobatake, and Nawano "Improvement of Tumor Detection Performance in Mammograms by Feature Selection from a Large Number of Features and Proposal of Fast Feature Selection Method", Systems and Computers in Japan, D-II, Vol. J88-D-II, No. 2, pp. 416-426, February 2005, use of an image feature of 490 dimensions is described. In this embodiment, for example, the image feature described in this non-patent literature is used. This, however, is just an example, and another image feature may be used, instead.

The similar case retrieval unit 303 compares the image feature extracted by the image feature extraction unit 302 with the image features of similar cases accumulated in the similar case data accumulation unit 301 (S620). Here, the similar case retrieval unit 303 compares the image features with each other by calculating a distance between image feature data extracted from the retrieval query image and the image feature data 4400 registered in the similar case data 4000 (FIG. 23) accumulated in the similar case data accumulation unit 301 for each similar case.

Next, the similar case retrieval unit 303 sorts similar cases whose distances are smaller than a certain threshold in order of ascending distance and determines the similar cases as similar cases to be transmitted (S630). Next, the communication control unit 304 transmits, among pieces of data included in the similar case data 4000 accumulated in the similar case data accumulation unit 301, similar case IDs 4100, slice IDs 4200, ROI information 4300, thumbnail image data 4500, lesion distribution information 4600, confirmed diagnoses (large category) 4700, confirmed diagnoses (small category) 4800, and the distances, which have been calculated by the similar case retrieval unit 303, of the similar cases determined as transmission targets to the information terminal 100 (S640).

Next, the display control unit 104 generates, on the basis of the transmitted information, the initial base screen K2 (FIG. 5) in which results of the retrieval of similar cases are displayed (S650).

Figure 29:
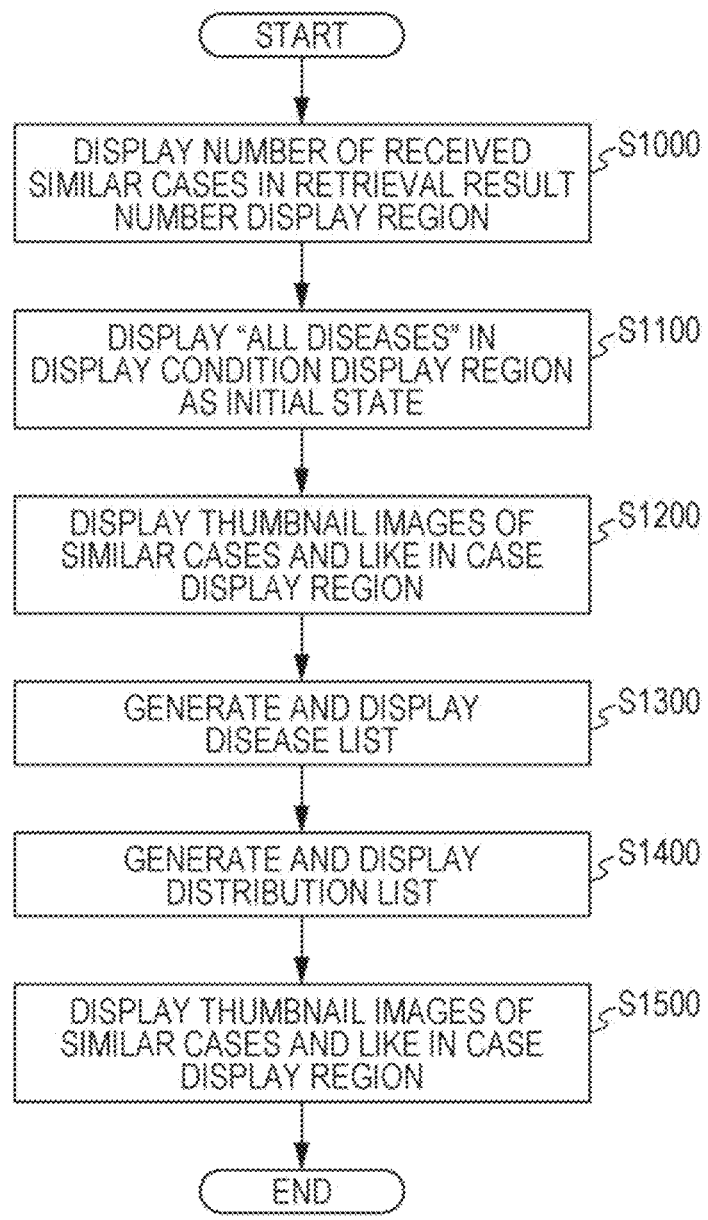
FIG. 29 is a flowchart illustrating details of a process for generating an initial base screen indicated by S650 illustrated in FIG. 28.

FIG. 29 is a flowchart illustrating details of a process for generating the initial base screen K2 indicated by S650 illustrated in FIG. 28.

First, in S1000, the display control unit 104 counts the number of similar cases received in S640 illustrated in FIG. 28 and displays the number in the retrieval result number display region 714.

Next, in S1100, the display control unit 104 displays "all diseases" in the display condition display region 715. The reason why "all diseases" are displayed is that, in the initial base screen K2, the user has not narrowed down the similar cases using a category or a type of lesion distribution.

Next, in S1200, the display control unit 104 displays, in the case display region 710, thumbnail images of a certain number of similar cases that have been received in S640 illustrated in FIG. 28 and that can be displayed in the case display region 710. The display control unit 104 also displays a confirmed diagnosis and similarity for each thumbnail image.

In the example illustrated in FIG. 5, the maximum number of similar cases that can be displayed in the case display region 710 is 20. The maximum number is determined in advance. Alternatively, the user may be able to change the maximum number arbitrarily. If the number of similar cases received in S640 illustrated in FIG. 28 is larger than the maximum number, the display control unit 104 displays the vertically long scroll bar 716 (FIG. 5) at a right end of the case display region 710. As a result, the user can view thumbnail images of similar cases that are not displayed in the initial base screen K2 by moving the scroll bar 716.

Next, in S1300, a disease list is generated and displayed. First, the disease list is generated from the similar cases received in S640 illustrated in FIG. 28. The disease list is a list in which the similar cases received in S640 are classified using confirmed diagnoses.

Here, it is assumed that the number of similar cases received in S640 is NC. The disease list management unit 108 generates the disease list using the confirmed diagnosis (large category) 4700 and the confirmed diagnosis (small category) 4800 registered in the similar case data 4000 regarding each of the NC similar cases. The disease list management unit 108 manages the generated disease list as data having a table format as illustrated in FIG. 30.

FIG. 30 is a diagram illustrating a data structure of the disease list generated in S1300 illustrated in FIG. 29. The disease list includes fields of "disease ID", "large category", "small category", "number", and "similar case ID". "Disease ID" is an identifier provided for each confirmed diagnosis. Here, a disease ID is provided for each combination of a large category and a small category.

"Large category" is a confirmed diagnosis indicated by the confirmed diagnosis (large category) 4700 registered in the similar case data 4000. "Small category" is a confirmed diagnosis indicated by the confirmed diagnosis (small category) 4800 registered in the similar case data 4000. "Number" is the number of similar cases corresponding to the confirmed diagnosis indicated by "disease ID". "Similar case ID" is a similar case ID indicating a case similar to the disease indicated by "disease ID".

The disease list management unit 108 extracts the confirmed diagnosis (large category) 4700 and the confirmed diagnosis (small category) 4800 for each of all the pieces of similar case data 4000 received in S640 and classifies, as similar cases whose confirmed diagnoses are the same, pieces of similar case data 4000 whose confirmed diagnoses (large category) 4700 and confirmed diagnoses (small category) 4800 are the same as one another. The disease list management unit 108 then counts the number of similar cases whose confirmed diagnoses are the same and registers the number to the field of "number" in a record of a corresponding confirmed diagnosis. The disease list management unit 108 also registers similar case IDs of the similar cases classified into the same confirmed diagnosis to the field of "similar case ID" of the record of the corresponding confirmed diagnosis.

In the example illustrated in FIG. 30, a disease ID "DIS528" is provided for a confirmed diagnosis whose large category is "neoplastic" and small category is "primary lung cancer". Because the number of similar cases corresponding to this confirmed diagnosis is 10, 10 is registered to the field of "number" of the corresponding record, and similar case IDs "SIM258", "SIM551", "SIM1209", "SIM2341", and the like of similar cases corresponding to this confirmed diagnosis are registered to the field of "similar case ID" of the corresponding record.

The display control unit 104 generates the disease list display region 730 using the disease list generated in this manner and displays the disease list display region 730 on the display 101.

FIGS. 31, 32, and 33 are diagrams illustrating a first display example, a second display example, and a third display example, respectively, of the disease list display region 730. As illustrated in FIG. 31, in the first display example, similar cases obtained as a result of retrieval of similar cases are displayed in a list in descending order in terms of small categories.

As illustrated in FIG. 32, in the second display example, similar cases obtained as a result of retrieval of similar cases are displayed in a list in descending order in terms of large categories.

As illustrated in FIG. 33, in the third display example, similar cases obtained as a result of retrieval of similar cases are displayed as a list in descending order in terms of large categories and in descending order in terms of small categories included in each large category. In this case, confirmed diagnoses are represented in a hierarchical structure of large categories and small categories.

Figure 34:
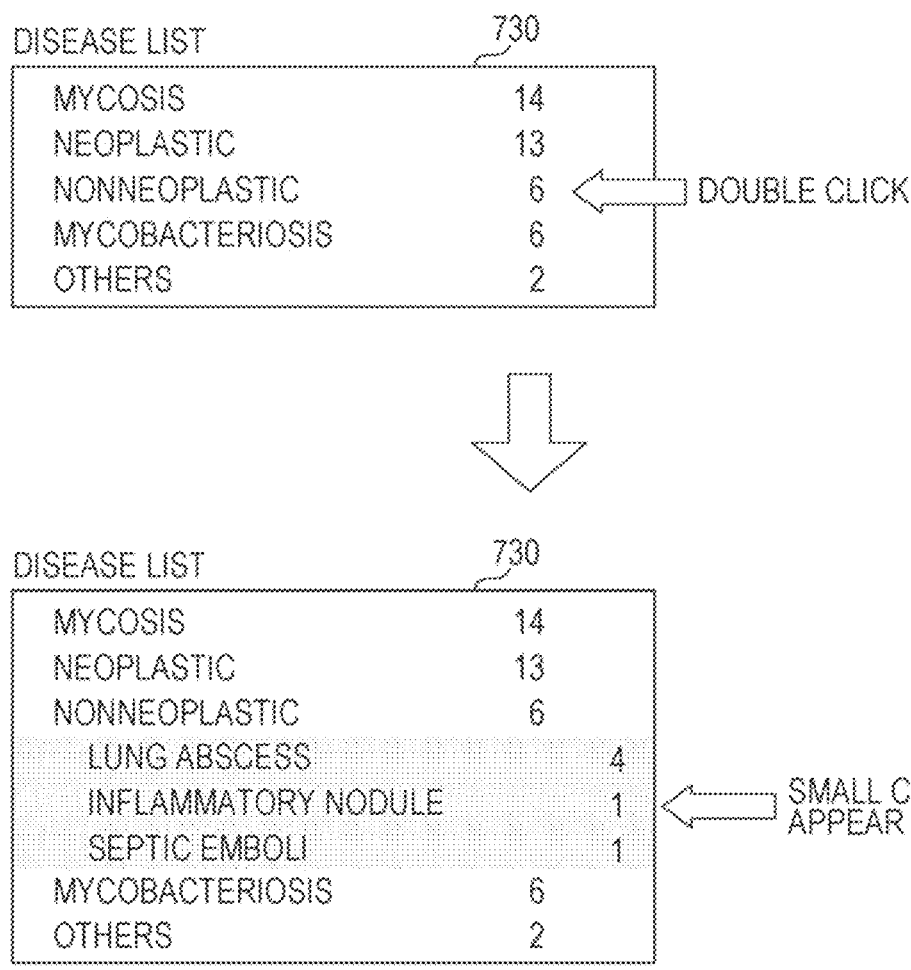
FIG. 34 is a diagram illustrating switching of the disease list display region illustrated in FIG. 32.

FIG. 34 is a diagram illustrating switching of the disease list display region 730 illustrated in FIG. 32. As indicated in an upper part of FIG. 34, if the input control unit 103 detects an operation for selecting one of the large categories displayed in the list, the display control unit 104 displays, as indicated in a lower part of FIG. 34, small categories belonging to the selected large category in descending order. Here, the user may select one of the large categories displayed in the list in the disease list display region 730 by, for example, double-tapping or tapping a desired large category. In the example illustrated in FIG. 34, since "nonneoplastic" has been double-tapped, small categories belonging to "nonneoplastic" is displayed in the list.

In the lower part of FIG. 34, if the user double-taps or taps a region in which the small categories are displayed, the display control unit 104 may hide the small categories displayed in the region.

The display control unit 104 may determine small categories belonging to a large category by referring to the disease list (FIG. 30). For example, in the example illustrated in FIG. 30, since aspergillosis and cryptococcosis are associated with mycosis, the display control unit 104 may determine that aspergillosis and cryptococcosis belong to mycosis.

In FIG. 29, in S1400, a distribution list is generated and displayed. First, a distribution list is generated from the similar cases received in S640. The distribution list is a list in which the similar cases received in S640 are classified using types of lesion distribution.

The disease list management unit 108 generates the distribution list using the lesion distribution information 4600 registered in each of the NC pieces of similar case data 4000. As illustrated in FIG. 35, the distribution list management unit 109 manages the generated distribution list as data having a table format.

FIG. 35 is a diagram illustrating a data structure of the distribution list generated in S1400 illustrated in FIG. 29. The distribution list includes fields of "type of distribution", "number of cases", and "similar case ID". "Type of distribution" indicates a plurality of predetermined types of lesion distribution, such as diffuse and segmental. "Number of cases" indicates the number of similar cases corresponding to each type of lesion distribution. "Similar case ID" indicates a similar case ID indicating a similar case corresponding to each type of lesion distribution.

The distribution list management unit 109 extracts the lesion distribution information 4600 for each of all the pieces of similar case data 4000 received in S640. The distribution list management unit 109 then counts the number of types of lesion distribution for which 1 (applicable) is set to distribution flag values and registers the number to the field of "number of cases" of a record of corresponding types of lesion distribution. The distribution list management unit 109 also registers similar case IDs of similar cases for which 1 is set to distribution flag values to the field of "similar case ID" of the record of the corresponding types of lesion distribution.

In the example illustrated in FIG. 35, since the number of similar cases corresponding to "diffuse" is 3, 3 is registered to the field of "number of cases" of a record of "diffuse". In addition, similar case IDs "SIM2521", "SIM4123", and "SIM5225" of the similar cases corresponding to "diffuse" are registered to the field of "similar case ID".

The display control unit 104 generates the distribution list display region 750 using the distribution list generated in this manner and displays the distribution list display region 750 on the display 101.

The distribution list display region 750 generated using the distribution list illustrated in FIG. 35 is illustrated in FIG. 12. In FIG. 35, since the number of cases corresponding to "segmental" is 0, the segmental 752 illustrated in FIG. 12 is displayed in the inactive state. Since the number of similar cases of the other types of lesion distribution is 1 or more, these types of lesion distribution are displayed in the active state.

In FIG. 29, in S1500, the display control unit 104 displays, as illustrated in FIG. 5, the base screen K2 in which thumbnail images of the similar cases are displayed in the case display region 710 on the display 101.

In FIG. 28, in S651, one of the similar cases is selected by, for example, double-tapping one of the thumbnail images displayed in the case display region 710. In S652, the display control unit 104 displays, on the display 101, the base screen K3 (FIG. 6A) in which the thumbnail image of the selected similar case across the case display region 710. A similar case may be selected through an operation other than tapping or double tapping.

Next, processes performed by the information terminal 100, the medical information management system 200, and the case retrieval system 300 when the sequence diagrams of FIGS. 25 and 28 are seen at a level of the applications will be described.

Figure 36:
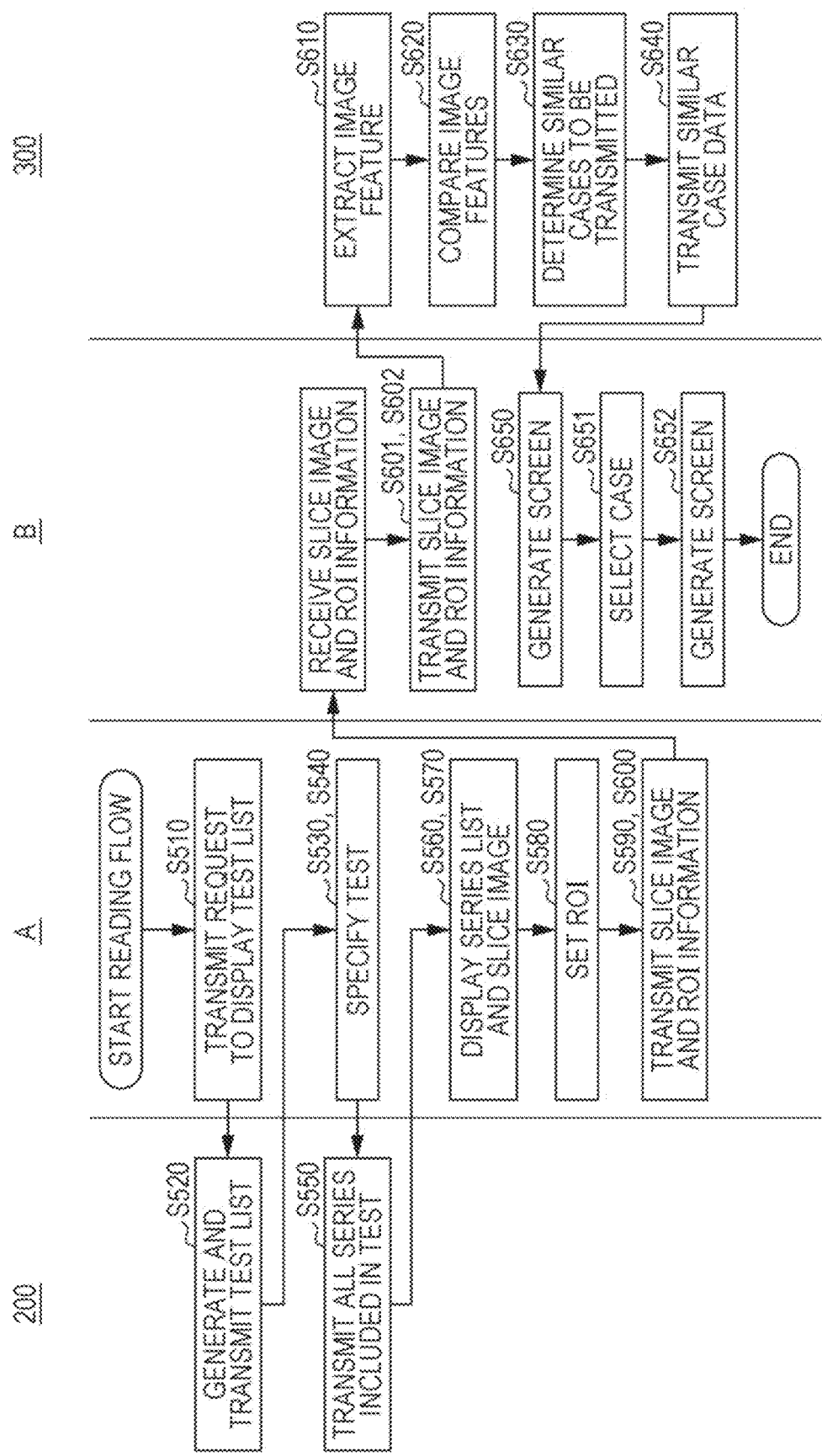
FIG. 36 is a sequence diagram at a time when the sequence diagrams of FIGS. 25 and 28 are seen at a level of applications.

FIG. 36 is a sequence diagram at a time when the sequence diagrams of FIGS. 25 and 28 are seen at the level of the applications. In FIG. 36, the same steps as those illustrated in FIGS. 25 and 28 are given the same reference numerals.

In FIG. 36, "A" indicates a process performed by the medical information management application executed by the information terminal 100, and "B" indicates a process performed by the similar case retrieval application executed by the information terminal 100. In the following description, the medical information management application will be referred to as "Application A", and the similar case retrieval application will be referred to as "Application B".

First, Application A receives a request to display a reading target test list from the user and transmits the request to the medical information management system 200 (S510). Upon receiving the request to display a test list, the medical information management system 200 makes a list of tests for which imaging tests have been conducted but reading has not been performed. The medical information management system 200 then generates a test list to be read and transmits the test list to Application A.

Upon receiving the reading target test list, Application A displays the reading target test list on the display 101 as illustrated in FIG. 26. If the user selects one of the tests included in the reading target test list (S530), Application A transmits a request to display the selected test to the medical information management system 200 (S540).

Upon receiving the request to display the test, the medical information management system 200 transmits all slice images of all series included in a test ID specified by the request to display the test to Application A (S550).

Next, as illustrated in FIG. 27, Application A displays a series list for displaying information relating to all the series included in the specified test ID (S560).

Next, if the user selects a series to be read from the series list, Application A displays a slice image at a first slice position of the selected series on the distribution list display region 705 as illustrated in FIG. 4 (S570). At this time, the user displays a desired slice image on the medical image viewer 705 by performing an operation for displaying each slice image through scrolling.

Next, Application A receives, from the user, an operation for setting a ROI in the slice image displayed on the medical image viewer 705 (S580).

Next, Application A generates ROI information indicating the ROI set by the user and transmits the ROI information to Application B along with the slice image (slice image of a diagnosis target case) in which the ROI has been set (S590 and S600).

Next, upon receiving the slice image of a diagnosis target case and the ROI information, Application B transmits the slice image and the ROI information to the case retrieval system 300 (S601 and S602).

Upon receiving the slice image and the ROI information, the case retrieval system 300 performs the processing in S610 to S640 as in FIG. 28.

Next, Application B generates the initial base screen K2 using the similar case data transmitted in S640 as illustrated in FIG. 5 (S650). Application B then performs the processing in S651 and S652 as in FIG. 28.

Figure 37:
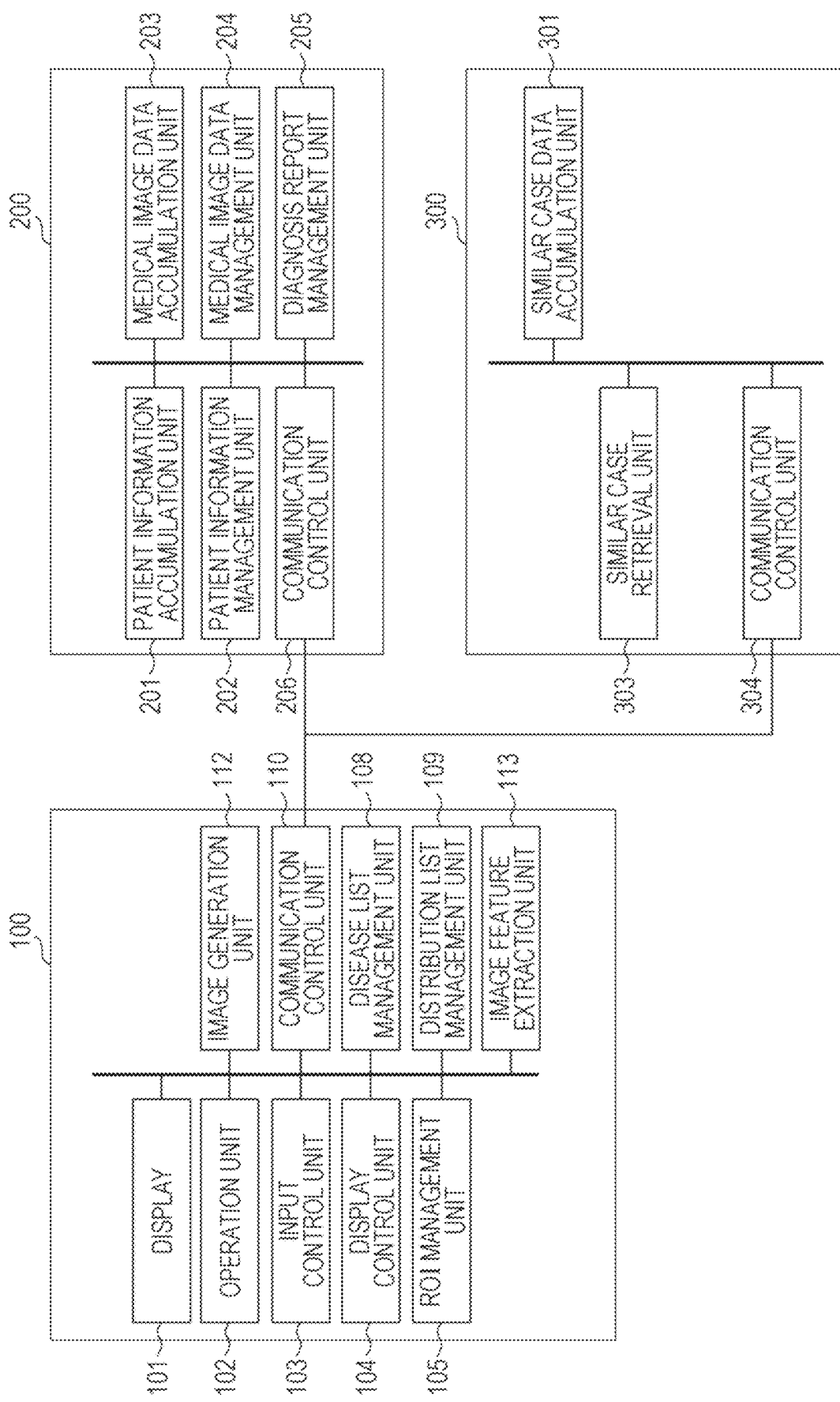
FIG. 37 is a block diagram illustrating the information terminal, the medical information management system, and the case retrieval system at a time when a mode in which the case retrieval system extracts an image feature is adopted.

Although an example in which the case retrieval system 300 extracts an image feature has been described above, the information terminal 100 may extract an image feature, instead. FIG. 37 is a block diagram illustrating the information terminal 100, the medical information management system 200, and the case retrieval system 300 at a time when a mode in which the case retrieval system 300 extracts an image feature is adopted.

Differences from FIG. 2 are that an image feature extraction unit 113 is added to the information terminal 100 and that the image feature extraction unit 302 is omitted from the case retrieval system 300.

Figure 38:
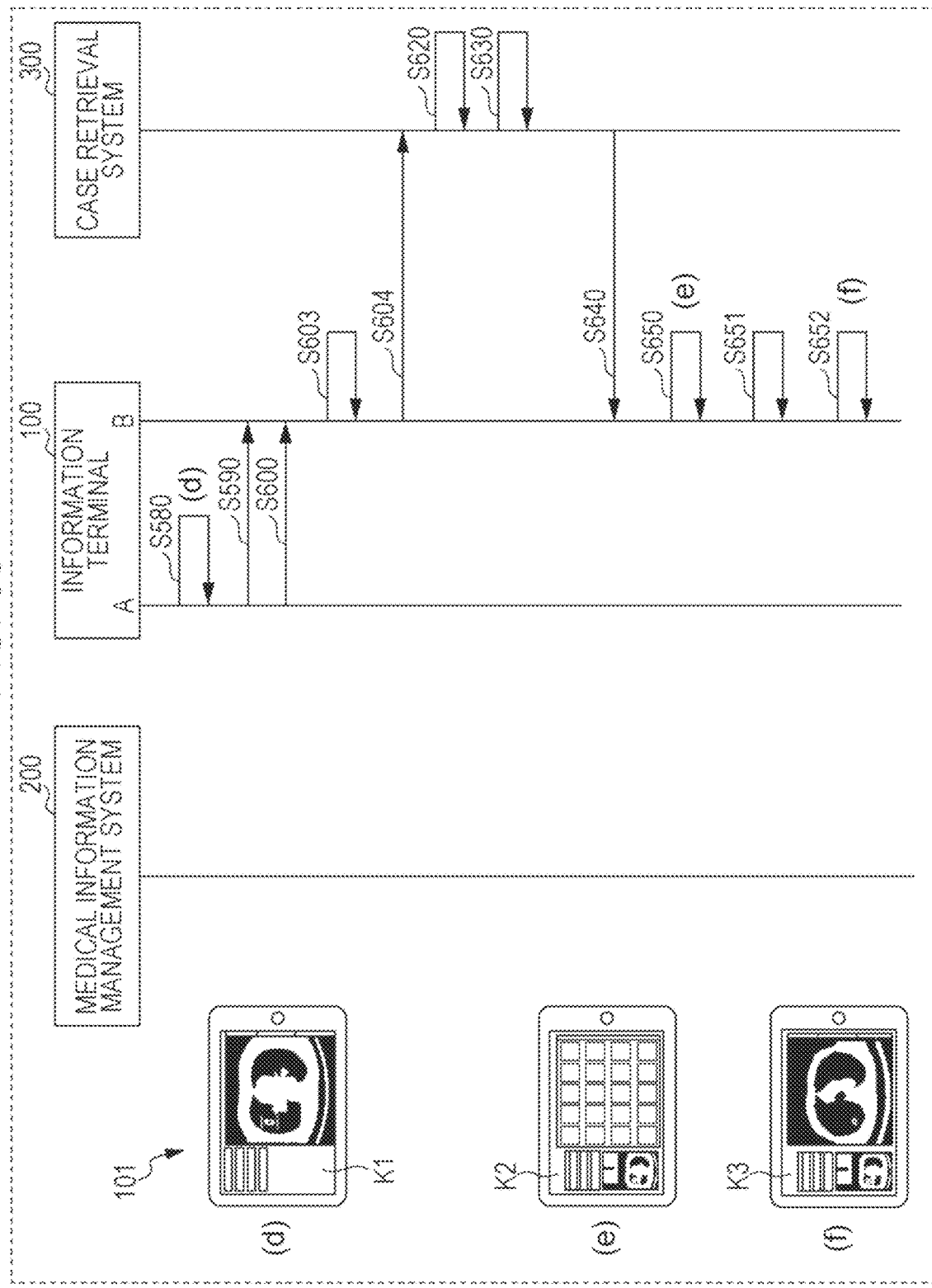
FIG. 38 is a sequence diagram illustrating a process performed in the configuration illustrated in FIG. 37 until the information terminal displays a base screen on the basis of results of retrieval of similar cases received from the case retrieval system after setting a region of interest.

FIG. 38 is a sequence diagram illustrating a process performed in the configuration illustrated in FIG. 37 until the information terminal 100 displays a base screen on the basis of results of retrieval of similar cases received from the case retrieval system 300 after the information terminal 100 sets a ROI.

A difference from FIGS. 25 and 28 is that after the ROI management unit 105 performs the process for transmitting a slice image of a diagnosis target case to the communication control unit 110 (S600), the information terminal 100 extracts an image feature (S603) and transmits the extracted image to the case retrieval system 300 (S604). The process for extracting an image feature (S604) is the same as that performed by the case retrieval system 300.

Figure 39:
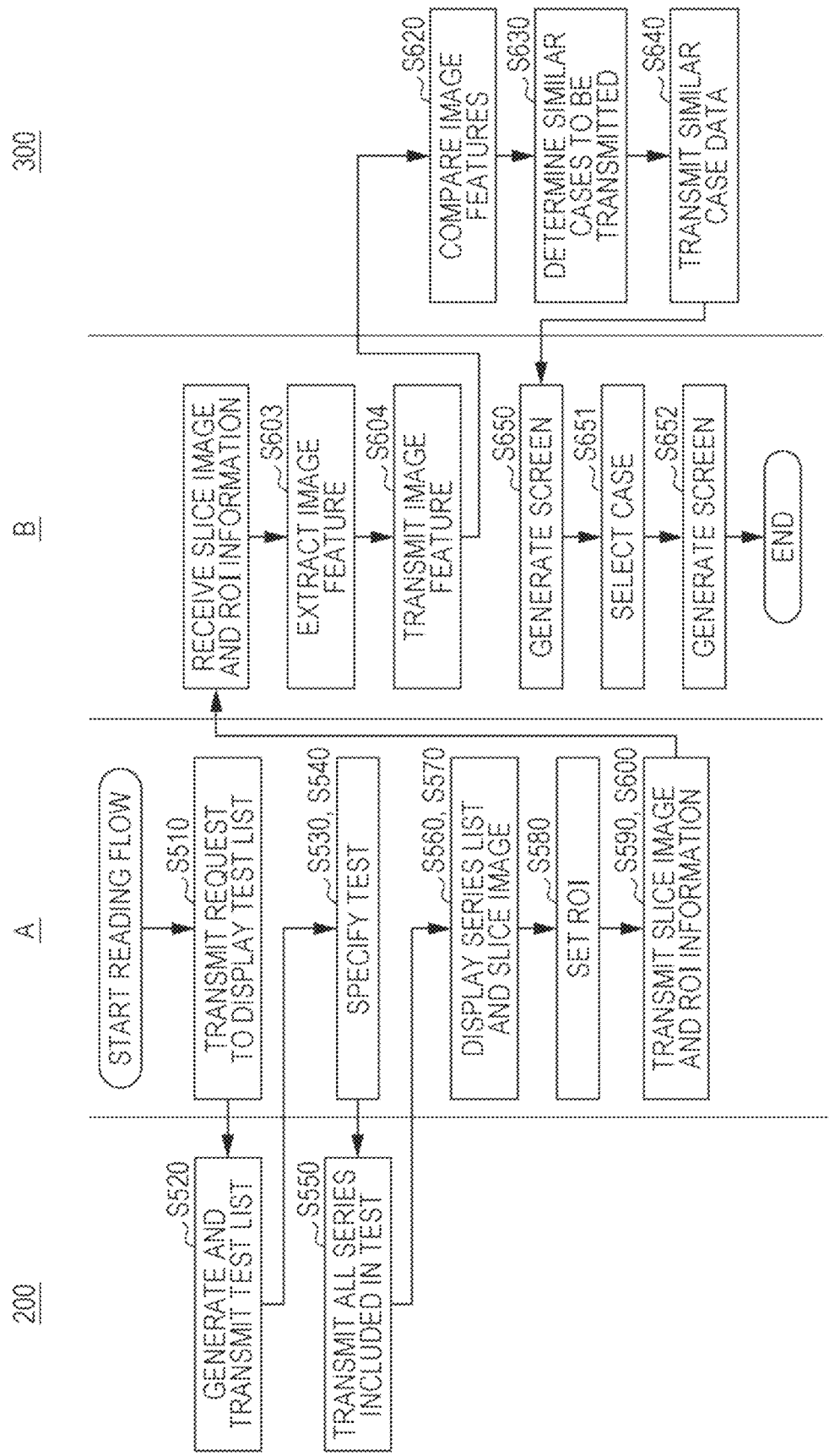
FIG. 39 is a sequence diagram at a time when a process performed in the configuration illustrated in FIG. 37 until the information terminal displays a base screen on the basis of results of retrieval of similar cases received from the case retrieval system after requesting the reading target test list from the medical information management system is seen at the level of the applications.

FIG. 39 is a sequence diagram at a time when the process performed in the configuration illustrated in FIG. 37 until the information terminal 100 displays a base screen on the basis of results of retrieval of similar cases received from the case retrieval system 300 after requesting the reading target test list from the medical information management system 200 is seen at the level of the applications. In FIG. 39, the same steps as those illustrated in FIGS. 25, 28, and 36 are given the same reference numerals.

In FIG. 39, "A" indicates a process performed by the medical information management application executed by the information terminal 100, and "B" indicates a process performed by the similar case retrieval application executed by the information terminal 100. In the following description, the medical information management application will be referred to as "Application A", and the similar case retrieval application will be referred to as "Application B".

Differences from FIG. 36 are in S603 and S604. In FIG. 39, the information terminal 100 extracts an image feature. Therefore, Application B extracts an image feature from a ROI set in a slice image of a diagnosis target case (S603) and transmits the extracted image feature to the case retrieval system 300 (S604).

Next, a process for switching a similar case displayed on the display 101 performed by the user by performing a swipe operation on the display 101 of the information terminal 100 will be described.

Figure 40:
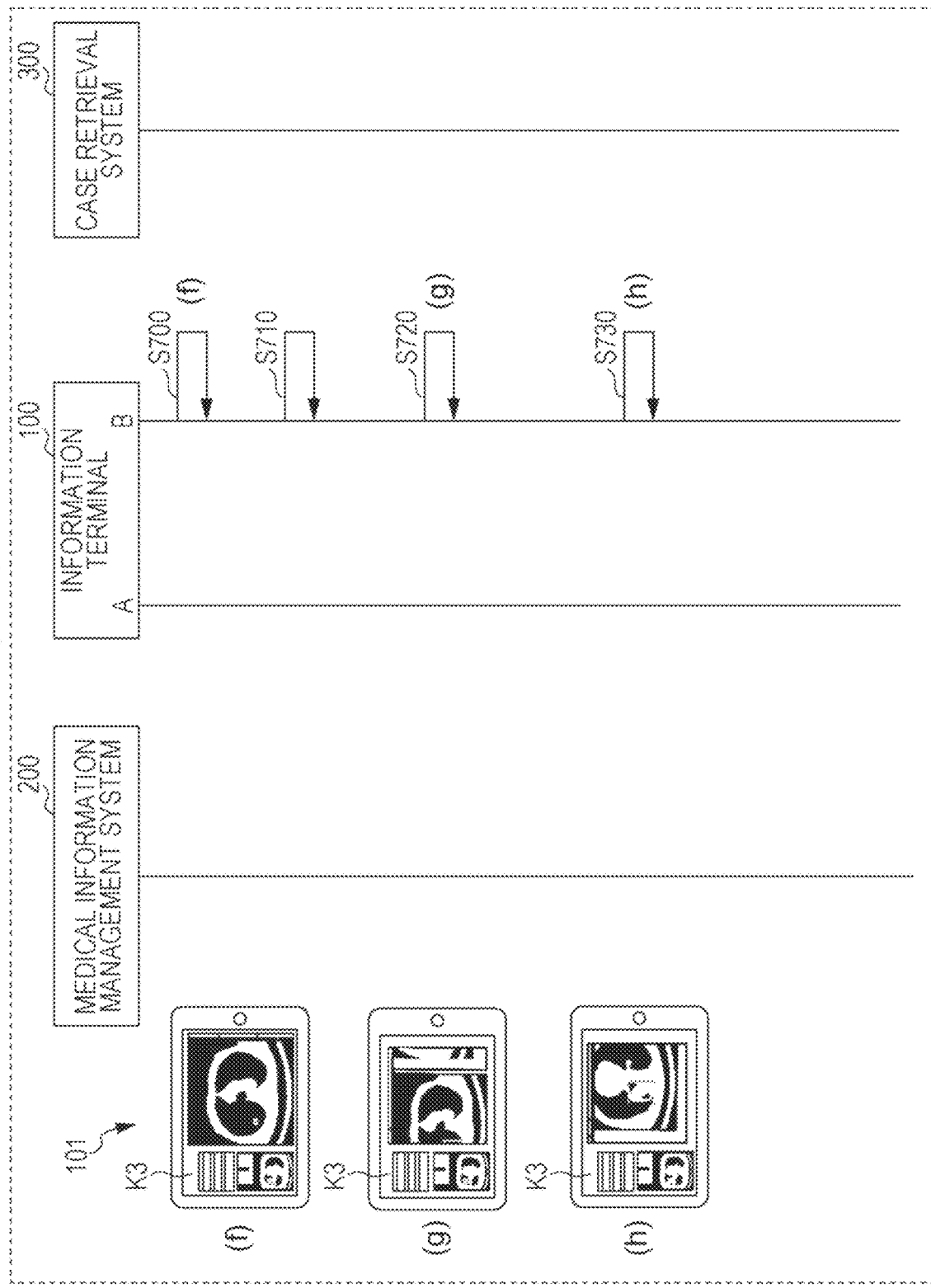
FIG. 40 is a sequence diagram illustrating a process for switching a similar case displayed on the display of the information terminal on the basis of a swipe operation.
Figure 41:
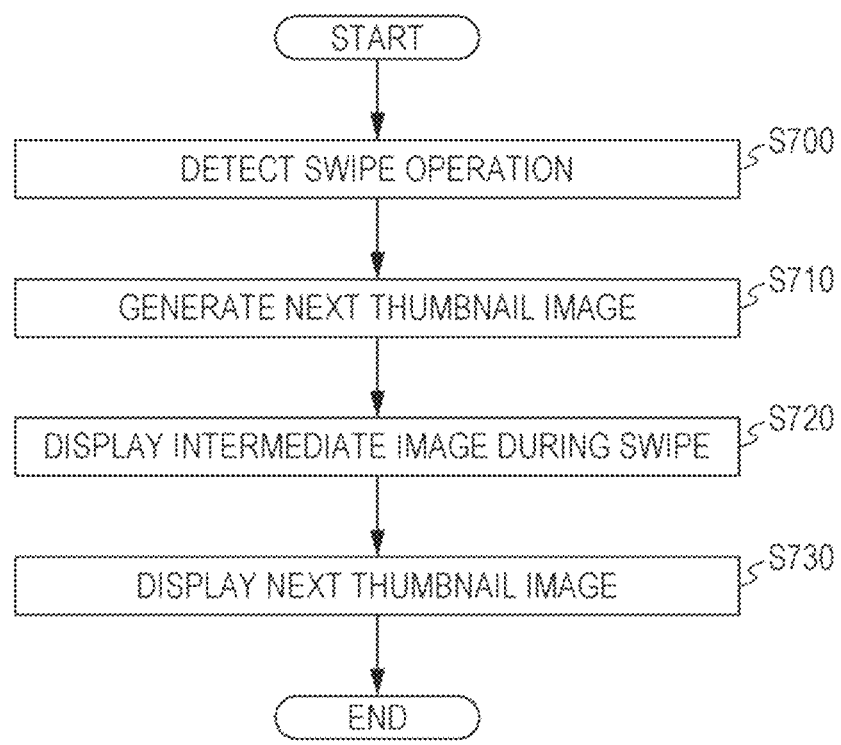
FIG. 41 is a flowchart illustrating the process corresponding to the sequence diagram of FIG. 40.

FIG. 40 is a sequence diagram illustrating the process for switching a similar case displayed on the display 101 of the information terminal 100 on the basis of a swipe operation. FIG. 41 is a flowchart illustrating the process corresponding to the sequence diagram of FIG. 40. FIGS. 42 to 47 are diagrams illustrating the base screen K3 in which a thumbnail image displayed in the case display region 710 is switched by a swipe operation performed by the user.

At a beginning of the process illustrated in FIGS. 40 and 41, the display 101 of the information terminal 100 displays the base screen K3 illustrated in FIG. 6A. The thumbnail image in the first row and the first column (that is, the thumbnail image of a similar case having the highest similarity) in the case display region 710 illustrated in FIG. 5 is displayed across the case display region 710 of the base screen K3 illustrated in FIG. 6A.

In S700 illustrated in FIGS. 40 and 41, first, the input control unit 103 of the information terminal 100 detects a swipe operation performed by the user. The input control unit 103 notifies the image generation unit 112 of the swipe operation.

Next, in S710, the image generation unit 112 generates a thumbnail image (that is, a thumbnail image in the first row and a second column in the case display region 710 illustrated in FIG. 5) of a similar case having second highest similarity on the basis of the notification from the input control unit 103. The image generation unit 112 outputs the generated thumbnail image to the display control unit 104.

Figure 42:
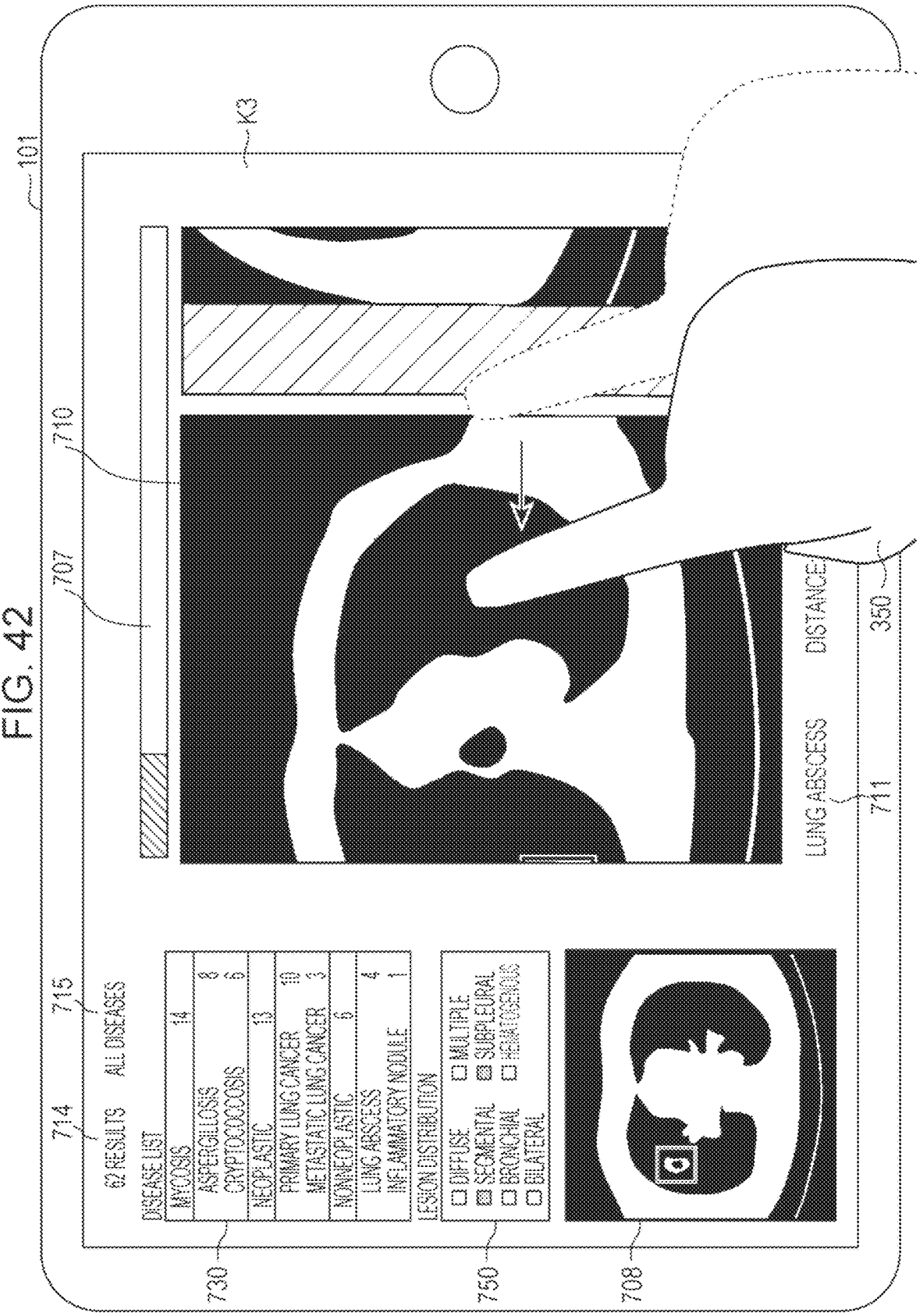
FIG. 42 is a diagram illustrating a base screen in which a thumbnail image displayed in a case display region is switched through a swipe operation performed by a user.
Figure 43:
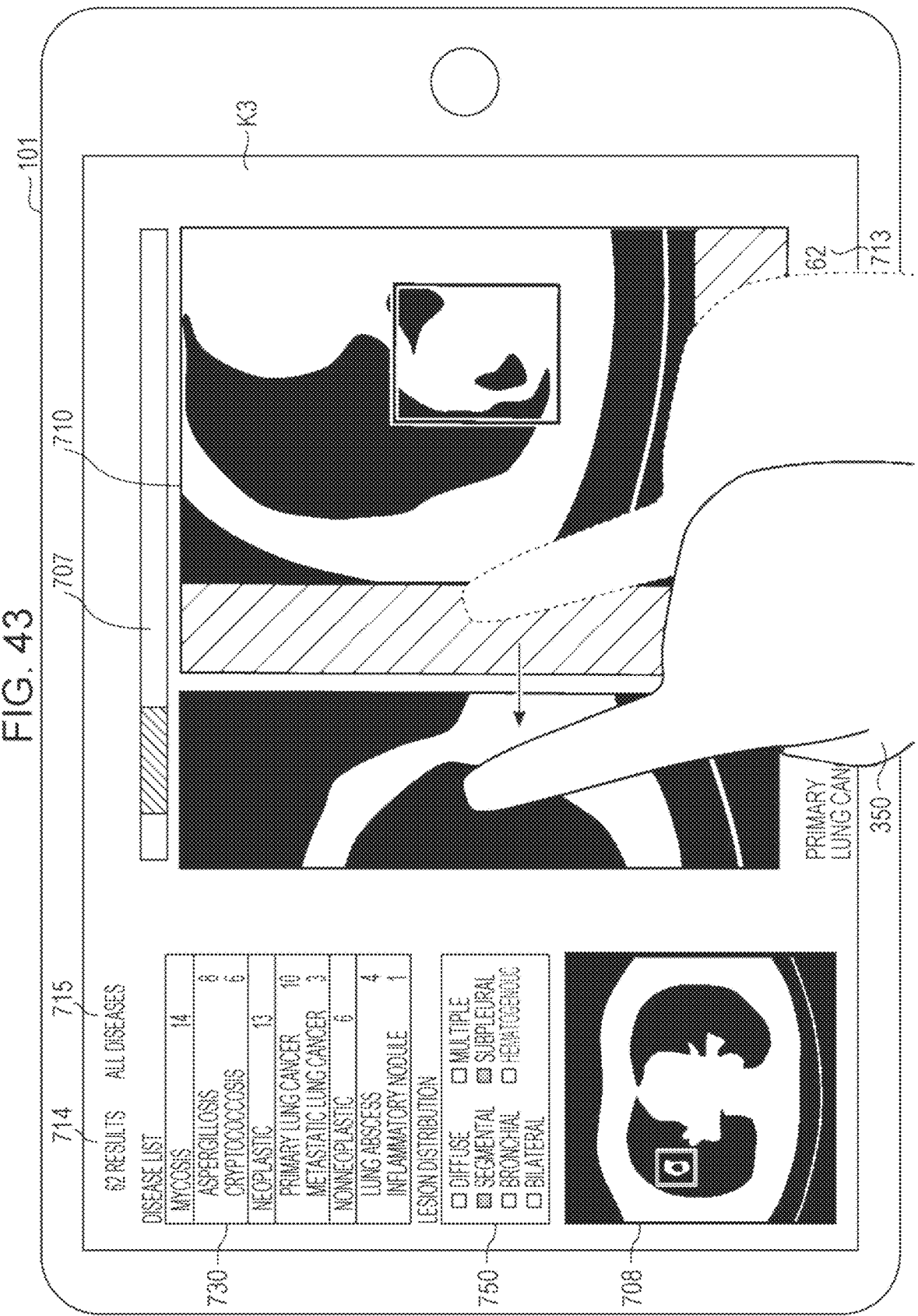
FIG. 43 is a diagram illustrating the base screen in which the thumbnail image displayed in the case display region is switched through the swipe operation performed by the user.

Next, in S720, the image generation unit 112 generates, as illustrated in FIGS. 42 and 43, an intermediate image, in which the thumbnail image before switching of the similar case and the thumbnail image after the switching are arranged adjacent to each other, during the swipe operation performed with an object 350 (the user's finger) so that the intermediate image appears in accordance with the swipe operation. The image generation unit 112 outputs the generated intermediate image to the display control unit 104. The display control unit 104 displays the intermediate image input from the image generation unit 112 in the case display region 710.

Figure 44:
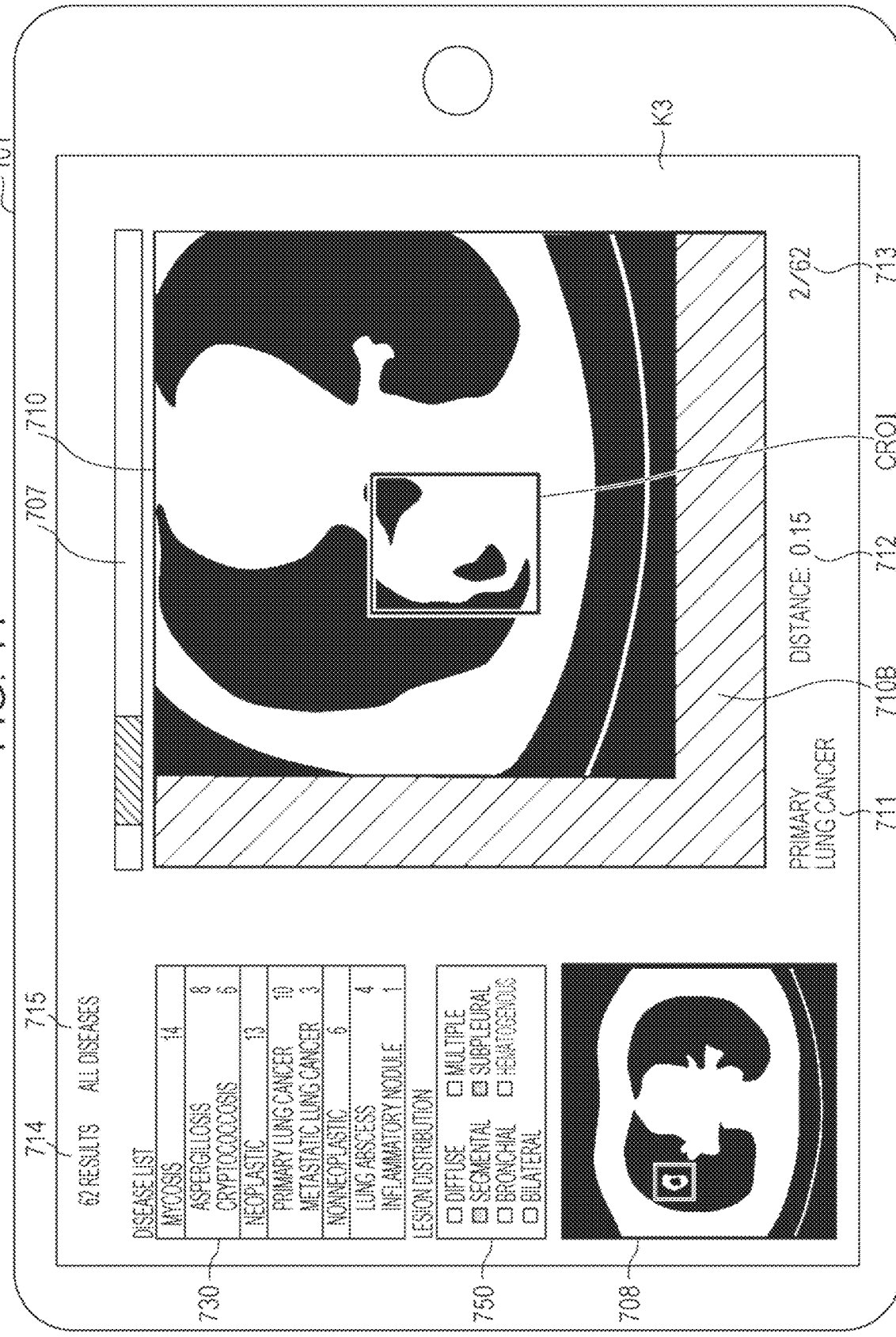
FIG. 44 is a diagram illustrating the base screen in which the thumbnail image displayed in the case display region is switched through the swipe operation performed by the user.

Next, in S730, after the swipe operation is completed, the display control unit 104 displays, as illustrated in FIG. 44, the thumbnail image of the similar case having the second highest similarity input from the image generation unit 112 in S710 across the case display region 710.

Figure 45:
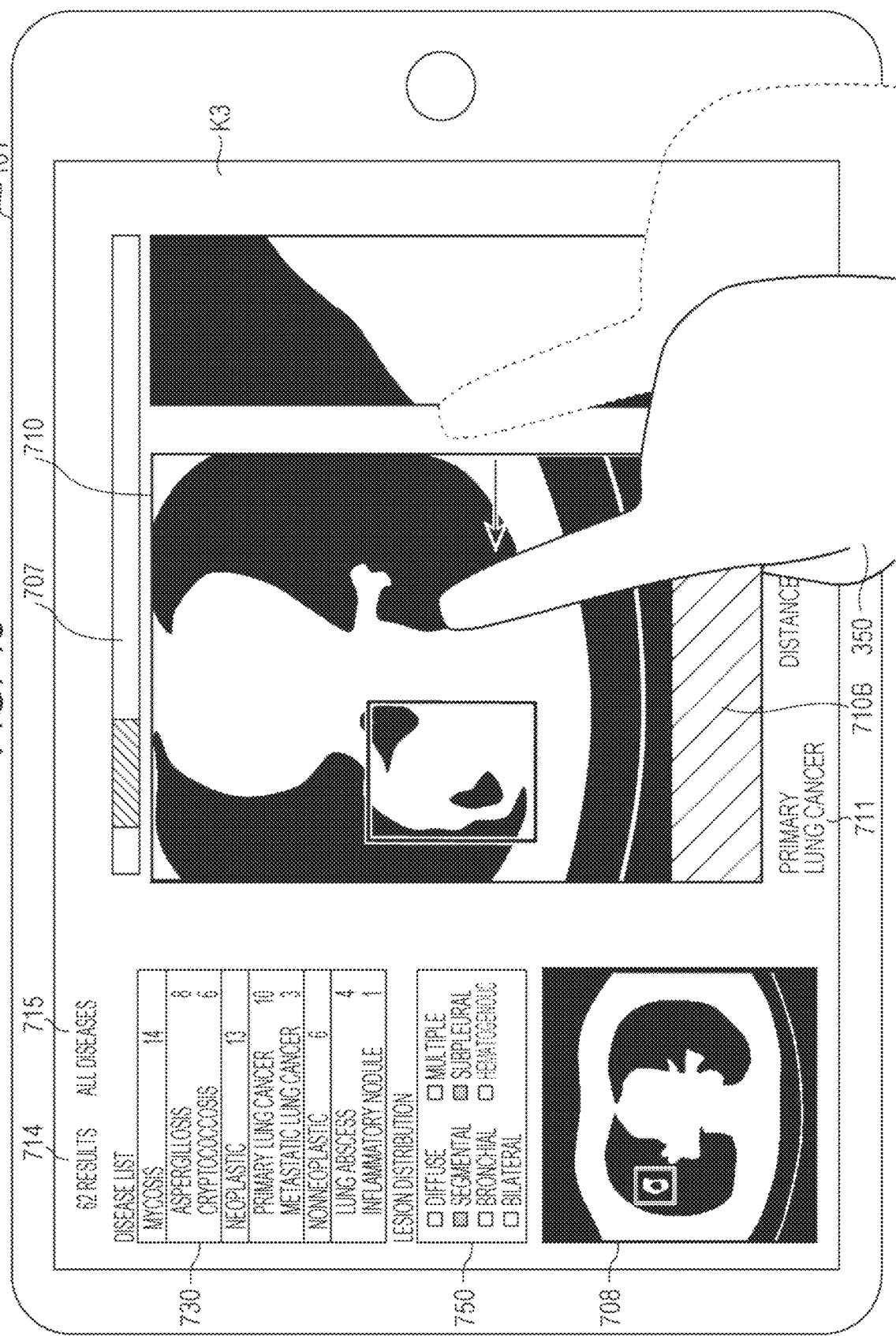
FIG. 45 is a diagram illustrating the base screen in which the thumbnail image displayed in the case display region is switched through the swipe operation performed by the user.
Figure 46:
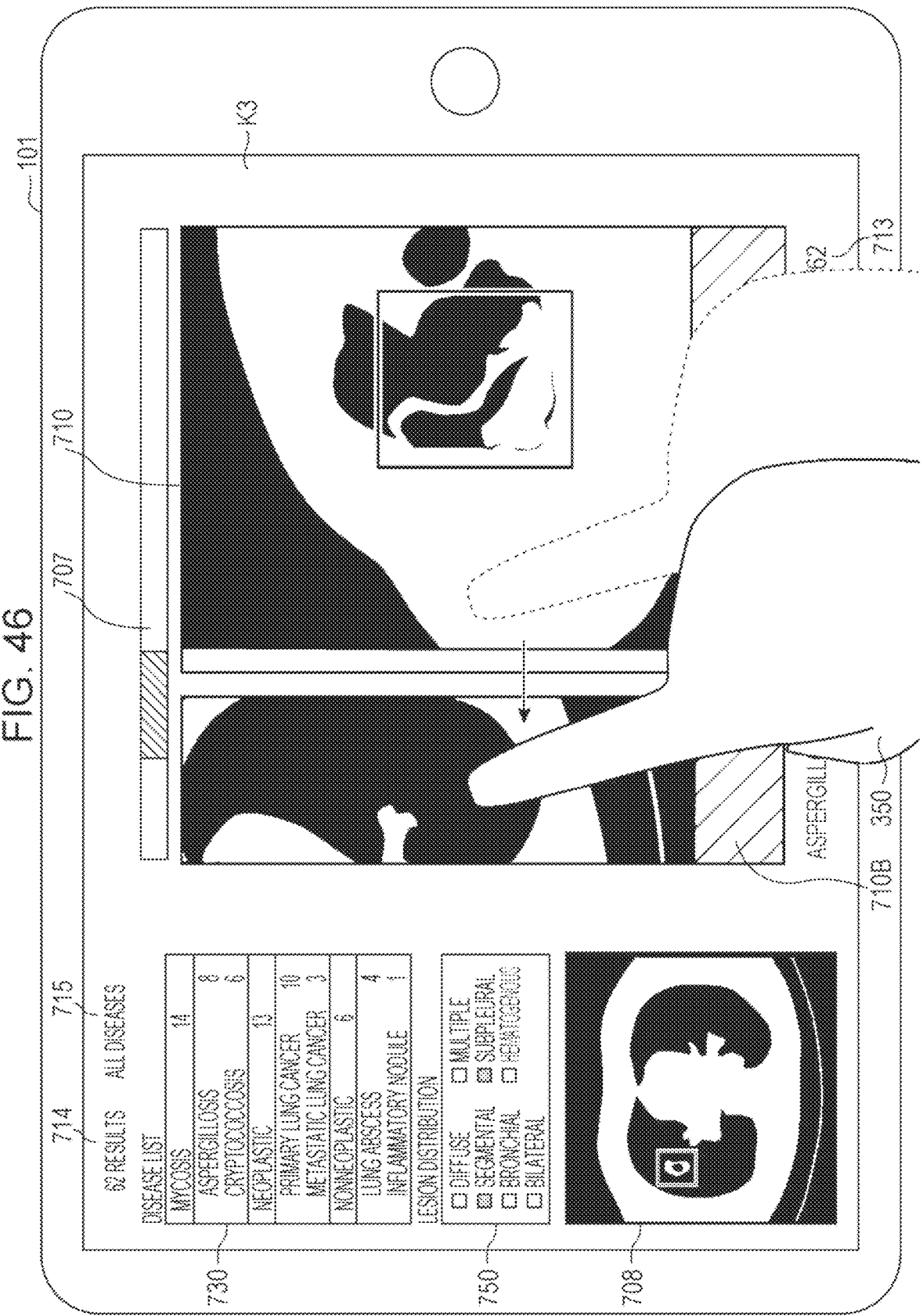
FIG. 46 is a diagram illustrating the base screen in which the thumbnail image displayed in the case display region is switched through the swipe operation performed by the user.

If the swipe operation is further performed with the base screen K3 illustrated in FIG. 44 displayed on the display 101, the display control unit 104 displays, as illustrated in FIGS. 45 and 46, an intermediate image in the case display region 710 in S720 after the processing in S700 and S710, which have been described above. Next, in S730, after the swipe operation is completed, the display control unit 104 displays, as illustrated in FIG. 47, a thumbnail image (a thumbnail image in the first row and a third column in the case display region 710 illustrated in FIG. 5) of a similar case having third highest similarity across the case display region 710.

Figure 47:
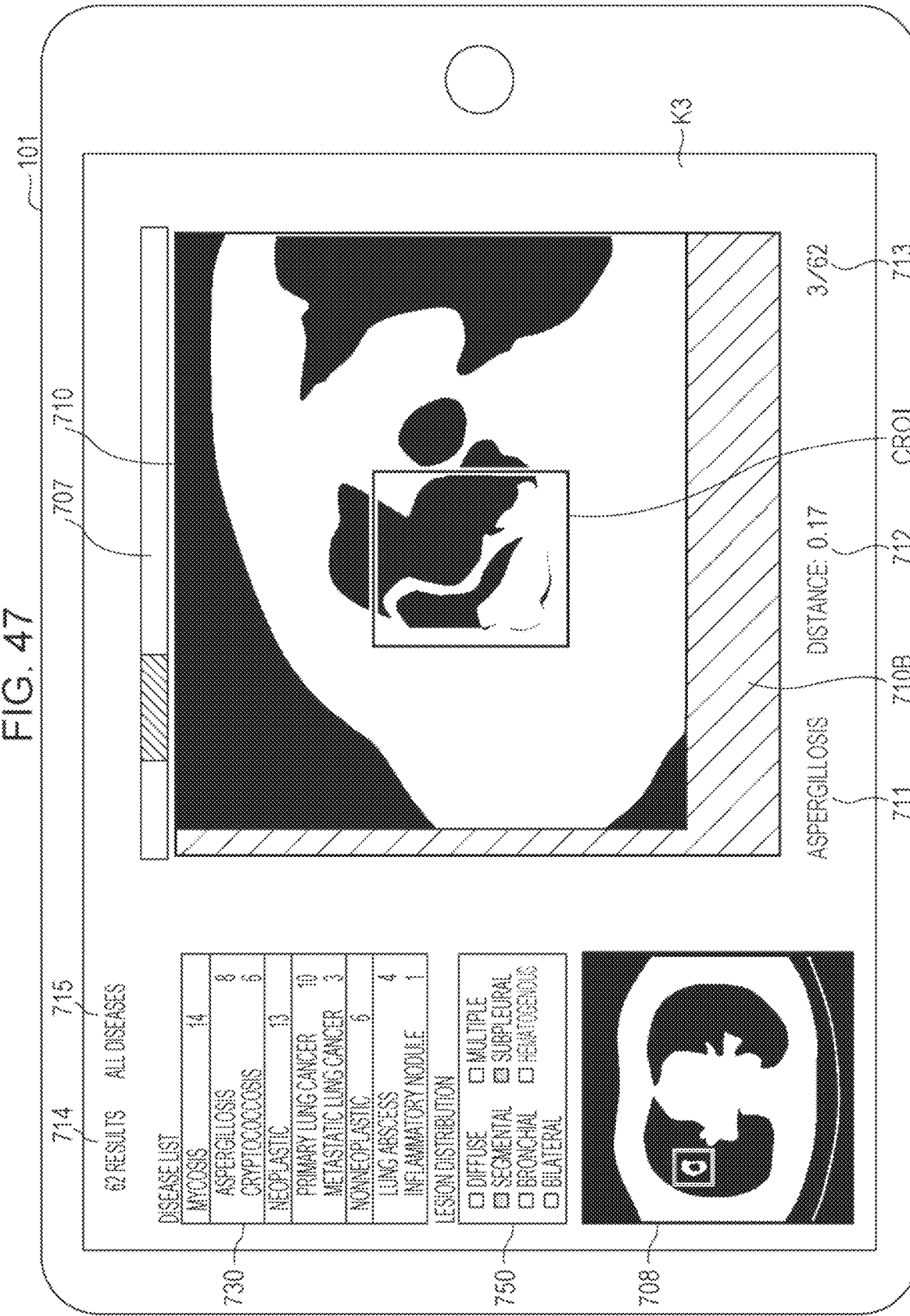
FIG. 47 is a diagram illustrating the base screen in which the thumbnail image displayed in the case display region is switched through the swipe operation performed by the user.

In the first embodiment, as illustrated in FIGS. 44 and 47, the display control unit 104 displays a thumbnail image while adjusting a position of the thumbnail image such that the center of a CROI matches the center of the case display region 710 during the swipe operation. As illustrated in FIGS. 44 and 47, the display control unit 104 displays a background image in a region 710B, which is a region inside the case display region 710 but outside the thumbnail image. The background image may be grey, or may be white or black. Thus, the region 710B can be identified. In the following description, details of a process for generating a thumbnail image illustrated in FIG. 44 or 47 performed by the image generation unit 112 will be described with reference to FIG. 48.

Figure 48:
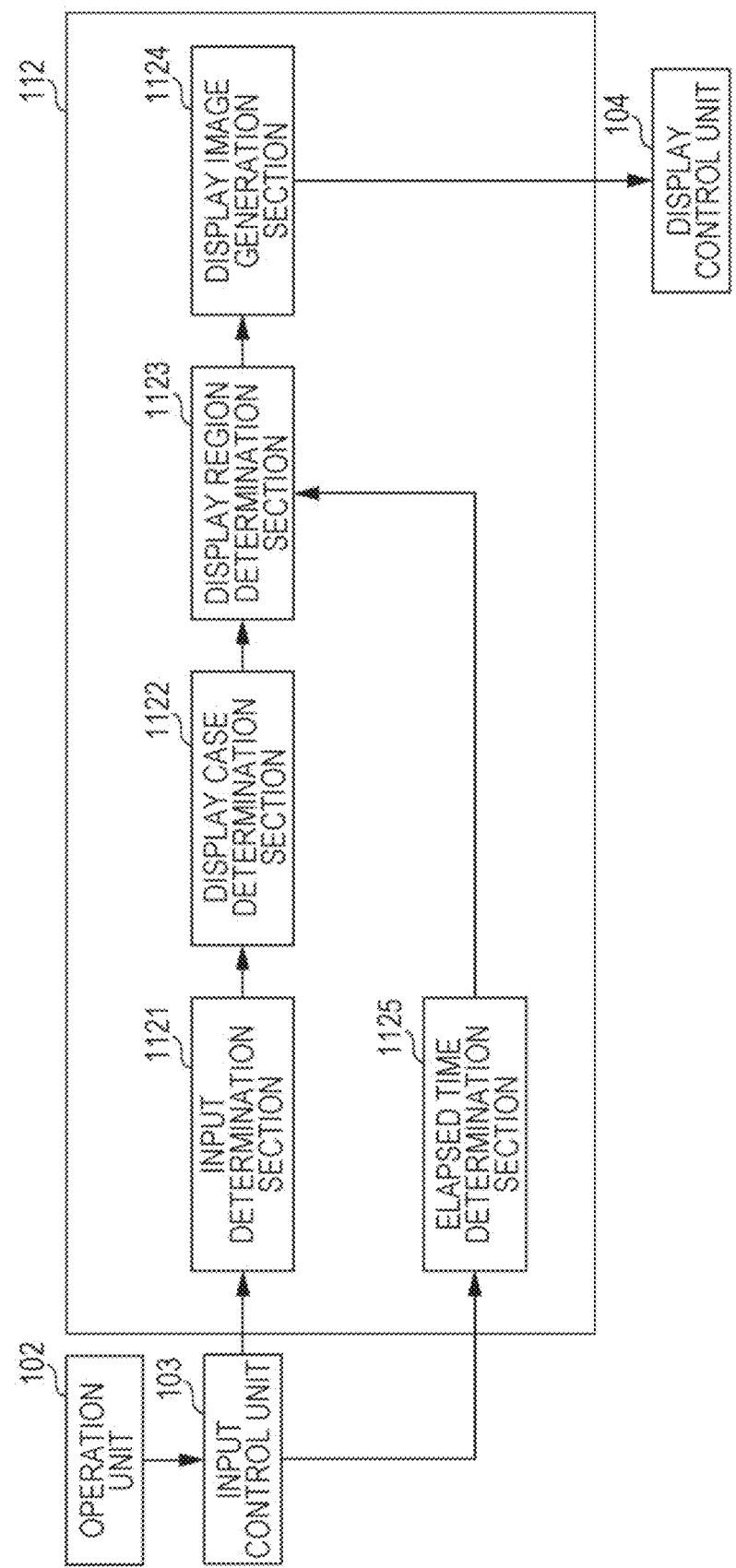
FIG. 48 is a block diagram illustrating a detailed configuration of an image generation unit.

FIG. 48 is a block diagram illustrating a detailed configuration of the image generation unit 112. The image generation unit 112 includes an input determination section 1121, a display case determination section 1122, a display region determination section 1123, a display image generation section 1124, and an elapsed time determination section 1125. The display 101 of the information terminal 100 displays the base screen K3 illustrated in FIG. 6A.

If the input control unit 103 detects an operation performed by the user using the operation unit 102, the input control unit 103 outputs a result of the detection to the input determination section 1121. The input determination section 1121 determines whether the operation performed by the user using the operation unit 102 is a swipe operation on the basis of the result of the detection input from the input control unit 103. If the input determination section 1121 determines that the operation is a swipe operation, the input determination section 1121 outputs information indicating that the operation is a swipe operation and a direction of the swipe operation (for example, leftward or rightward) to the display case determination section 1122.

The display case determination section 1122 refers to the similar case ID 4100 (FIG. 23) and the distance calculated by the similar case retrieval unit 303 corresponding to a similar case displayed in the case display region 710. If the direction of the swipe operation input from the input determination section 1121 is leftward, the display case determination section 1122 obtains a similar case ID of a similar case whose having shortest distance next to that of the similar case currently displayed in the case display region 710 (that is, a similar case having highest similarity next to that of the current similar case).

On the other hand, if the direction of the swipe operation input from the input determination section 1121 is rightward, the display case determination section 1122 obtains a similar case ID of a similar case having longest distance next to that of the similar case currently displayed in the case display region 710 (that is, a similar case having higher similarity than the current similar case).

The display case determination section 1122 determines a similar case corresponding to the obtained similar case ID as a similar case to be displayed next. If the display case determination section 1122 does not obtain a similar case ID, the display case determination section 1122 determines the currently displayed similar case as the similar case to be displayed next. That is, the similar case displayed in the case display region 710 remains the same. For example, even if a rightward swipe operation is performed with the base screen K3 illustrated in FIG. 6A displayed, the display screen does not change because the similarity of the similar case currently displayed in the case display region 710 is the highest.

The display region determination section 1123 refers to the ROI information 4300 (FIG. 23) of the similar case data 4000 regarding the similar case determined by the display case determination section 1122. The display region determination section 1123 determines coordinates of a display region of a thumbnail image of the similar case such that the center coordinates of the CROI match the center of the case display region 710.

Figure 49:
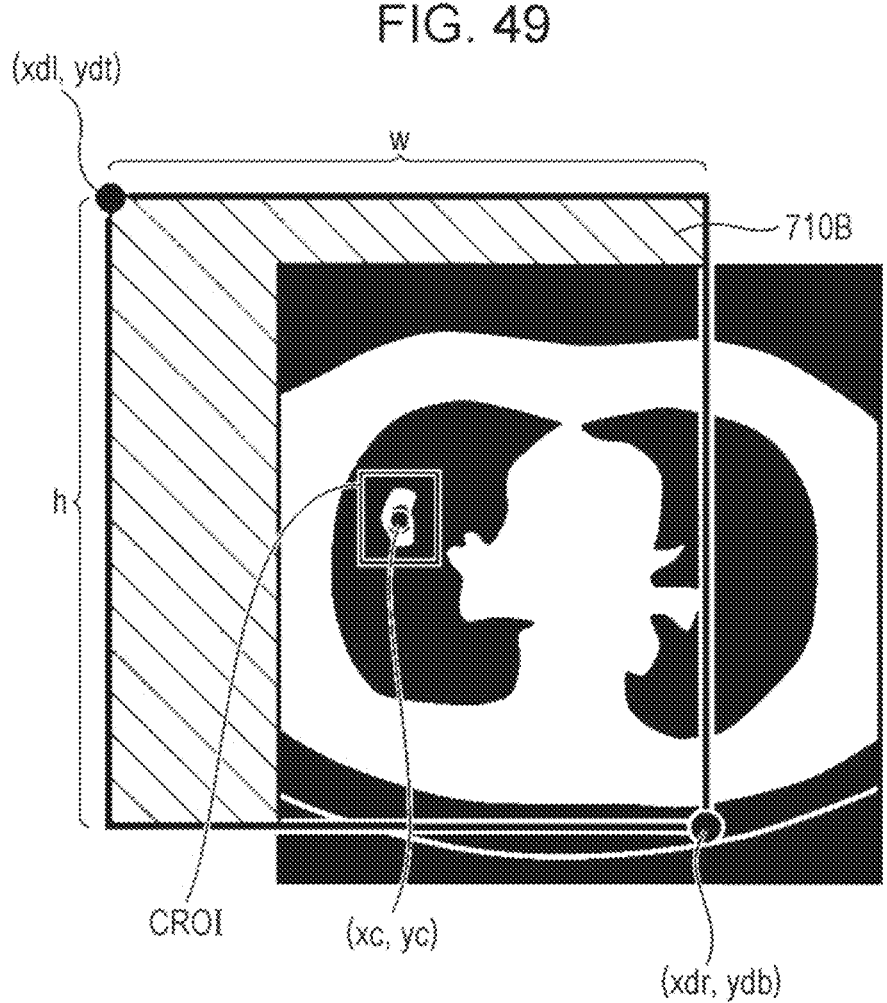
FIG. 49 is a diagram schematically illustrating coordinates of a display region determined by a display region determination section.

FIG. 49 is a diagram schematically illustrating the coordinates of the display region determined by the display region determination section 1123. Coordinates (xdl, ydt) of an upper-left corner of the display region and coordinates (xdr, ydb) of a lower-right corner of the display region illustrated in FIG. 49 can be calculated using the following expression using center coordinates (xc, yc) of the CROI and a vertical dimension h and a horizontal direction w of the display region.

$xdl=xc-w/2$ $ydt=yc-h/2$ $xdr=xc+w/2$ $ydb=yc+h/2$

At this time, if the coordinates (xdl, ydt) or (xdr, ydb) of the display region are outside the original thumbnail image (for example, negative values), the display region may be displayed, as described above, in black as a background image whose pixel values are 0. Alternatively, the user may specify color. In FIG. 49, the coordinates (xdl, ydt) of the upper-left corner are outside the original thumbnail image, and the background image is displayed in the region 710B.

The display image generation section 1124 generates an image to be displayed in the case display region 710 on the basis of the coordinates of the display region determined by the display region determination section 1123 and the thumbnail image of the similar case determined by the display case determination section 1122. The display image generation section 1124 outputs the generated image to the display control unit 104.

As a result of the above process, even if a thumbnail image displayed in the case display region 710 is switched to a next thumbnail image, the next thumbnail image is displayed such that the CROI is located at the center of the case display region 710.

The position of the CROI of each similar case is usually different. Therefore, if a thumbnail image is switched without making any adjustment, a doctor needs to visually search for the CROI. When there are many images, this operation might be physically exhausting.

On the other hand, according to the first embodiment, the doctor does not need to visually search for the CROI each time a new thumbnail image of a similar case is displayed. Therefore, the doctor can observe the CROI immediately. As a result, when thumbnail images of a plurality of similar cases are sequentially observed through a swipe operation, the observation can be less exhausting and a reading efficiency improves, thereby improving an efficiency of diagnosis.

Next, a process when the user has not performed a swipe operation for a certain period of time after switching a thumbnail image of a similar case displayed in the case display region 710 by performing a swipe operation on the display 101 of the information terminal 100 will be described with reference to FIGS. 48 and 50.

Figure 50:
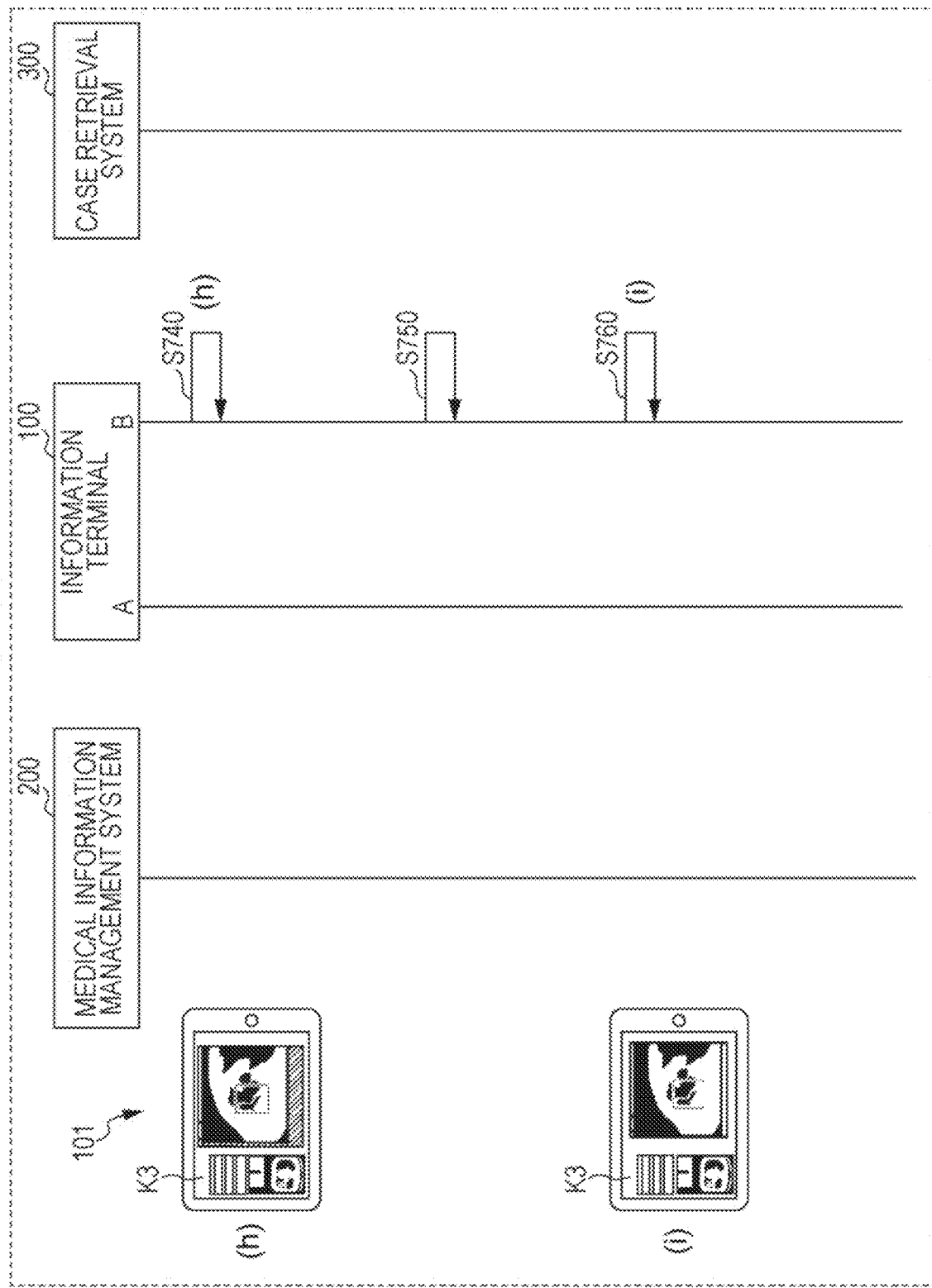
FIG. 50 is a sequence diagram illustrating a process performed when the user has not performed a swipe operation for a certain period of time after switching a thumbnail image of a similar case by performing a swipe operation on the information terminal.

FIG. 50 is a sequence diagram illustrating a process performed when the user has not performed a swipe operation for a certain period of time after switching a thumbnail image of a similar case by performing a swipe operation on the information terminal 100.

In FIG. 48, the input control unit 103 outputs a detection signal to the elapsed time determination section 1125 each time the input control unit 103 detects a swipe operation. The elapsed time determination section 1125 measures time elapsed since a last swipe operation performed by the user on the basis of the detection signal from the input control unit 103. If the elapsed time exceeds a predetermined threshold (for example, 10 seconds), the elapsed time determination section 1125 outputs an elapsed signal indicating the excess to the display region determination section 1123.

In S740 illustrated in FIG. 50, if the elapsed time determination section 1125 outputs the elapsed signal to the display region determination section 1123, the display region determination section 1123 begins a process for changing the display region of a thumbnail image displayed in the case display region 710. The image generation unit 1123 determines the display region of a thumbnail image such that the center of the original thumbnail image matches the center of the case display region 710.

Next, in S750, the display image generation section 1124 generates the original thumbnail image on the basis of the display region determined by the display region determination section 1123. The display image generation section 1124 outputs the generated original thumbnail image to the display control unit 104.

Next, in S760, the display control unit 104 displays the thumbnail image generated by the elapsed time determination section 1125 in the case display region 710 of the display 101.

Figure 51:
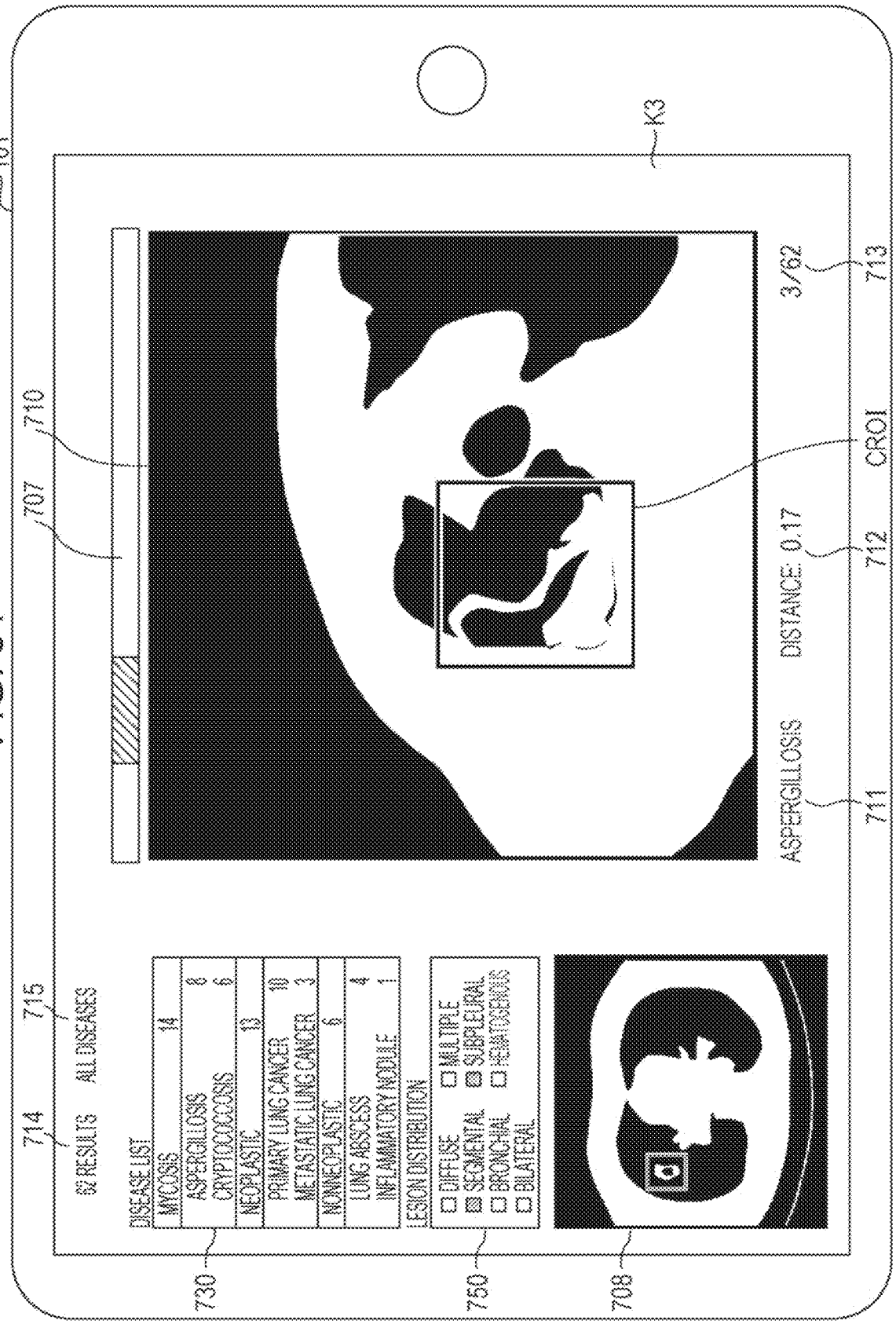
FIG. 51 is a diagram illustrating an example of a base screen displayed on the display in the sequence illustrated in FIG. 50.
Figure 52:
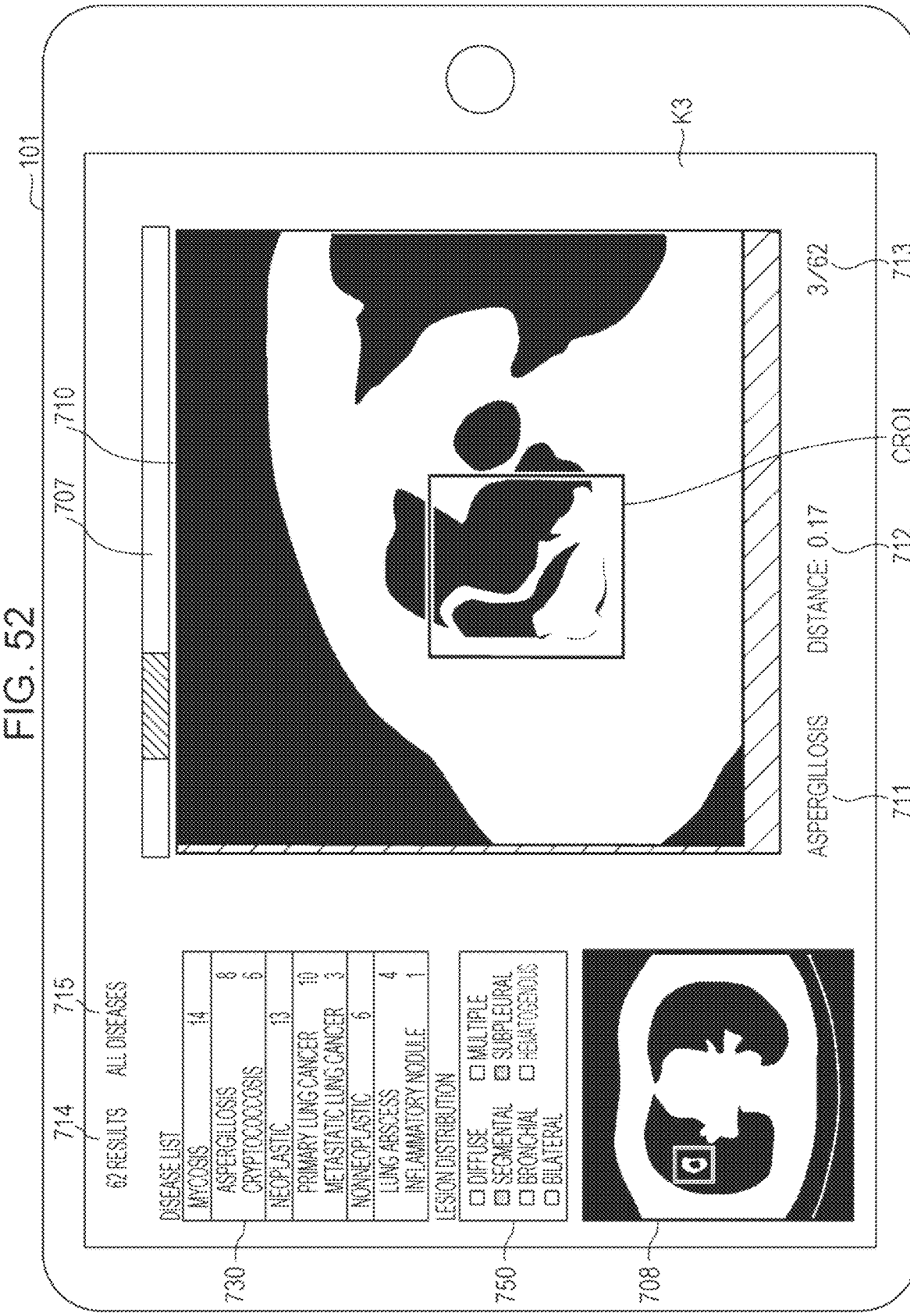
FIG. 52 is a diagram illustrating an example of the base screen displayed on the display in the sequence illustrated in FIG. 50.

FIGS. 51 and 52 are diagrams illustrating examples of the base screen K3 displayed on the display 101 in the sequence illustrated in FIG. 50.

In S740 illustrated in FIG. 50, the base screen K3 illustrated in FIG. 47 after the last swipe operation is completed is displayed on the display 101.

If the time elapsed since the last swipe operation exceeds the threshold (for example, 10 seconds) without another swipe operation, the base screen K3 illustrated in FIG. 51, in which the display region is determined such that the center of the original thumbnail image matches the center of the case display region 710, is displayed on the display 101.

If the center position is suddenly changed from that in the base screen K3 illustrated in FIG. 47 to that in the base screen K3 illustrated in FIG. 51, the doctor might need to search for the CROI, which is undesirable. Therefore, if the center position is reset to that in the original thumbnail image, the image generation unit 112 may generate, as illustrated in FIG. 52, a thumbnail image whose display region is somewhere between that of the thumbnail image illustrated in FIG. 47 and that of the thumbnail image illustrated in FIG. 51. The display control unit 104 may then display the generated thumbnail image on the display 101. Alternatively, not only the thumbnail image illustrated in FIG. 52 but also a plurality of thumbnail images may be displayed between the state illustrated in FIG. 47 and the state illustrated in FIG. 51. In this case, the processing from S740 to S760 illustrated in FIG. 10 may be repeated a plurality of times to generate a plurality of thumbnail images. As a result, the center position of a thumbnail image can be smoothly changed.

When a swipe operation is not performed, the user might be closely looking at a current image. Therefore, the user might desire to check the entirety of the image. For this reason, in the first embodiment, as described with reference to FIG. 47 and FIGS. 50 to 52, if the time elapsed since the last swipe operation exceeds the threshold (for example, 10 seconds), the base screen K3 in which the center of the original thumbnail image matches the center pf the case display region 710 is displayed on the display 101. As a result, the number of operations performed to view the entirety of a thumbnail image can be decreased.

Second Embodiment

Next, a second embodiment will be described. In the second embodiment, the user enlarges a thumbnail image of a similar case displayed on the information terminal 100 and then performs a swipe operation to switch the displayed thumbnail image of the similar case.

Figure 53:
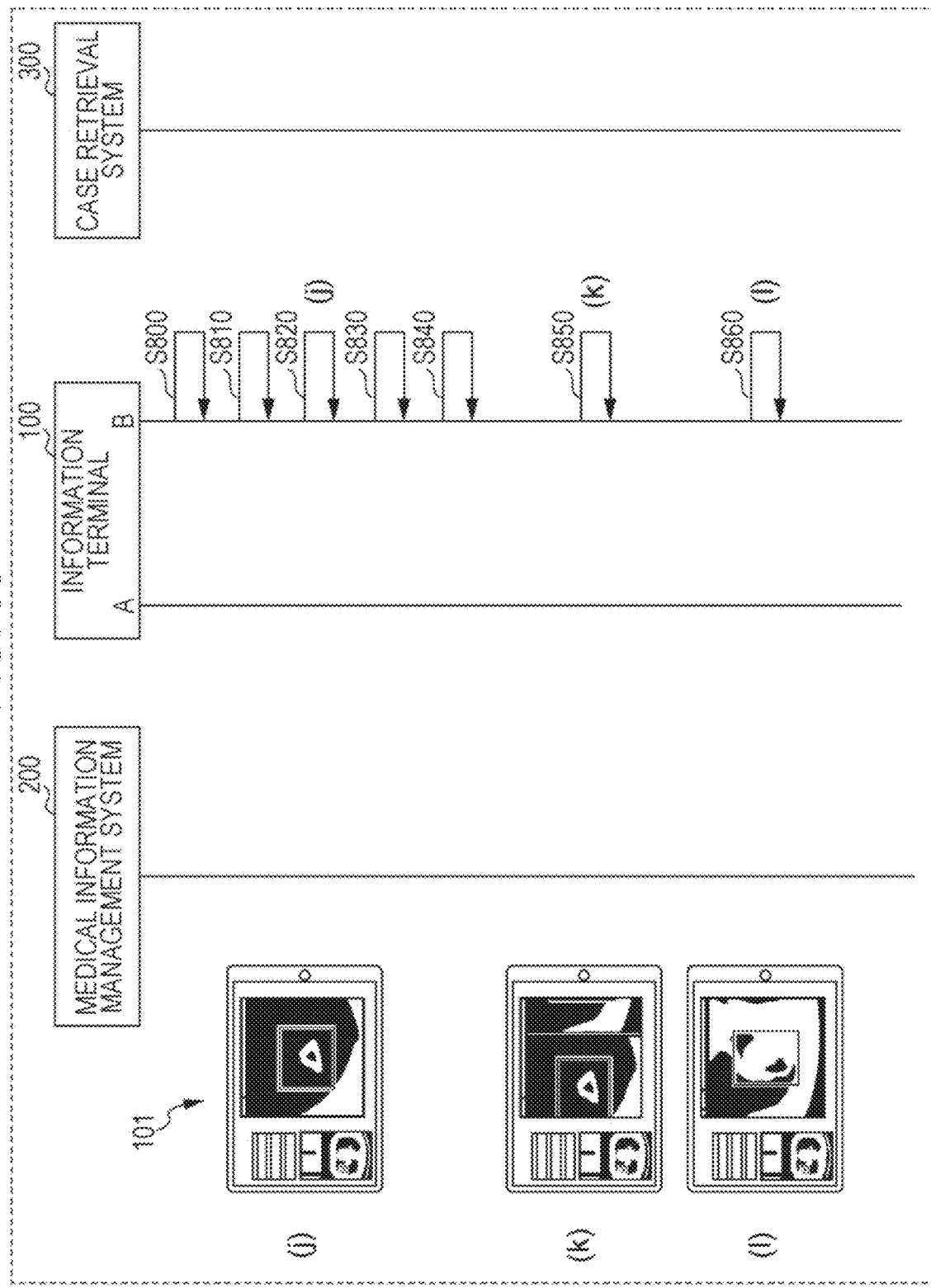
FIG. 53 is a sequence diagram illustrating a process performed until a thumbnail image of a next similar case is displayed after the user performs an enlargement operation.
Figure 54:
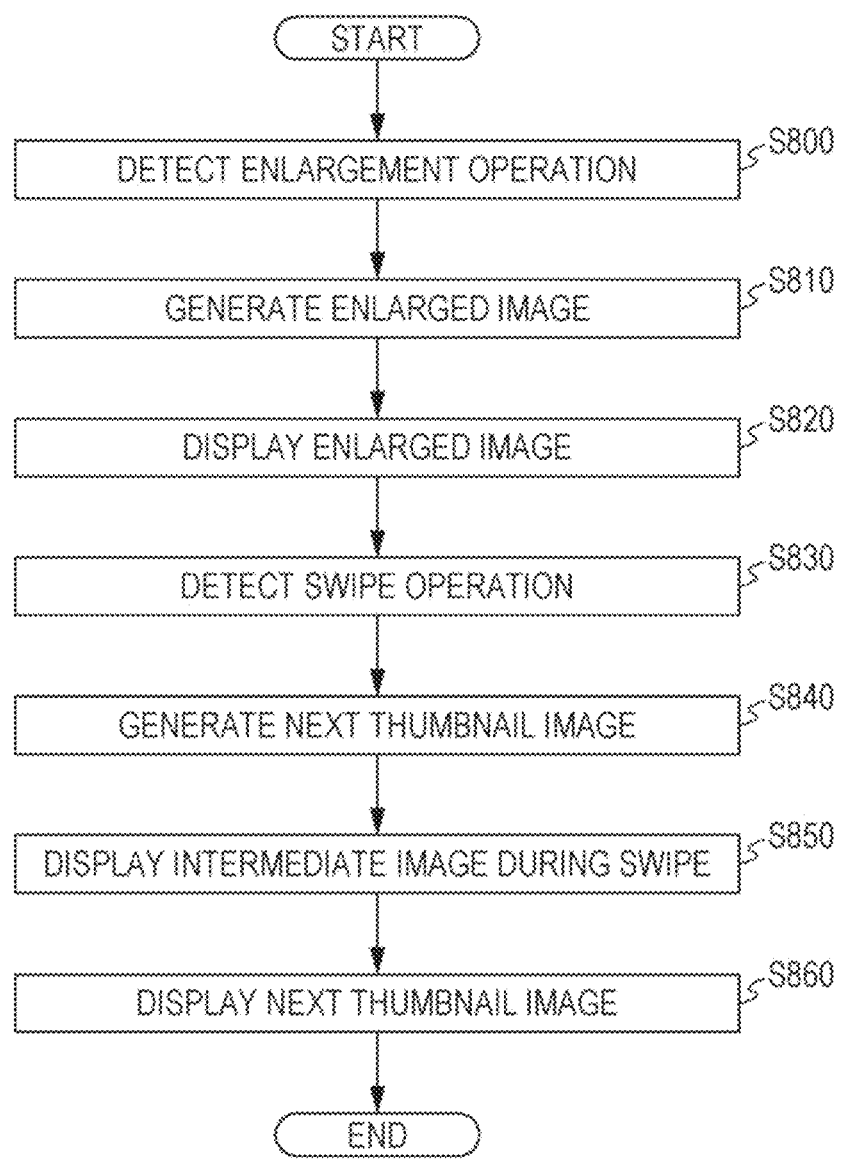
FIG. 54 is a flowchart illustrating the process corresponding to the sequence diagram of FIG. 53.
Figure 55:
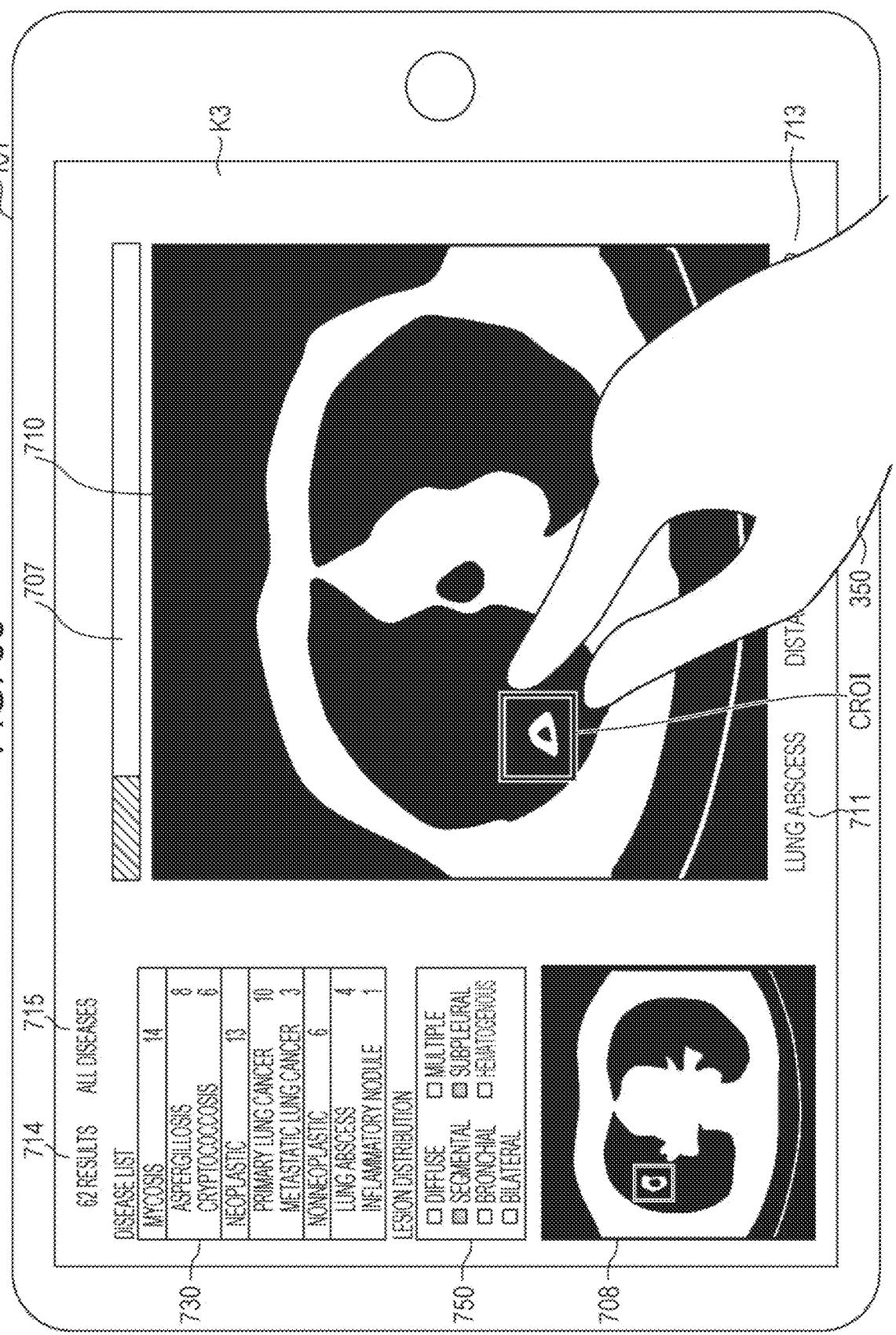
FIG. 55 is a diagram illustrating a pinch-out operation performed by the user on a thumbnail image.
Figure 56:
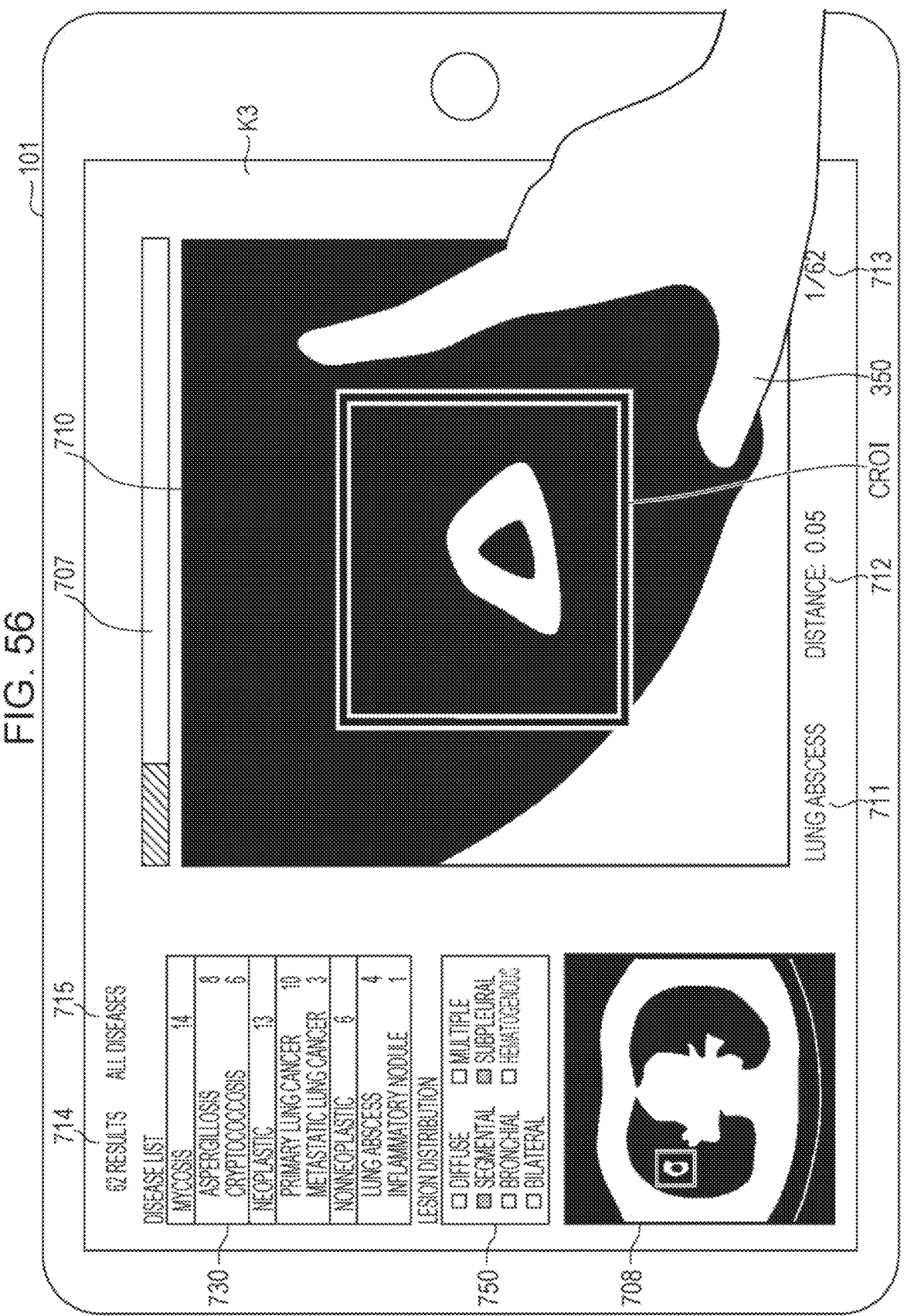
FIG. 56 is a diagram illustrating the pinch-out operation performed by the user on the thumbnail image.
Figure 57:
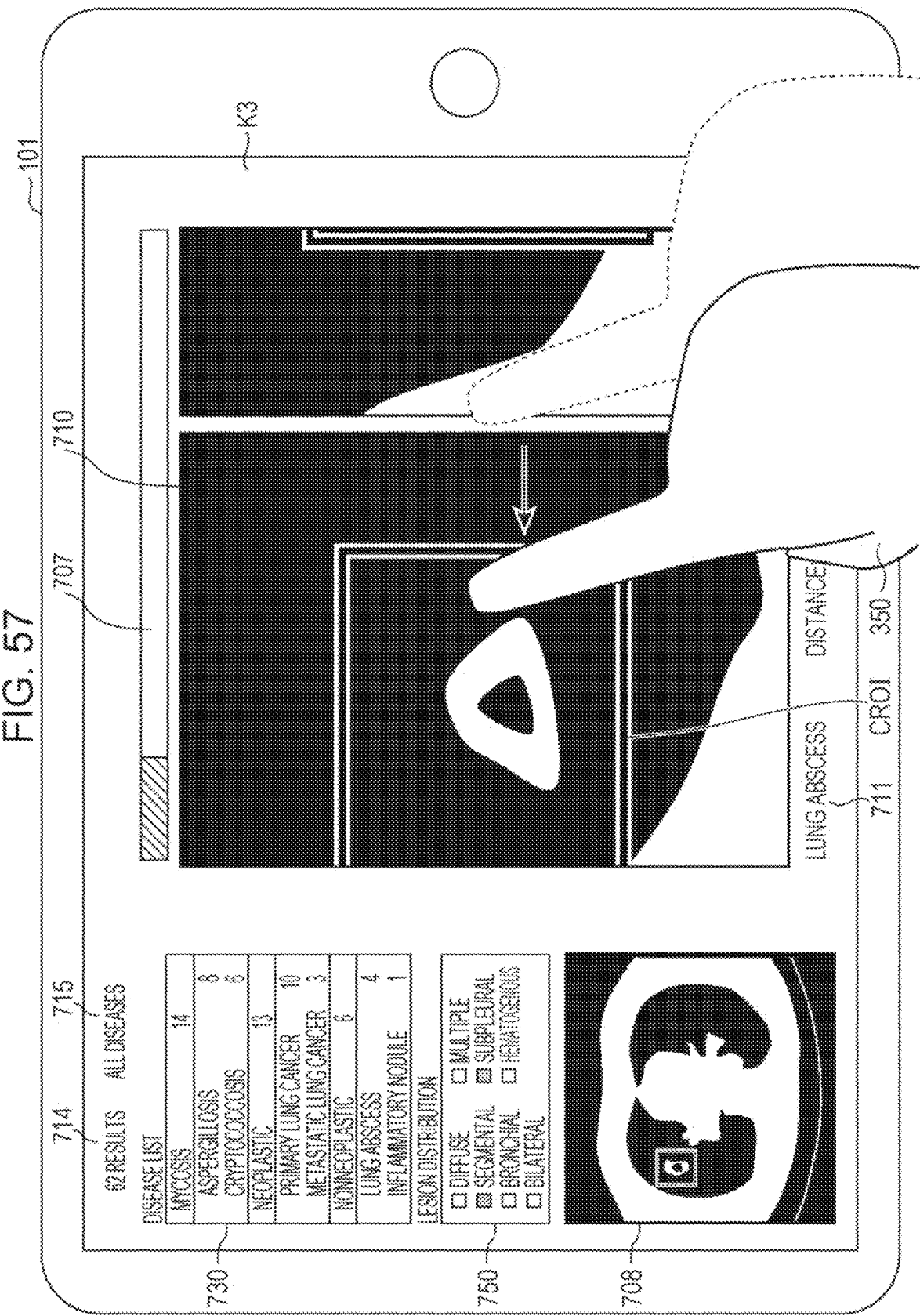
FIG. 57 is a diagram illustrating a base screen in which a thumbnail image displayed in the case display region is switched through a swipe operation performed by the user.
Figure 58:
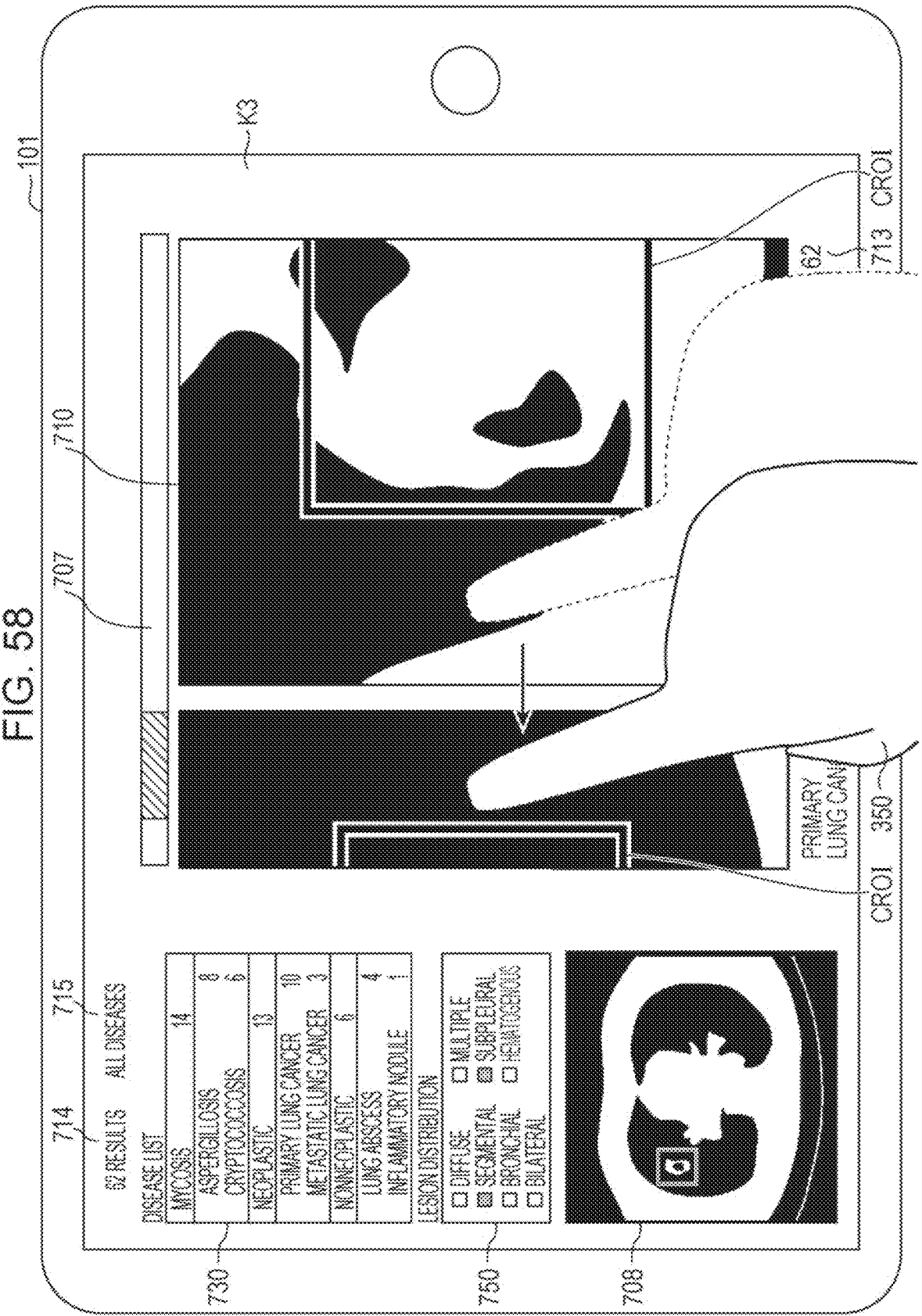
FIG. 58 is a diagram illustrating the base screen in which the thumbnail image displayed in the case display region is switched through the swipe operation performed by the user.
Figure 59:
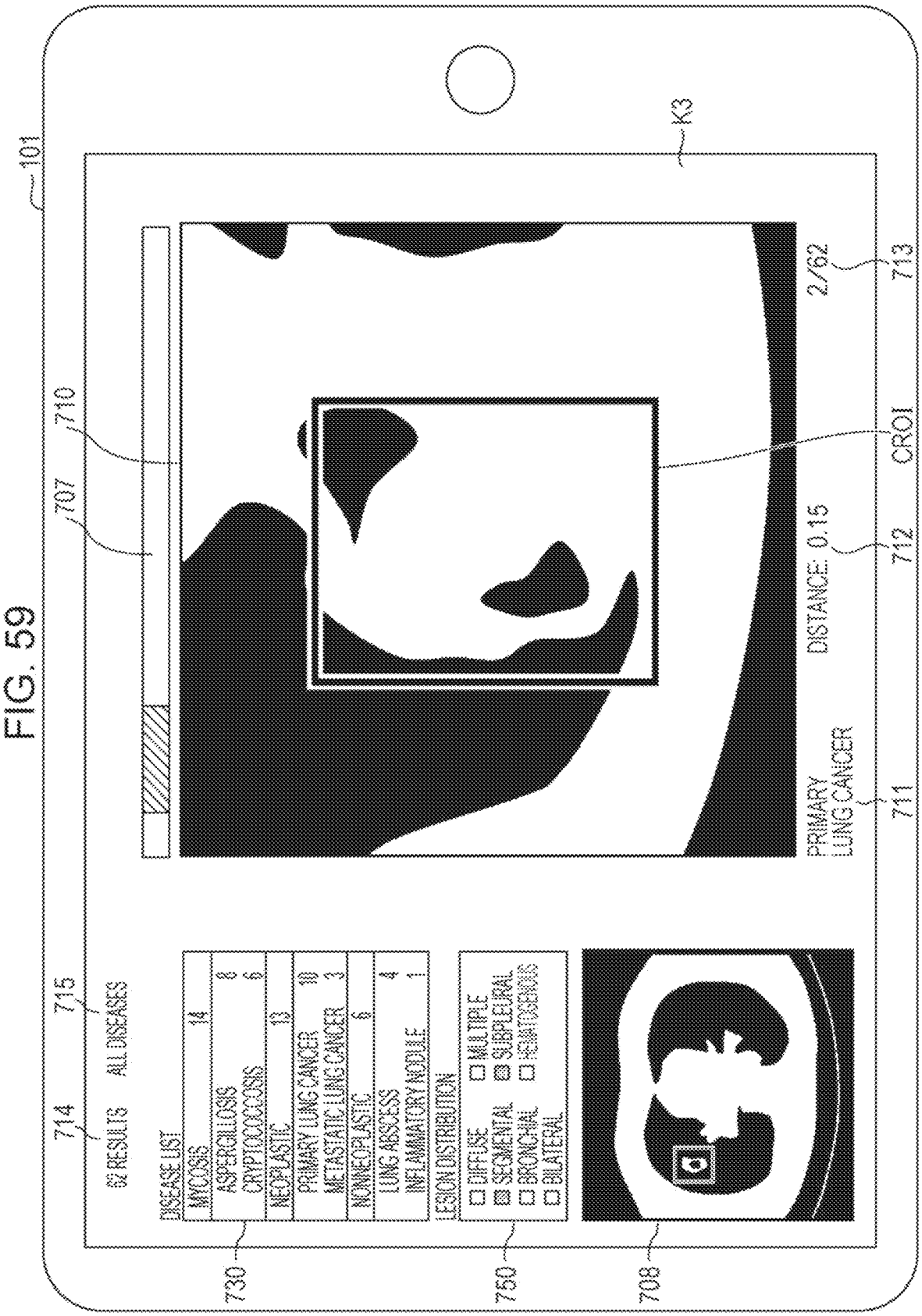
FIG. 59 is a diagram illustrating the base screen in which the thumbnail image displayed in the case display region is switched through the swipe operation performed by the user.

FIG. 53 is a sequence diagram illustrating a process performed until a thumbnail image of a next similar case is displayed after the user performs an enlargement operation. FIG. 54 is a flowchart illustrating the process corresponding to the sequence diagram of FIG. 53. FIGS. 55 and 56 are diagrams illustrating a pinch-out operation performed by the user on a thumbnail image. FIGS. 57 to 59 are diagrams illustrating the base screen K3 in which the thumbnail image displayed in the case display region 710 is switched through a swipe operation performed by the user. In FIG. 54, the same steps as those illustrated in FIG. 53 are given the same reference numerals.

As illustrated in FIGS. 55 and 56, the input control unit 103 of the information terminal 100 detects an enlargement operation (a pinch-out operation in FIGS. 55 and 56) performed by the user (S800). As illustrated in FIGS. 55 and 56, the user performs the pinch-out operation using an object 350 (for example, two fingers of the user). The enlargement operation may be an operation other than the pinch-out operation, that is, for example, a tap operation, instead.

Next, the image generation unit 112 enlarges the thumbnail image of the similar case by an enlargement ratio according to the amount of the pinch-out operation performed by the user (S810). As illustrated in FIG. 56, the display control unit 104 displays an enlarged thumbnail image, which has been generated by the image generation unit 112, in the case display region 710 of the display 101 (S820).

The input control unit 103 of the information terminal 100 detects a swipe operation performed by the user (S830). Next, the image generation unit 112 generates a thumbnail image of a similar case to be displayed next on the basis of the swipe operation. The image generation unit 112 outputs the generated thumbnail image to the display control unit 104 (S840).

As illustrated in FIGS. 57 and 58, the image generation unit 112 generates an intermediate image, in which thumbnail image before switching of the similar case and the thumbnail image after the switching are arranged adjacent to each other, during the swipe operation performed with the object 350 (the user's finger) so that the intermediate image appears in accordance with the swipe operation. The image generation unit 112 outputs the generated intermediate image to the display control unit 104. The display control unit 104 displays the input intermediate image in the case display region 710 (S850).

After the swipe operation is completed, the display control unit 104 displays, as illustrated in FIG. 59, the thumbnail image of the similar case having next highest similarity across the case display region 710 (S860).

In FIG. 55, the thumbnail image in the first row and the first column illustrated in FIG. 5 is displayed across the case display region 710. If a pinch-out operation is performed, the thumbnail image is enlarged as illustrated in FIG. 56 by an enlargement ratio according to the amount of the pinch-out operation. At this time, as illustrated in FIG. 56, the display control unit 104 displays the enlarged thumbnail image such that the center of the CROI matches the center of the case display region 710.

In the second embodiment, as in the first embodiment, if a swipe operation is performed, a position of an image is adjusted such that the CROI is located at the center of the case display region 710 as illustrated in FIGS. 58 and 59. In FIG. 59, an image obtained by enlarging the thumbnail image in the first row and the second column illustrated in FIG. 5 is displayed in the case display region 710.

Furthermore, in the second embodiment, as can be seen from a comparison between FIG. 56 and FIG. 59, an enlargement ratio of a thumbnail image of each similar case changes such that the CROI remains the same. Details of a process performed by the image generation unit 112 according to the second embodiment will be described hereinafter with reference to FIG. 60.

Figure 60:
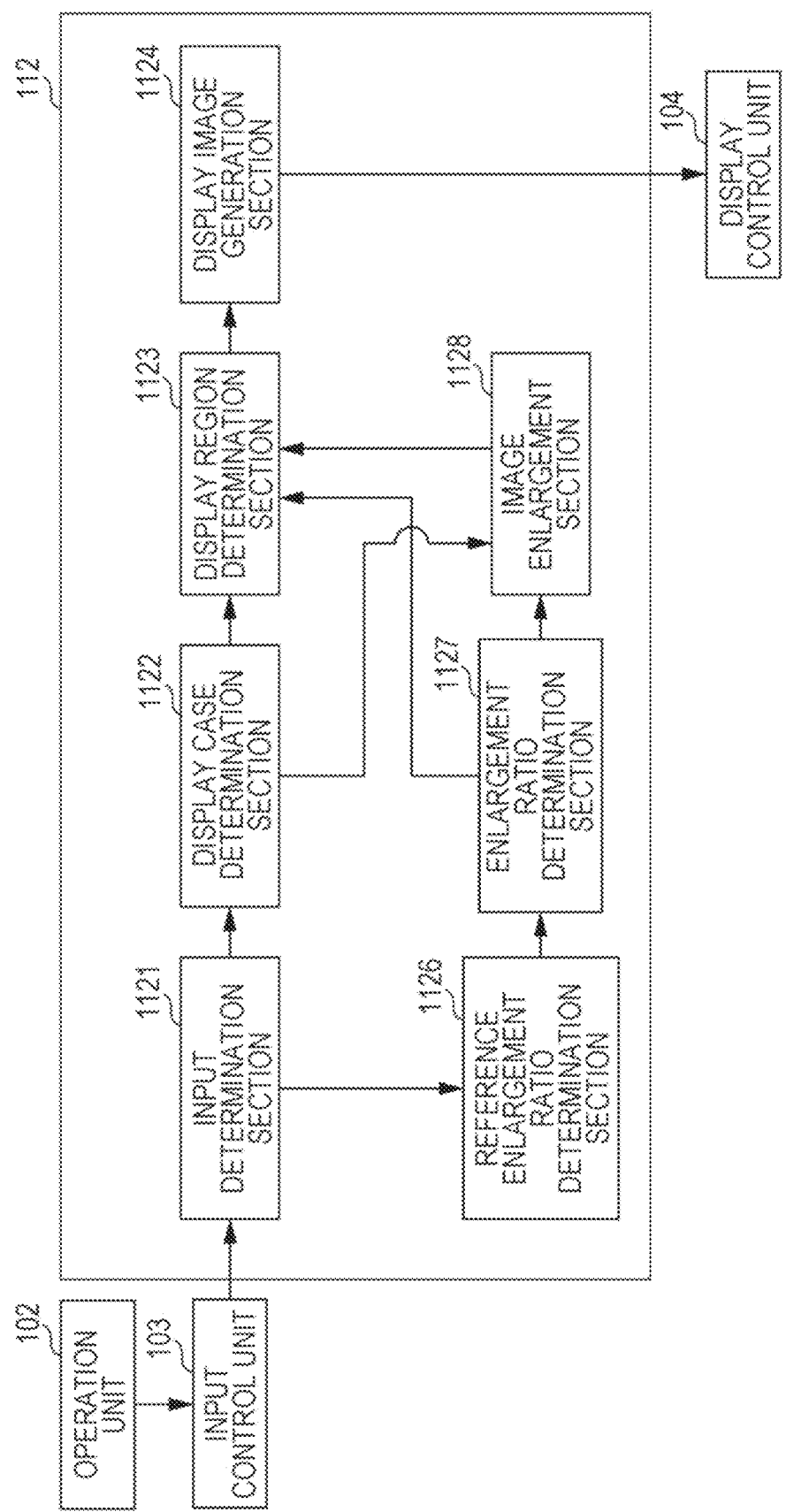
FIG. 60 is a block diagram illustrating a detailed configuration of an image generation unit according to a second embodiment.

FIG. 60 is a block diagram illustrating a detailed configuration of the image generation unit 112 according to the second embodiment. In FIG. 60, the same components as those illustrated in FIG. 48 are given the same reference numerals, and detailed description thereof is omitted.

The image generation unit 112 according to the second embodiment includes the input determination section 1121, the display case determination section 1122, the display region determination section 1123, the display image generation section 1124, a reference enlargement ratio determination section 1126, an enlargement ratio determination section 1127, and an image enlargement section 1128.

If the input control unit 103 detects an operation performed by the user using the operation unit 102, the input control unit 103 outputs a result of the detection to the input determination section 1121. The input determination section 1121 determines the operation performed by the user using the operation unit 102 on the basis of the results of the detection input from the input control unit 103.

If the operation is a swipe operation, the input determination section 1121 outputs information indicating that the operation is a swipe operation and a direction of the swipe operation (for example, leftward or rightward) to the display case determination section 1122.

If the operation is a pinch-out operation, the input determination section 1121 outputs information indicating that the operation is a pinch-out operation and the amount of the pinch-out operation (the amount of movement of the object 350 on the display 101) to the reference enlargement ratio determination section 1126.

The reference enlargement ratio determination section 1126 determines an enlargement ratio for the thumbnail image during the pinch-out operation on the basis of the amount of the pinch-out operation (the amount of movement of the object 350 on the display 101) input from the input determination section 1121. For example, the reference enlargement ratio determination section 1126 multiplies the amount of movement of the object 350 on the display 101 by a predetermined coefficient and determines a product as the enlargement ratio for the thumbnail image during the pinch-out operation. The reference enlargement ratio determination section 1126 outputs the determined reference enlargement ratio to the enlargement ratio determination section 1127. In the following description, a thumbnail image for which a pinch-out operation has been performed will be referred to as a "reference thumbnail image", and an enlargement ratio determined for the thumbnail image for which the pinch-out operation has been performed will be referred to as a "reference enlargement ratio".

The enlargement ratio determination section 1127 determines an enlargement ratio for a thumbnail image of a similar case to be displayed next on the basis of an area of a ROI of the reference thumbnail image, an area of a ROI of the similar case to be displayed next determined by the display case determination section 1122, and the reference enlargement ratio determined by the reference enlargement ratio determination section 1126.

First, the enlargement ratio determination section 1127 calculates the area of the ROI of the reference thumbnail image on the basis of the ROI information 4300 (FIG. 23) regarding a similar case corresponding to the reference thumbnail image. Here, if the area of the ROI of the reference thumbnail image is denoted by Sr, coordinates of an upper-left corner of the ROI are denoted by (xl, yt), and coordinates of a lower-right corner of the ROI are denoted by (xr, yb), the area Sr of the ROI can be calculated using the following expression.

$$Sr=|xl-xr|\times|yt-yb|$$

Next, the enlargement ratio determination section 1127 calculates the area of the ROI from the ROI information 4300 regarding the similar case to be displayed next. Here, if the area of the ROI of a similar case i to be displayed next is denoted by Si, coordinates of an upper-left corner of the ROI are denoted by (xli, yti), and coordinates of a lower-right corner of the ROI are denoted by (xri, ybi), the area Si of the ROI can be calculated using the following expression.

$$Si=|xli-xri|\times|yti-ybi|$$

Finally, the enlargement ratio determination section 1127 calculates the enlargement ratio for the similar case i to be displayed next on the basis of the area Sr of the ROI of the reference thumbnail image, the area Si of the ROI of the similar case i to be displayed next, and the reference enlargement ratio determined for the reference thumbnail image. Here, if the enlargement ratio determined for the reference thumbnail image is denoted by kr, an enlargement ratio ki for the similar case i to be displayed next can be calculated using the following expression.

$$ki=kr(Sr/Si)$$

Figure 62:
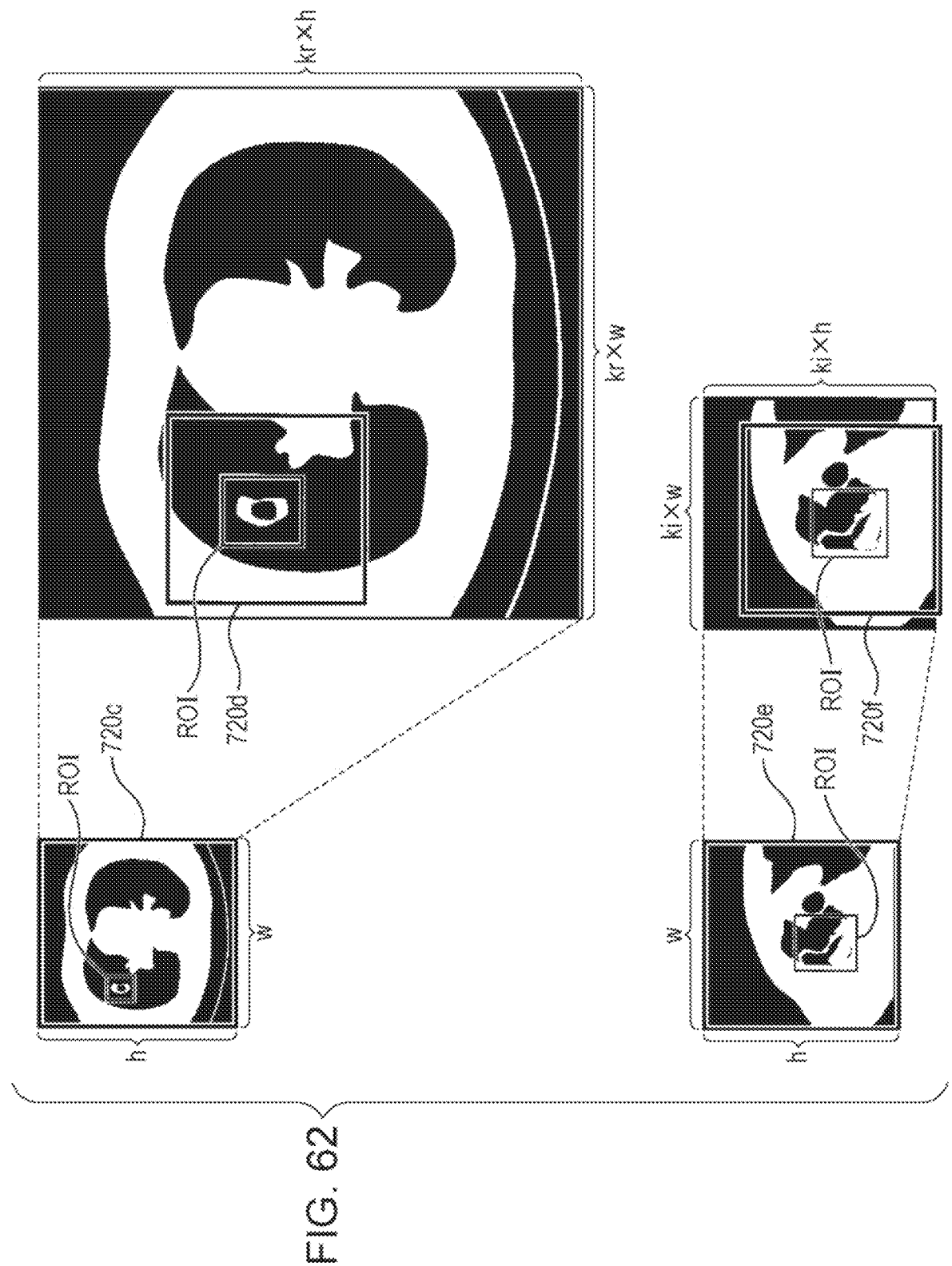
FIG. 62 is a diagram schematically illustrating a reference thumbnail image and a thumbnail image to be displayed next before and after an enlargement process.

Thus, as illustrated in FIG. 62 (referred to later), an enlargement ratio with which the size of a ROI after enlargement becomes the same between the reference thumbnail image and the thumbnail image to be displayed next is calculated.

The image enlargement section 1128 enlarges the thumbnail image of the similar case to be displayed next determined by the display case determination section 1122 by the enlargement ratio determined by the enlargement ratio determination section 1127.

The display region determination section 1123 determines coordinates of a display region of the enlarged thumbnail image on the basis of the enlargement ratio determined by the enlargement ratio determination section 1127 and the ROI information 4300 (FIG. 23) regarding a similar case ID of the similar case to be displayed next such that center coordinates of the ROI of the thumbnail image enlarged by the image enlargement section 1128 match the center of the case display region 710. The display region determined by the display region determination section 1123 will be described with reference to FIG. 61.

Figure 61:
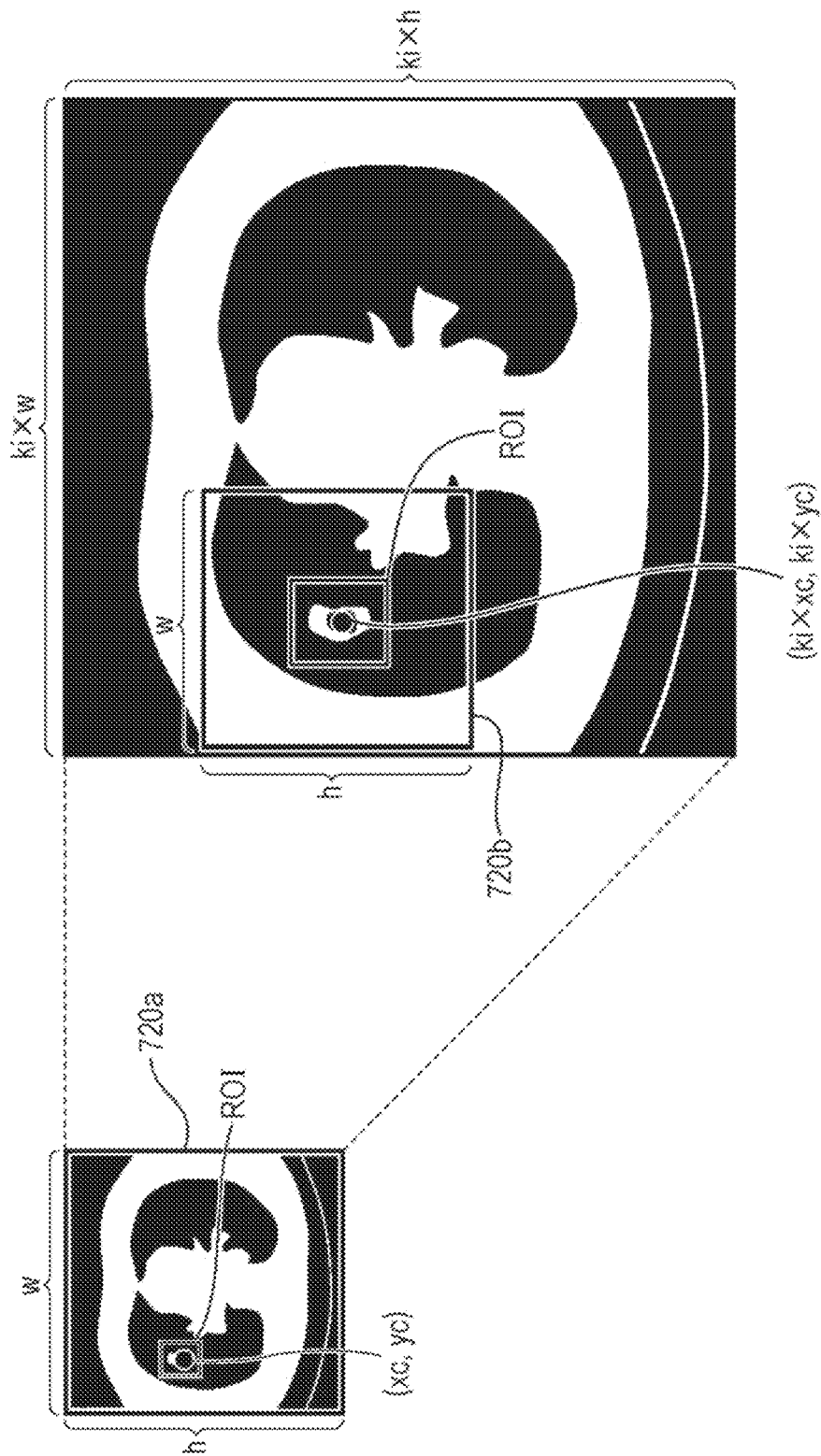
FIG. 61 is a diagram schematically illustrating a relationship between an enlargement ratio and a display region.

FIG. 61 is a diagram schematically illustrating a relationship between an enlargement ration and a display region. If the enlargement ratio is ki, the image enlargement section 1128 generates an enlarged thumbnail image illustrated in a right part of FIG. 61 from a thumbnail image illustrated in a left part of FIG. 61.

If center coordinates of the ROI before the enlargement are denoted by (xc, yc), coordinates (ki×xc, ki×yc), which are obtained by multiplying the center coordinates of the ROI before the enlargement by the enlargement ratio ki, are center coordinates of the ROI after the enlargement as illustrated in FIG. 61.

As indicated in the left part of FIG. 61, a horizontal dimension and a vertical dimension of a display region 720*a* are denoted by w and h, respectively. In this case, a rectangular region illustrated in the right part of FIG. 61 is a display region 720*b*. Coordinates of an upper-left corner of the display region 720*b* are (ki×xc−w/2, ki×yc−h/2), and coordinates of a lower-right corner of the display region 720*b* are (ki×xc+w/2, ki×yc+h/2).

FIG. 62 is a diagram schematically illustrating a reference thumbnail image and a thumbnail image to be displayed next before and after an enlargement process. An upper-left portion of FIG. 62 illustrates the reference thumbnail image before the enlargement process. An upper-right portion of FIG. 62 illustrates the reference thumbnail image after the enlargement process. A lower-left portion of FIG. 62 illustrates the thumbnail image to be displayed next before the enlargement process. A lower-right portion of FIG. 62 illustrates the thumbnail image to be displayed next after the enlargement process.

If the reference thumbnail image illustrated in the upper-left portion of FIG. 62 is enlarged by an enlargement ratio kr, the thumbnail image illustrated in the upper-right portion of FIG. 62 is obtained. The display region determination section 1123 determines a display region 720*d* in the upper-right portion of FIG. 62 such that a center position of the ROI matches a center position of the display region 720*d*. The display region determination section 1123 determines the size of the display region 720*d* such that the size of the display region 720*d* becomes the same as the size of a display region 720*c* before the enlargement process.

If the thumbnail image to be displayed next illustrated in the lower-left portion of FIG. 62 is enlarged by an enlargement ratio ki, the thumbnail image illustrated in the lower-right portion of FIG. 62 is obtained. The display region determination section 1123 determines a display region 720*f* in the lower-right portion of FIG. 62 such that a center position of the ROI matches a center position of the display region 720*f*. The display region determination section 1123 determines the size of the display region 720*f* such that the size of the display region 720*f* becomes the same as the size of a display region 720*e* before the enlargement process.

In FIG. 62, the enlargement ratio ki for the thumbnail image i to be displayed next is determined relative to the enlargement ratio kr for the reference thumbnail image in accordance with an area ratio of the ROIs. Therefore, as illustrated in FIG. 62, the sizes of the ROIs after the enlargement are the same.

In FIG. 60, the display image generation section 1124 generates an image to be displayed in the case display region 710 on the basis of the coordinates of the display region determined by the display region determination section 1123 and the thumbnail image enlarged by the image enlargement section 1128. The display image generation section 1124 outputs the generated image to the display control unit 104.

As a result of the above process, according to the second embodiment, if a thumbnail image is enlarged through, for example, a pinch-out operation and the displayed thumbnail image is switched through a swipe operation, a new enlarged thumbnail image displayed as a result of the switching is displayed such that a ROI thereof is located at the center of the case display region 710.

In general, a position of a ROI of each similar case is different. Therefore, if an enlarged thumbnail image is switched and the enlargement is canceled, an enlargement operation (pinch-out operation) needs to be performed again. On the other hand, if the enlargement is not canceled and a new thumbnail image is displayed, a ROI might be larger than a display region or a position of the ROI might be completely different than before. In this case, the enlargement ratio and the position of the ROI need to be changed. Therefore, if there are many images, this operation might be physically exhausting.

According to the second embodiment, however, the doctor does not need to visually search for a ROI each time a new thumbnail image of a similar case is displayed. In addition, the doctor can observe a ROI immediately without changing the enlargement ratio or the position of the ROI. As a result, when thumbnail images of a plurality of similar cases are sequentially observed through the swipe operation, the observation can be less exhausting and the reading efficiency improves, thereby improving the efficiency of diagnosis.

The present disclosure can be used in a similar case retrieval apparatus that provides similar cases that serve as a reference in making diagnoses using medical images, which are reading targets, a reading educational apparatus for residents studying reading, and the like.

What is claimed is:

1. A method comprising:
   causing a display to display a target medical image being a medical image to be read;
   causing the display to display thumbnail images in a predetermined area included in the display, the thumbnail images corresponding one-to-one to similar medical images, an image feature in each of the similar medical images and an image feature in a region of interest in the target medical image having similarity, the thumbnail images including a first thumbnail image; and
   when receiving selection of the first thumbnail image, (i) causing the display to remove display of the thumbnail images from the predetermined area and (ii) causing the display to display an enlarged first thumbnail image in the predetermined area without the display of the thumbnail images in the predetermined area, the enlarged first thumbnail image corresponding to the first thumbnail image, a size of the enlarged first thumbnail image being larger than a size of the first thumbnail image.

2. The method according to claim 1, wherein
the image feature in each of the similar medial images is an image feature in a region of interest in each of the similar medial images.

3. The method according to claim 1, wherein
the thumbnail images correspond one-to-one to degrees of the similarity,
the thumbnail images are displayed in descending order of the degrees of the similarity in the predetermined area, and
the enlarged first thumbnail image is generated on the basis of a first similar medical image corresponding to the first thumbnail image.

4. The method according to claim 3, further comprising:
receiving information indicating a region of interest in the target medical image, wherein
the thumbnail images including a second thumbnail image displayed adjacent to the first thumbnail image, and
when detecting a swipe operation performed on the enlarged first thumbnail image displayed in the predetermined area, (i) causing the display to remove the display of the enlarged first thumbnail image from the predetermined area and (ii) causing the display to display a part of an enlarged second thumbnail image in the predetermined area without the display of the enlarged first thumbnail image in the predetermined area, the enlarged second thumbnail image being generated on the basis of a second similar medical image corresponding to the second thumbnail image, a size of the enlarged second thumbnail image being larger than a size of the second thumbnail image.

5. A nonvolatile recording medium storing a program executed by an apparatus, the program causing the apparatus to perform:
causing a display to display a target medical image being a medical image to be read;
causing the display to display thumbnail images in a predetermined area included in the display, the thumbnail images corresponding one-to-one to similar medical images, an image feature in each of the similar medical images and an image feature in a region of interest in the target medical image having similarity, the thumbnail images including a first thumbnail image; and
when receiving selection of the first thumbnail image, (i) causing the display to remove display of the thumbnail images from the predetermined area and (ii) causing the display to display an enlarged first thumbnail image in the predetermined area without the display of the thumbnail images in the predetermined area, the enlarged first thumbnail image corresponding to the first thumbnail image, a size of the enlarged first thumbnail image being larger than a size of the first thumbnail image.

6. The nonvolatile recording medium according to claim 5, wherein
the image feature in each of the similar medial images is an image feature in a region of interest in each of the similar medial images.

7. The nonvolatile recording medium according to claim 5, wherein
the thumbnail images correspond one-to-one to degrees of the similarity,
the thumbnail images are displayed in descending order of the degrees of the similarity in the predetermined area, and
the enlarged first thumbnail image is generated on the basis of a first similar medical image corresponding to the first thumbnail image.

8. The nonvolatile recording medium according to claim 7, further comprising:
receiving information indicating a region of interest in the target medical image, wherein
the thumbnail images including a second thumbnail image displayed adjacent to the first thumbnail image, and
when detecting a swipe operation performed on the enlarged first thumbnail image displayed in the predetermined area, (i) causing the display to remove the display of the enlarged first thumbnail image from the predetermined area and (ii) causing the display to display a part of an enlarged second thumbnail image in the predetermined area without the display of the enlarged first thumbnail image in the predetermined area, the enlarged second thumbnail image being generated on the basis of a second similar medical image corresponding to the second thumbnail image, a size of the enlarged second thumbnail image being larger than a size of the second thumbnail image.

9. An apparatus comprising:
a processor, wherein
the processor causes a display to display a target medical image being a medical image to be read,
the processor causes the display to display thumbnail images in a predetermined area included in the display, the thumbnail images corresponding one-to-one to similar medical images, an image feature in each of the similar medical images and an image feature in a region of interest in the target medical image having similarity, the thumbnail images including a first thumbnail image, and
when the processor receives selection of the first thumbnail image, the processor causes the display to remove display of the thumbnail images from the predetermined area and (ii) causes the display to display an enlarged first thumbnail image in the predetermined area without the display of the thumbnail images in the predetermined area, the enlarged first thumbnail image corresponding to the first thumbnail image, a size of the enlarged first thumbnail image being larger than a size of the first thumbnail image.

10. The apparatus according to claim 9, wherein
the image feature in each of the similar medial images is an image feature in a region of interest in each of the similar medial images.

11. The apparatus according to claim 9, wherein
the thumbnail images correspond one-to-one to degrees of the similarity,
the thumbnail images are displayed in descending order of the degrees of the similarity in the predetermined area, and
the enlarged first thumbnail image is generated on the basis of a first similar medical image corresponding to the first thumbnail image.

12. The apparatus according to claim 11, wherein
the processor receives information indicating a region of interest in the target medical image,
the thumbnail images includes a second thumbnail image displayed adjacent to the first thumbnail image, and
when the processor detects a swipe operation performed on the enlarged first thumbnail image displayed in the predetermined area, (i) the processor causes the display to remove the display of the enlarged first thumbnail image from the predetermined area and (ii) the processor causes the display to display a part of an enlarged second thumbnail image in the predetermined area without the display of the enlarged first thumbnail image in the predetermined area, the enlarged second thumbnail image being generated on the basis of a second similar medical image corresponding to the second thumbnail image, a size of the enlarged second thumbnail image being larger than a size of the second thumbnail image.

* * * * *